US008143385B2

(12) United States Patent
Valge-Archer et al.

(10) Patent No.: US 8,143,385 B2

(45) Date of Patent: Mar. 27, 2012

(54) NUCLEIC ACIDS CODING FOR ANTIBODIES AGAINST HUMAN IL-21 RECEPTOR AND USES THEREFOR

(75) Inventors: Viia Valge-Archer, Little Abington (GB); Andrew James Williams, Royston (GB); Deborah A. Young, Melrose, MA (US); Matthew J. Whitters, Hudson, MA (US); Mary Collins, Natick, MA (US); Joann Witek, Acton, MA (US)

(73) Assignees: Wyeth LLC, Madison, NJ (US); MedImmune Ltd., Cambridge (GB)

( * ) Notice: Subject to any disclaimer, the term of this patent is extended or adjusted under 35 U.S.C. 154(b) by 247 days.

(21) Appl. No.: 12/353,812

(22) Filed: Jan. 14, 2009

(65) Prior Publication Data

US 2010/0297151 A1 Nov. 25, 2010

Related U.S. Application Data

(62) Division of application No. 10/798,380, filed on Mar. 12, 2004, now Pat. No. 7,495,085.

(60) Provisional application No. 60/454,336, filed on Mar. 14, 2003.

(51) Int. Cl.

*C07H 21/04* (2006.01)
*A61K 39/00* (2006.01)
*C12N 5/16* (2006.01)
*H01N 33/53* (2006.01)

(52) U.S. Cl. ............... 536/23.53; 424/133.1; 424/135.1; 435/7.1; 435/326; 435/328; 435/331; 436/547

(58) Field of Classification Search ........................ None
See application file for complete search history.

(56) References Cited

U.S. PATENT DOCUMENTS 4,179,337 A 12/1979 Davis et al. .................... 435/181
4,301,144 A 11/1981 Iwashita et al. ................. 424/78
4,495,285 A 1/1985 Shimizu et al. ............... 435/215
4,496,689 A 1/1985 Mitra ........................... 525/54.1
4,522,811 A 6/1985 Eppstein et al. .................. 514/2
4,609,546 A 9/1986 Hiratani .......................... 424/83
4,640,835 A 2/1987 Shimizu et al. ................. 424/94
4,670,417 A 6/1987 Iwasaki et al. .................... 514/6
4,766,106 A 8/1988 Katre et al. ..................... 514/12
4,791,192 A 12/1988 Nakagawa et al. ........... 530/399
4,816,567 A 3/1989 Cabilly et al. ................ 530/387
5,011,912 A 4/1991 Hopp et al. .................... 530/387
5,565,332 A 10/1996 Hoogenboom et al. ...... 435/69.1
5,624,821 A 4/1997 Winter et al. ................ 435/69.6
5,648,260 A 7/1997 Winter et al. .............. 435/252.3
6,057,128 A 5/2000 Donaldson et al. .......... 435/69.1
6,258,562 B1 7/2001 Salfeld et al. ................ 435/69.6
6,307,024 B1 10/2001 Novak et al. .................. 530/351
6,350,892 B1 2/2002 Banville et al. ............... 556/436
6,576,744 B1 6/2003 Presnell et al. ............... 530/351
7,189,400 B2 3/2007 Carter et al. ............... 424/185.1
7,198,789 B2 4/2007 Carter et al. ............... 424/130.1
7,314,623 B2 1/2008 Grusby et al. ............. 424/185.1
2001/0025022 A1 9/2001 Kikly et al. ........................ 514/2
2002/0090680 A1 7/2002 Hodge .......................... 435/69.1
2002/0128446 A1 9/2002 Novak et al. .................. 530/351
2002/0137677 A1 9/2002 Sprecher et al. ................ 514/12
2002/0160451 A1 10/2002 Masiakowski et al. ...... 435/69.1
2003/0049798 A1 3/2003 Carter et al. ................. 435/69.7
2003/0108549 A1 6/2003 Carter et al. ............... 424/145.1
2003/0148447 A1 8/2003 Presnell et al. .............. 435/69.1
2004/0016010 A1 1/2004 Kasaian et al. ................. 800/18
2006/0024268 A1 2/2006 Ksaian et al. ................ 424/85.2
2006/0039902 A1 2/2006 Young et al. ............... 424/133.1
2006/0159655 A1 7/2006 Collins et al. ................ 424/85.2
2006/0257403 A1 11/2006 Young et al. ............... 424/144.1
2008/0167241 A1 7/2008 Donaldson et al. ............. 514/12
2008/0241098 A1 10/2008 Young et al. ................. 424/85.2
2009/0197803 A1 8/2009 Grusby et al. .................. 514/12

FOREIGN PATENT DOCUMENTS

| | | |
|---|---|---|
| EP | 0 388 151 | 9/1990 |
| EP | 0 812 913 | 12/1997 |
| EP | 1 088 831 | 4/2001 |
| FR | 2 724 182 | 3/1996 |
| WO | WO 87/05330 | 9/1987 |
| WO | WO 92/01047 | 1/1992 |
| WO | WO 94/29351 | 12/1994 |
| WO | WO 96/04388 | 2/1996 |
| WO | WO 96/07754 | 3/1996 |
| WO | WO 97/45544 | 12/1997 |
| WO | WO 97/47741 | 12/1997 |
| WO | WO 97/47742 | 12/1997 |
| WO | WO 98/11225 | 3/1998 |

(Continued)

OTHER PUBLICATIONS

Chtanova et al. (2004) “T Follicular helper cells express a distinctive transcriptional profile, reflecting their role as non-Th1/Th2 effector cells that provide help for B cells.” *J. Immunol.* 173(1): 68-78.

Brenne et al. (2002) “Interleukin-21 is a growth and survival factor for human myeloma cells.” *Blood* 99(10):3756-62.

Janeway et al., Immunobiology: The Immune System in Health and Disease, Chapter 3 and Glossary, 5th Edition, New York Garland Publishing (2001).

Collins et al., “IL-21 and IL-21 Receptor,” Immunologic Res., 28: 131-140 (2003).

Woodcock et al., “Three Residues in the Common γβ Chain of the Human GM-CSF, IL-3 and IL-5 Receptors are Essential for GM-CSF and IL-5 but not IL-3 High Affinity Binding and Interact with Glu21 of GM-CSF,” EMBO J., 13: 5176-5185 (1994).

Mulhern et al., “The Solution Structure of the Cytokine-binding Domain of the Common β-Chain of the Receptors for Granulocyte-Macrophage Colony-stimulating Factor, Interleukin-3 and Interleukin-5,” J. Mol. Biol., 297: 989-1001 (2000).

(Continued)

*Primary Examiner* — Elly-Gerald Stoica

(74) *Attorney, Agent, or Firm* — Fitzpatrick, Cella, Harper & Scinto

(57) ABSTRACT

The present application provides human antibodies and antigen binding fragments thereof that specifically bind to the human interleukin-21 receptor (IL-21R). The antibodies can act as antagonists of IL-21R activity, thereby modulating immune responses in general, and those mediated by IL-21R in particular. The disclosed compositions and methods may be used for example, in diagnosing, treating or preventing inflammatory disorders, autoimmune diseases, allergies, transplant rejection, cancer, and other immune system disorders.

12 Claims, 12 Drawing Sheets

FOREIGN PATENT DOCUMENTS

| | | | |
|---|---|---|---|
| WO | WO 98/31811 | | 7/1998 |
| WO | WO 99/47675 | | 9/1999 |
| WO | WO 00/08152 | | 2/2000 |
| WO | WO 00/17235 | | 3/2000 |
| WO | WO 00/27882 | | 5/2000 |
| WO | WO/00/69880 | * | 5/2000 |
| WO | WO 00/53761 | | 9/2000 |
| WO | WO 00/56772 | | 9/2000 |
| WO | WO 00/69880 | | 11/2000 |
| WO | WO 01/14424 | | 3/2001 |
| WO | WO 01/27279 | | 4/2001 |
| WO | WO 01/36467 | | 5/2001 |
| WO | WO 01/55112 | | 8/2001 |
| WO | WO 01/77171 | | 10/2001 |
| WO | WO 01/85792 | | 11/2001 |
| WO | WO 02/02641 | | 1/2002 |
| WO | WO 03/028630 | | 4/2003 |
| WO | WO 03/040313 | | 5/2003 |
| WO | WO 2004/007682 | | 1/2004 |
| WO | WO 2004/083249 | | 9/2004 |
| WO | WO 2004/084835 | | 10/2004 |
| WO | WO 2005/112983 | | 12/2005 |
| WO | WO 2006/113331 | | 10/2006 |
| WO | WO 2006/135385 | | 12/2006 |
| WO | WO 2009/100035 | | 8/2009 |

OTHER PUBLICATIONS

Schimmenti et al., "Localization of an Essential Ligand Binding Determinant of the Human Erythropoietin Receptor to a Domain N-Terminal to the WSXWS Motif: Implications for Soluble Receptor Function," Exp. Hematol., 23: 1341-1346 (1995).

LaRosa et al., "Amino Terminus of the Interleukin-8 Receptor is a Major Determinant of Receptor Subtype Specificity," J. Biol. Chem, 267: 25402-25406 (1992).

Imler et al., "Identification of the Three Adjacent Amino Acids of Interleukin-2 Receptor β Chain Which Control the Affinity and the Specificity of the Interaction with Interleukin-2," EMBO J., 11: 2047-2053 (1992).

Muyldermans, "Single Domain Camel Antibodies: Current Status," Rev. Mol. Biotech., 74: 277-301 (2001).

Muyldermans et al., "Recognition of Antigens by Single Domain Antibody Fragments: The Superfluous Luxury of Paired Domains," Trends Biochem. Sci., 26:230-235 (2001).

van den Beucken et al. "Building Novel Binding Ligands to B7.1 and B7.2 Based on Human Antibody Single Variable Light Chain Domains," J. Mol. Biol., 310: 591-601 (2001).

Eilat et al., "The Mechanism by which a Peptide Based on Complementarity-determining Region-1 of a Pathogenic Anti-DNA Auto-Ab Ameliorates Experimental Systemic Lupus Erythematosus," Proc. Natl. Acad. Sci. USA, 98: 1148-1153 (2001).

Davis et al., Basic Methods in Molecular Biology §20-3: "Site-directed Mutagenesis," pp. 738-744, 2nd Edition, Appleton & Lange, CT (1994).

Altschul et al., "Basic Local Alignment Search Tool," J. Mol. Biol., 215: 403-410 (1990).

Aplin et al., "Preparation Properties, and Applications of Carbohydrate Conjugates of Proteins and Lipids," CRC Crit. Rev. Biochem., 10: 259-306 (1981).

Asao et al., "Cutting Edge: The Common γ-Chain is an Indispensable Subunit of the IL-21 Receptor Complex," J. Immunol., 167: 1-5 (2001).

Barbas et al., "In Vitro Evolution of a Neutralizing Human Antibody to Human Immunodeficiency Virus Type 1 to Enhance Affinity and Broaden Strain Cross-reactivity," Proc. Natl. Acad. Sci. USA, 91: 3809-3813 (1994).

Baumgartner et al., "Double Blind, Placebo Controlled Trial of Tumor Necrosis Factor Receptor Fusion Protein (TNFR:Fc) in Active Rheumatoid Arthritis," J. Invest. Med., 44(3): 235A (1996).

Bazan, "Structural Design and Molecular Evolution of a Cytokine Receptor Superfamily," Proc. Natl. Acad. Sci. USA, 87: 6934-6938 (1990).

Bird et al., "Single-chain Antigen-binding Proteins," Science, 242: 423-426 (1998).

Biró et al., "The Effect to WSEWS Pentapeptide and WSEWS-Specific Monoclonal Antibodies on Constitutive and IL-6 Induced Acute-phase Protein Production by a Human Hepatoma Cell Line, HEPG-2," Immunology Letters, 46: 183-187 (1995).

Caput et al., "Cloning and Characterization of a Specific Interleukin (IL)-13 Binding Protein Structurally Related to the IL-5 Receptor α Chain," J. Biol. Chem., 271(28): 16921-16926 (1996).

Chikanza et al., "Treatment of Patients with Rheumatoid Arthritis with RP73401 Phosphodiesterase Type IV Inhibitor," Arthritis and Rheumatism, 39(9): S282, Abstract 1527 (1996).

Clackson et al., "Making Antibody Fragments Using Phage Display Libraries," Nature, 352: 624-628 (1991).

Courtenay et al., "Immunisation Against Heterologous Type II Collagen Induces Arthritis in Mice," Nature, 283: 666-668 (1980).

D'Andrea et al., "Expression Cloning of the Murine Erythropoietin Receptor," Cell, 57: 277-285 (1989).

Debinski et al., "A Novel Chimeric Protein Composed of Interleukin 13 and *Pseudomonas* Exotoxin in Highly Cytotoxic to Human Carcinoma Cells Expressing Receptors for Interleukin 13 and Interleukin 4," J. Biol. Chem., 270(28): 16775-16780 (1995).

Dusanter-Fourt et al., "Transduction du Signal par les Récepteurs de Cytokines," Synthèse, 10: 825-835 (1994), English Abstract.

Edge et al., "Deglycosylation of Glycoproteins by Trifluoromethanesulfonic Acid," Anal. Biochem., 118: 131-137 (1981).

Ehrich et al., "Demonstration of Selective Cox-2 Inhibition by MK-966 in Humans," Arthritis and Rheumatism, 39(9): S81, Abstract 328 (1996).

Elit, "CCI-779 Wyeth," Curr. Opin. Invest. Drugs, 3: 1249-1253 (2002).

Engström., "The Arrangement of the Protein Molecules in Nuclear-polyhedrosis Inclusions," Biochem. Exp. Biol., 11: 7-13 (1974).

Evans et al., "Efficacy of Tumor Necrosis Factor Binding Protein (TNF-bp) in the Streptococcal Cell Wall-induced Reactivation Model of Arthritis," Arthritis and Rheumatism, 39(9): S284, Abstract 1540 (1996).

Farr et al., "Sulphasalazine (SASP) in Rheumatoid Arthritis (RA): A 5 Year Prospective Study," Arthritis and Rheumatism, 39(9): S281, Abstract 1519 (1996).

Fiebich et al., "Effects of NSAIDs on IL-1 β Induced IL-6 mRNA and Protein Synthesis in Human Astrocytoma Cells," Neuroimmunol., 7: 1209-1213 (1996).

Finnegan et al., "Leflunomide Inhibits Immunoglobulin Production by Two Separate Mechanisms," Arthritis and Rheumatism, 39(9): S131, Abstract 627 (1996).

Fulmer et al., "Transplantation of Cardiac Tissue into the Mouse Ear," Am. J. Anatomy, 113: 273-281 (1963).

Gram et al., "In Vitro Selection and Affinity Maturation of Antibodies from a Naive Combinatorial Immunoglobulin Library," Proc. Natl. Acad. Sci. USA, 89: 3576-3580 (1992).

Griffiths et al., "Human Anti-self Antibodies with High Specificity from Phage Display Libraries," EMBO J., 12: 725-734 (1993).

Guttadauria, "Tenidap in Rheumatoid Arthritis Collaborative International Study (Tracis): A 6-month Interim Analysis," Arthritis and Rheumatism, 39(9): S280, Abstract 1516 (1996).

Hatakeyama et al., "Interleukin-2 Receptor Chain Gene: Generation of Three Receptor Forms by Cloned Human and Chain cDNA's," Science, 244: 552-556 (1989).

Hieter et al., "Clustered Arrangement of Immunogloublin λ Constant Region Genes in Man," Nature, 294: 536-540 (1981).

Hillier et al., "Generation and Analysis of 280,000 Human Expressed Sequence Tags," Genome Res., 6(9): 807-828 (1996).

Holmdahl et al., "The Molecular Pathogenesis of Collagen-induced Arthritis in Mice—A Model for Rheumatoid Arthritis," Ageing Res. Rev., 1: 135-147 (2002).

Huang et al., "Inhibitors of Mammalian Target of Rapamycin as Novel Antitumor Agents: From Bench to Clinic," Curr. Opin. Investig. Drugs, 3: 295-304 (2002).

Huston et al., "Protein Engineering of Antibody Binding Sites: Recovery of Specific Activity in an Anti-Digoxin Single-chain Fv Analogue Produced in *Escherichia coli*," Proc. Natl., Acad Sci. USA, 85: 5879-5883 (1988).

Junghans et al., "Anti-Tac-H, A Humanized Antibody to the Interleukin 2 Receptor with New Features for Immunotherapy in Malignant and Immune Disorders," Cancer Res., 50: 1495-1502 (1990).
Kasaian et al., "IL-21 Limits NK Cell Responses and Promotes Antigen Specific T Cell Activation: A Mediator of the Transition from Innate to Adaptive Immunity," Immunity, 16: 559-569 (2002).
Köhler et al., "Continuous Cultures of Fused Cells Secreting Antibody of Predefined Specificity," Nature, 256: 495-499 (1975).
Lai et al., "STAT3 and STAT5B are Targets of Two Different Signal Pathways Activated by Hematopoietin Receptors and Control Transcription via Separate Cytokine Response Elements," J. Biol. Chem., 270(40): 23254-23257 (1995).
Lenschow et al., "Long-term Survival of Xenogeneic Pancreatic Islet Grafts Induced by CTLA4Ig," Science, 257: 789-792 (1992).
"*Homo sapiens* Chromosome 16 BAC Clone CIT987-SKA-670B5, Complete Genomic Sequence," EMBL Database Entry HUAC2303; Accession No. AC002303 (2002).
Ma et al., "IL-21 Activates Both Innate and Adaptive Immunity to Generate Potent Antitumor Responses that Require Perforin but are Independent of IFN-$\gamma^1$," J. Immunol., 171: 608-615 (2003).
McLennan et al., "Structure-function Relationships in the $CA^{2+}$—Binding and Translocation Domain of SERCA1: Physiological Correlates in Brody Disease," Acta Physiol. Scand. Suppl., 643: 55-67 (98).
Mallat et al., "Interleukin-18/Interleukin-18 Binding Protein Signaling Modulates Atherosclerotic Lesion Development and Stability," Circ. Res., 89: e41-e45 (2001).
Marks et al., "By-passing Immunization: Building High Affinity Human Antibodies by Chain Shuffling," Biotech., 10: 779-783 (1992).
Marks et al., "Human Antibodies from V-Gene Libraries Displayed on Phage," J. Mol. Biol., 222: 581-597 (1991).
Mehta et al., "IL-21 Induces the Apoptosis of Resting and Activated Primary Cells," J. Immunol., 170: 4111-4118 (2003).
Moreland et al., "Soluble Tumor Necrosis Factor Receptor (sTNFR): Results of a Phase I Dose-escalation Study in Patients with Rheumatoid Arthritis," Arthritis and Rheumatism, 37(9): S295, Abstract 813 (1994).
Myers et al., "Optimal Alignments in Linear Space," CABIOS, 4: 11-17 (1988).
Needleman et al., "A General Method Applicable to the Search for Similarities in the Amino Acid Sequence of Two Proteins," J. Mol. Biol., 48: 443-453 (1970).
"Mus Musculus mRNA for Novel Cytokine Receptor NR8, Complete Cds," EMBL/GenBank/DDBJ Databases, Accession No. AB049137 (2000).
O'Dowd et al., "Cloning and Chromosomal Mapping of Four Putative Novel Human G-protein-coupled Receptor Genes," Gene, 187: 75-81 (1997).
Ozaki et al., "Cloning of a Type I Cytokine Receptor Most Related to the IL-2 Receptor β Chain," Proc. Natl. Acad. Sci. USA, 97: 11439-11444 (2000).
Page et al., "An Antiproliferative Bioassay of Interleukin-4," J. Immunol. Meth., 189: 129-135 (1996).
Parrish-Novak et al., "Interleukin 21 and its Receptor are Involved in NK Cell Expansion and Regulation of Lymphocyte Function," Nature, 408: 57-63 (2000).
Sasaki et al., "Structure-Mutation Analysis of the ATPase Site of *Dictyostelium discoideum* Myosin II," Adv. Biophys., 35: 1-24(1998).
Schier et al., "Isolation of Picomolar Affinity Anti-c-erbB-2 Single-chain Fv by Molecular Evolution of the Complementarity Determining Regions in the Center of the Antibody Binding Site," J. Mol. Biol., 263:551-567 (1996).
Sewell et al., "$DAB_{486}$IL-2 Fusion Toxin in Refractory Rheumatoid Arthritis," Arthritis and Rheumatism, 36: 1223-1233 (1993).
Sobel et al., "The Immunopathology of Experimental Allergic Encephalomyelitis," J. Immunol., 132: 2393-2401 (1984).
Sojar et al., "A Chemical Method for the Deglycosylation of Proteins," Arch. Biochem. Biophys., 259: 52-57 (1987).
Takahashi et al., "Structure of Human Immunoglobulin Gamma Genes: Implications for Evolution of a Gene Family," Cell, 29:671-679 (1982).
Thoss et al., "Immunomodulation of Rat Antigen-induced Arthritis by Leflunomide Alone and in Combination with Cyclosporin A," Inflamm. Res., 45: 103-107 (1996).
Thotakura et al., "Enzymatic Deglycosylation of Glycoproteins," Meth. Enzymol., 138: 350-359 (1987).
Traugott, "Detailed Analysis of Early Immunopathologic Events During Lesion Formation in Acute Experimental Autoimmune Encephalomyelitis," Cell Immunol., 119: 114-129 (1989).
Tuohy et al., "A Synthetic Peptide From Myelin Proteolipid Protein Induces Experimental Allergic Encephalomyelitis," J. Immunol., 141: 1126-1130 (1988).
Vaickus et al., "Immune Markers in Hematologic Malignancies," Crit. Rev. in Oncol./Hemotol., 11: 267-297 (1991).
Vaughan et al., "Human Antibodies with Sub-nanomolar Affinities Isolated from a Large Non-immunized Phage Display Library," Nature Biotech., 14:309-314 (1996).
Vita et al., "Characterization and Comparison of the Interleukin 13 Receptor with the Interleukin 4 Receptor on Several Cell Types," J. Biol. Chem., 270(8): 3512-3517 (1995).
Ward et al., "Binding Activities of a Repertoire of Single Immunoglobulin Variable Domains Secreted from *Escherichia coli*," Nature, 341: 544-546 (1989).
Williams et al., "Successful Therapy of Collagen-induced Arthritis with TNF Receptor-IgG Fusion Protein and Combination with Anti-CD4," Immunol., 84: 433-439 (1995).
Wurster et al., "Interleukin 21 is a T Helper (Th) Cell 2 Cytokine that Specifically Inhibits the Differentiation of Naive Th Cells into Interferon γ-producing Th1 Cells," J. Exp. Med., 196(7): 969-977 (2002).
Yan et al., "Two-amino Acid Molecular Switch in an Epithelial Morphogen That Regulates Binding to Two Distinct Receptors," Science, 290: 523-527 (2000).
Yasuf-Makagiansar et al., "Inhibition of LFA-1/ICAM-1 and VLA-4/VCAM-1 as a Therapeutic Approach to Inflammation and Autoimmune Diseases," Med. Res. Rev., 22: 146-167 (2002).
Zhang et al., "Identification, Purification, and Characterization of a Soluble Interleukin (IL)-13-Binding Protein," J. Biol. Chem., 272(14): 9474-9480 (1997).
S. Barth et al., "Combining Phage Display and Screening of cDNA Expression Libraries: A New Approach for Identifying the Target Antigen of an scFv Preselected by Phage Display," J. Mol. Biol., 301(4), pp. 751-757 (Aug. 25, 2000) (Abstract).
D. O'Connell et al., "Phage Versus Phagemid Libraries for Generation of Human Monoclonal Antibodies," J. Mol. Biol., 321(1), pp. 49-56 (Aug. 2, 2002) (Abstract).
A. Kortt et al., "Single-chain Fv Fragments of Anti-Neuraminidase Antibody NC10 Containing Five- and Ten-Residue Linkers Form Dimers and with Zero-Residue Linker a Trimer," Protein Engineering, 10(4):423-433 (1997).
W. Wolfson, "Ablynx Makes Nanobodies from Llama Bodies," Chemistry & Biology, 13:1243-1244 (Dec. 2006).
P. Jones et al., "Replacing the Complementarity-Determining Regions in a Human Antibody with Those From a Mouse," Nature, 321:522-525 (May 29, 1986).
Interleukin 21 Receptor, NCBI Entrez Gene, Accession No. Q9JHX3 (2000).
Communication of a Notice of Opposition against European Patent No. 1 603 949, mailed Nov. 5, 2010; 36 pages.
Patentee's Reply to the Communication of a Notice of Opposition against European Patent No. 1 603 949, dated Jun. 16, 2011; 24 pages.
Yuji Ito (2002) A front-line of techniques for producing an antibody—Part 2: Phage Display Library Method, *Bio Venture* 2(4):51-58; and English abstract.
Toshihiro Nakashima (2002) A front-line of techniques for producing an antibody—Part 3: Practicality in Production of Human Antibody Phage Display Library, *Bio Venture* 2(4):59-66; and English abstract.
Herber et al. (2007) IL-21 Has a Pathogenic Role in a Lupus-Prone Mouse Model and Its Blockade with IL-21 R.Fc Reduces Disease Progression, *J. Immunol*. 178:3822-30.
Young et al. (2007) Blockade of the Interleukin-21/Interleukin-21 Receptor Pathway Ameliorates Disease in Animal Models of Rheumatoid Arthritis, *Arthritis and Rheumatism* 56:1152-63.
Søndergaard and Skak (2009) IL-21: Roles in Immunopathology and Cancer Therapy, *Tissue Antigens* 74:467-79.

* cited by examiner

NUCLEIC ACIDS CODING FOR ANTIBODIES AGAINST HUMAN IL-21 RECEPTOR AND USES THEREFOR

PRIORITY INFORMATION

This application is a divisional application of U.S. application Ser. No. 10/798,380, filed Mar. 12, 2004, now U.S. Pat. No. 7,495,085; both applications claim the benefit of priority of U.S. Provisional Patent Application No. 60/454,336, filed Mar. 14, 2003.

TECHNICAL FIELD

This invention relates to antibodies, e.g., human antibodies, and antigen-binding fragments thereof that bind the interleukin-21 (IL-21) receptor, in particular, the human IL-21 receptor, and their use in regulating immune responses mediated by the IL-21 receptor. The antibodies disclosed herein are useful in diagnosing, preventing, and/or treating immune disorders, e.g., autoimmune disorders.

BACKGROUND OF THE INVENTION

Antigens initiate immune responses and activate the two largest populations of lymphocytes: T cells and B cells. After encountering antigen, T cells proliferate and differentiate into effector cells, while B cells proliferate and differentiate into antibody-secreting plasma cells. Proliferation and differentiation of lymphocytes are regulated by extracellular proteins. Some of these proteins are called cytokines, which are small proteins (<30 kDa) secreted by lymphocytes and other cell types.

Interleukin-21 (IL-21) is a recently discovered cytokine, which is closely related to IL-2, IL-4 and IL-15 (Parrish-Novak et al. (2000) *Nature* 408:57-63). Human IL-21 has a molecular weight of about 15 kDa, consists of 131 amino acids, and shares about 57% identity with mouse IL-21. IL-21 is produced primarily by activated CD4+ T cells.

IL-21 receptor (IL-21R) is a transmembrane, IL-21-binding protein that belongs to the class I cytokine receptor family. Both human and mouse IL-21R have been described in WO 01/85792, herein incorporated by reference. The predicted size of human IL-21R is about 529 amino acids. IL-21R shows high sequence homology to IL-2 receptor β chain and IL-4 receptor α chain (Ozaki et al. (2000) *Proc. Natl. Acad. Sci*. USA 97:11439-11444). The human and mouse IL-21R amino acid sequences share about 62% identity. Upon ligand binding, IL-21R associates with the common gamma cytokine receptor chain (γc) that is shared by receptors for IL-2, IL-3, IL-4, IL-7, IL-9, IL-13 and IL-15 (Ozaki et al. (2000) supra; Asao et al. (2001) *J. Immunol.* 167:1-5).

IL-21R is expressed primarily in lymphoid tissues, such as B cells, T cells, and natural killer (NK) cells. The widespread lymphoid distribution of IL-21R suggests that IL-21 may play a role in immune regulation. Indeed, in vitro studies have shown that IL-21 significantly modulates the function of B cells, CD4+ and CD8+ T cells, and NK cells (Parrish-Novak et al. (2000) supra; Kasaian, M. T. et al. (2002) *Immunity.* 16:559-569). IL-21 and IL-21R have also been shown to be important for modulating the activity of macrophages, and synovial cells. For example, IL-21 augments the proliferation of B cells stimulated with anti-CD40 antibody, and suppresses the proliferation of B cells stimulated with anti-IgM and IL-4. IL-21 augments the proliferation and cytolytic activity of T cells and human NK cells. IL-21 also mediates the expression of cytokines, chemokines, or combination thereof, secreted by T cells, NK cells, macrophages, and synovial cells. Because of the dependence of B cells, T cells, NK cells, macrophages, and synovial cells on IL-21, altering IL-21 binding to IL-21R may affect certain immune responses. Such a manipulation provides a means for treating immune system disorders, such as autoimmune disease disorders, inflammatory disorders, allergies, transplant rejection, cancer, immune deficiency, and other disorders.

SUMMARY OF THE INVENTION

The present application provides antibodies that bind the IL-21 receptor ("IL-21R"), in particular, the human IL-21 receptor, with high affinity and specificity. In one embodiment, an antibody reduces, inhibits or antagonizes IL-21R activity. Such antibodies can be used to regulate immune responses or immune cell-associated disorders by antagonizing IL-21R activity. In other embodiments, an anti-IL-21R antibody can be used diagnostically, or as a targeting antibody to deliver a therapeutic or a cytotoxic agent to an IL-21R-expressing cell. Thus, anti-IL-21R antibodies of the invention are useful in diagnosing and treating immune cell-associated pathologies (e.g., pathologies associated with activity of at least one of: T cells (CD8+, CD4+ T cells), NK cells, B cells, macrophages and megakaryocytes, including transplant rejection and autoimmune disorders).

Accordingly, in one aspect, the invention features an isolated antibody that binds to IL-21R, in particular, human IL-21R. An anti-IL-21R antibody may have at least one of the following characteristics: (1) it is a monoclonal or single specificity antibody; (2) it is a human or in vitro generated antibody; (3) it binds to IL-21R, in particular, the extracellular domain of human IL-21R, with an affinity constant ($K_a$) of at least $10^6$ $M^{-1}$, and (4) it inhibits binding of IL-21 to IL-21R with an $IC_{50}$ of 10 nM or less as an IgG, for example, as measured by a cell-based assay described in Example 9, or it inhibits the binding of an antibody to IL-21R with an $IC_{50}$ of 10 nM or less, for example, as measured by an epitope binding assay described in Example 11.

Nonlimiting illustrative embodiments of the antibodies of the invention are referred to herein as "MUF", "MUF-germline", "MU11", "18G4", "18A5", "19F5", "CP5G2" and "R18." The antibodies of the invention may specifically bind to the extracellular domain of an IL-21R, e.g., about amino acid 20 to 235 of SEQ ID NO:43 (human IL-21R), or a sequence that is at least 85%, 90%, 95%, 96%, 97%, 98%, 99% or more identical thereto. In other embodiments, antibodies specifically bind to a fragment of an IL-21R, e.g., a fragment of at least 10, 20, 50, 75, 100, 150, or 200 amino acids contiguous to the amino acid sequence set forth in SEQ ID NO:43, or a sequence that is at least 85%, 90%, 95%, 96%, 97%, 98%, 99% or more identical thereto. In other embodiments, an antibody binds to the extracellular domain of an IL-21R and competitively inhibits binding of "MUF", "MUF-germline", "MU11", "18G4", "18A5", "19F5", "CP5G2" or "R18" to its target epitope. In yet other embodiments, an antibody binds to the extracellular domain of an IL-21R and competitively inhibits binding of IL-21 to IL-21R. Such an inhibition of binding of IL-21 to its receptor by an antibody of the invention can be measured by one or more assays provided herein.

In one embodiment, an antibody of the present invention includes a $V_H$ domain, a $V_L$ domain, or a combination thereof, of the $scF_v$ fragment of "MUF", "MUF-germline", "MU11", "18G4", "18A5", "19F5", "CP5G2" or "R18". For example, an antibody includes a $V_H$ and/or a $V_L$ domain having amino acid sequence as set forth in Tables 1A and 1B (SEQ ID NO:1, 19, 47, 65, 83, 101, 119 or 137 for $V_H$ and SEQ ID NO:2, 20, 48, 66, 84, 102, 120 or 138 for $V_L$), or a sequence substantially identical thereto (e.g., a sequence at least about 85%, 90%, 95%, 96%, 97%, 98%, 99% or more identical thereto, or which differs by no more than 1, 2, 5, 10 or 15 amino acid residues from SEQ ID NO:1, 2, 19, 20, 47, 48, 65, 66, 83, 84, 101, 102, 119, 120, 137 or 138). In another embodiment, the antibody includes a $V_H$ and/or $V_L$ domain encoded by a nucleic acid having a nucleotide sequence as set forth in Tables 1A and 1B (SEQ ID NO:10, 28, 56, 74, 92, 110, 128, or 146 for $V_H$ and SEQ ID NO:11, 29, 57, 75, 93, 111, 129, or 147 for $V_L$), or a sequence substantially identical thereto (e.g., a sequence at least about 85%, 90%, 95%, 96%, 97%, 98%, 99% or more identical thereto, or which differs by no more than 3, 6, 15, 30 or 45 nucleotides from SEQ ID NO:10, 11, 28, 29, 56, 57, 74, 75, 92, 93, 110, 111, 128, 129, 146 or 147). Typically, the $V_H$ and $V_L$ domains in a scFv fragment are linked by a linker sequence.

In other embodiments, the antibody includes an scFv domain having an amino acid sequence as set forth in Tables 1A and 1B (SEQ ID NO:3, 21, 49, 67, 85, 103, 121, or 139) or a sequence substantially identical thereto (e.g., a sequence at least about 85%, 90%, 95%, 96%, 97%, 98%, 99% or more identical thereto, or which differs by no more than 1, 2, 5, 10, 15, 20, 30 or 35 amino acid residues from SEQ ID NO:3, 21, 49, 67, 85, 103, 121, or 139). In another embodiment, the antibody include an scFv domain encoded by a nucleic acid having a nucleotide sequence as set forth in Tables 1A and 1B (SEQ ID NO:12, 30, 58, 76, 94, 112, 130, or 148), or a sequence substantially identical thereto (e.g., a sequence at least about 85%, 90%, 95%, 96%, 97%, 98%, 99% or more identical thereto, or which differs by no more than 3, 6, 15, 30, 45, 60, 90 or 105 nucleotides from SEQ ID NO:12, 30, 58, 76, 94, 112, 130, or 148). In yet other embodiments, the antibody comprises at least one complementarity determining region (CDR) of these $V_H$ and $V_L$ domains. For example, the antibody can include one, two, or three CDR's of the $V_H$ domain (i.e., H1, H2, and H3) having an amino acid sequence as set forth in Tables 1A and 1B (SEQ ID NO:4, 5, 6, 22, 23, 24, 50, 51, 52, 68, 69, 70, 86, 87, 88, 104, 105, 106, 122, 123, 124, 140, 141, or 142), or a sequence substantially homologous thereto (e.g., a sequence at least about 85%, 90%, 95%, 96%, 97%, 98%, 99% or more identical thereto). In some embodiments, a sequence that is substantially homologous to the H1, H2, or H3 amino acid sequences set forth in SEQ ID NO:4, 5, 6, 22, 23, 24, 50, 51, 52, 68, 69, 70, 86, 87, 88, 104, 105, 106, 122, 123, 124, 140, 141, or 142 includes one or more amino acid substitutions, for example, one or more conservative amino acid substitutions. In another embodiment, the antibody can include one, two, or three CDR's of the $V_L$ domain (i.e., L1, L2 and L3) having an amino acid sequence as set forth in Tables 1A and 1B (SEQ ID NO:7, 8, 9, 25, 26, 27, 53, 54, 55, 71, 72, 73, 89, 90, 91, 107, 108, 109, 125, 126, 127, 143, 144, or 145), or a sequence substantially identical thereto (e.g., a sequence at least about 85%, 90%, 95%, 96%, 97%, 98%, 99% or more identical thereto). In some embodiments, a sequence that is substantially homologous to the L1, L2, or L3 amino acid sequences set forth in SEQ ID NO:7, 8, 9, 25, 26, 27, 53, 54, 55, 71, 72, 73, 89, 90, 91, 107, 108, 109, 125, 126, 127, 143, 144 or 145 includes one or more amino acid substitutions, for example, one or more conservative amino acid substitutions.

In a still further embodiment, an antibody comprises a CDR of the $V_H$ domain of MUF, MU11, MUF-germline, 18G4, 18A5, 19F5, CP5G2, or R18, having the amino acid sequence set forth in Tables 1A and 1B (SEQ ID NO:6, 24, 52, 70, 88, 106, 124, or 142), or a sequence substantially identical thereto (e.g., a sequence at least about 85%, 90%, 95%, 96%, 97%, 98%, 99% or more identical thereto), which includes one or more amino acid substitutions, for example, one or more conservative amino acid substitutions. An antibody according to the invention may either comprise a heavy chain variable region including a single CDR, such as H3, or any combinations of H1, H2 and H3. For example, in some embodiments, an antibody may include CDR (H3) in combination with CDR2 (H2). In other embodiments, an antibody may include a CDR3 (H3) in combination with a CDR1 (H1), or a combination of H1 and H2 CDRs. However, preferably, an antibody includes a heavy chain variable region comprising a CDR3 (H3), as set forth in any of SEQ ID NO:6, 24, 52, 70, 88, 106, 124, 142, and amino acid substitutions thereof, for example, one or more conservative amino acid substitutions, either alone or in combination with one or both of H1 and H2.

Similarly, in some embodiments, an antibody comprises a CDR of the $V_L$ domain of MUF, MU11, MUF-germline, 18G4, 18A5, 19F5, CP5G2, or R18, e.g., an L3 CDR having the amino acid sequence as set forth in Tables 1A and 1B (SEQ ID NO:9, 27, 55, 73, 91, 109, 127, or 145), or a sequence substantially identical thereto (e.g., a sequence at least about 85%, 90%, 95%, 96%, 97%, 98%, 99% or more identical thereto), which includes one or more amino acid substitutions, for example, one or more conservative amino acid substitutions. An antibody according to the invention may either comprise a light chain variable region including a single CDR, such as L3, or any combinations of L1, L2 and L3. For example, in some embodiments, an antibody may include an L3 in combination with an L2. In other embodiments, an antibody may include an L3 in combination with an L1. In yet, another embodiment, an antibody may include a combination of L1 and L2 CDRs. However, preferably, an antibody includes a light chain variable region comprising an L3, as set forth in any of SEQ ID NO:9, 27, 55, 73, 91, 109, 127, 145 and amino acid substitutions thereof, for example, one or more conservative amino acid substitutions thereof, either alone or in combination with one or both of L1 and L2.

In some embodiments, an antibody of the invention competes for IL-21R binding with an antibody which includes a $V_H$ domain which is at least 95%, 96%, 97%, 98%, 99%, or more than 99% identical to an amino acid sequence set forth in SEQ ID NO:1, 19, 47, 65, 83, 101, 119 or 137, and a $V_L$ domain which is at least 95%, 96%, 97%, 98%, 99%, or more than 99% identical to an amino acid sequence set forth in SEQ ID NO:2, 20, 48, 66, 84, 102, 120 or 138. In certain embodiments, an antibody competes for IL-21R binding with an antibody that includes a heavy chain variable region comprising at least one heavy chain CDR chosen from SEQ ID NO:6, 24, 52, 70, 88, 106, 124, 142 and amino acid substitutions thereof, for example, one or more conservative amino acid substitutions thereof. In certain embodiments, an antibody according to the invention competes for IL-21R binding, for example, human IL-21R binding, with an antibody that includes a light chain variable region comprising at least one light chain CDR chosen from SEQ ID NO:9, 27, 55, 73, 91, 109, 127, 145 and amino acid substitutions thereof, for example, one or more conservative amino acid substitutions thereof. An antibody with which an antibody of the invention competes for binding to IL-21R, for example, human IL-21R, may include both a heavy chain CDR chosen from SEQ ID NO:6, 24, 52, 70, 88, 106, 124, and 142, and a light chain CDR chosen from SEQ ID NO:9, 27, 55, 73, 91, 109, 127, and 145. In some embodiments, an antibody according to the invention includes more than one heavy chain CDR chosen from SEQ ID NO:4, 5, 6 for MUF; SEQ ID NO:22, 23, 24 for MU11; SEQ ID NO:50, 51, 52 for 18G4; SEQ ID NO:68, 69, 70 for 18A5, SEQ ID NO:86, 87, 88 for MUF-germline; SEQ ID NO:104, 105, 106 for 19F5; SEQ ID NO:122, 123, 124 for CP5G2; and SEQ ID NO:140, 141, 142 for R18, and/or one or more light chain variable region CDR chosen from SEQ ID NO:7, 8, 9 for MUF; SEQ ID NO:25, 26, 27 for MU11; SEQ ID NO:53, 54, 55 for 18G4; SEQ ID NO:71, 72, 73 for 18A5; SEQ ID NO:89, 90, 91 for MUF-germline; SEQ ID NO:107, 108, 109 for 19F5; SEQ ID NO:125, 126, 127 for CP5G2; and SEQ ID NO:143, 144, 145 for R18.

In yet other embodiments, an antibody according to the invention competes with IL-21, for example, human IL-21, for binding to IL-21R, for example, human IL-21R.

An antibody of the invention can be full-length (e.g., include at least one complete heavy chain and at least one complete light chain) or can include only an antigen-binding fragment (e.g., a Fab, $F(ab')_2$, Fv or a single chain Fv fragment (scFv)). An antibody can include a constant region, or a portion thereof, chosen from any of: the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. The light chain constant region can be chosen from kappa or lambda. An antibody may be an IgG, or it may also be $IgG_{1\kappa}$ or $IgG_{1\lambda}$.

An anti-IL-21R antibody described herein can be derivatized or linked to another functional molecule (such as another peptide or protein (e.g., a Fab fragment)). For example, an antibody of the invention can be functionally linked (e.g., by chemical coupling, genetic fusion, non-covalent association or otherwise) to at least one other molecular entity, such as another antibody (e.g., a bispecific or a multispecific antibody), toxin, radioisotope, cytotoxic or cytostatic agent, among others.

In another aspect, the invention features a pharmaceutical composition containing at least one anti-IL-21R antibody and a pharmaceutically acceptable carrier. The pharmaceutical composition can further include a combination of at least one anti-IL-21R antibody and at least one therapeutic agent (e.g., cytokine and growth factor inhibitors, immunosuppressants, anti-inflammatory agents, metabolic inhibitors, enzyme inhibitors, cytotoxic agents, cytostatic agents, or combinations thereof, as described in more detail herein). Combinations of the anti-IL-21R antibody and a therapeutic agent are also within the scope of the invention. The compositions and combinations of the invention can be used to regulate IL-21-dependent immune cells, such as B cells, T cells, NK cells, macrophages, and synovial cells.

In another aspect, the invention features a method of treating a subject with an immune cell-associated disease. The method includes administering to the subject an anti-IL-21R antibody in an amount sufficient to inhibit at least one IL-21R activity of immune cells, thereby treating the immune cell-associated disease.

The anti-IL-21R antibody can be administered to the subject, alone or in combination, with other therapeutic agents as described herein. The subject may be a mammal suffering from an immune cell-associated pathology (e.g., pathology associated with the aberrant activity of at least one of: T cells, NK cells, B cells, macrophages and megakaryocytes). The subject may be human. For example, the method can be used to treat a subject with an immune cell-associated disorder such as transplant rejection and autoimmune disease. Autoimmune diseases may include diabetes mellitus (type I), arthritis (including rheumatoid arthritis, juvenile rheumatoid arthritis, osteoarthritis, psoriatic arthritis, and ankylosing spondylitis), multiple sclerosis, myasthenia gravis, vasculitis, systemic lupus erythematosis, autoimmune thyroiditis, dermatitis (including atopic dermatitis and eczematous dermatitis), psoriasis, scleroderma, asthma, allergy, inflammatory bowel disease (IBD), and Crohn's disease. Treatment of an arthritic disorder (e.g., a disorder chosen from at least one of rheumatoid arthritis, juvenile rheumatoid arthritis, osteoarthritis, psoriatic arthritis, and ankylosing spondylitis) using the anti-IL-21R antibodies of the present invention is an embodiment of the invention.

In another aspect, the invention provides a method for detecting the presence of IL-21R in a sample, in vitro. Samples may include biological samples such as serum, plasma, tissue and biopsy. The subject method can be used to diagnose a disorder, such as an immune cell-associated disorder as described herein. The method includes: (1) contacting the sample or a control sample with an anti-IL-21R antibody, and (2) detecting formation of a complex between the anti-IL-21R antibody and the sample or the control sample, wherein a statistically significant change in the formation of the complex in the sample relative to a control sample, is indicative of the presence of the IL-21R in the sample.

In another aspect, the invention provides a method for detecting the presence of IL-21R in vivo (e.g., in vivo imaging in a subject). The method can be used to diagnose a disorder, e.g., an immune cell-associated disorder as described herein. The method includes: (1) administering an anti-IL-21R antibody to a subject or a control subject under conditions that allow binding of the antibody to IL-21R, and (2) detecting formation of a complex between the antibody and IL-21R, wherein a statistically significant change in the formation of the complex in the subject relative to a control, e.g., a control subject, is indicative of the presence of IL-21R.

An antibody according to the invention may be directly or indirectly labeled with a detectable substance to facilitate detection of the bound or unbound antibody. Suitable detectable substances include various enzymes, prosthetic groups, fluorescent materials, luminescent materials and radioactive materials.

In another aspect, the invention provides a method for delivering or targeting an agent, e.g., a therapeutic or a cytotoxic agent, to an IL-21R-expressing cell in vivo. The method includes administering an anti-IL-21R antibody to a subject under conditions that allow binding of the antibody to IL-21R. The antibody may be coupled to a second therapeutic moiety, such as a toxin.

The disclosure provides nucleic acid sequences from the $V_H$ and $V_L$ domains of MUF, MUF-germline, MU11, 18G4, 18A5, 19F5, CP5G2 and R18. Also provided are nucleic acid sequences that comprise at least one CDR from MUF, MUF-germline, MU11, 18G4, 18A5, 19F5, CP5G2 and R18. The disclosure also provides vectors and host cells comprising such nucleic acids.

The disclosure further provides methods of producing new $V_H$ and $V_L$ domains and functional antibodies comprising all or a portion of such domains derived from the $V_H$ or $V_L$ domains of MUF, MUF-germline, MU11, 18G4, 18A5, 19F5, CP5G2 or R18.

Additional aspects of the disclosure will be set forth in part in the description, and in part will be obvious from the description, or may be learned by practicing the invention. The invention is set forth and particularly pointed out in the claims, and the disclosure should not be construed as limiting the scope of the claims. The following detailed description includes exemplary representations of various embodiments of the invention, which are not restrictive of the invention as claimed. The accompanying figures constitute a part of this specification and, together with the description, serve only to illustrate embodiments and not limit the invention.

DETAILED DESCRIPTION

Definitions

Figure 1A:
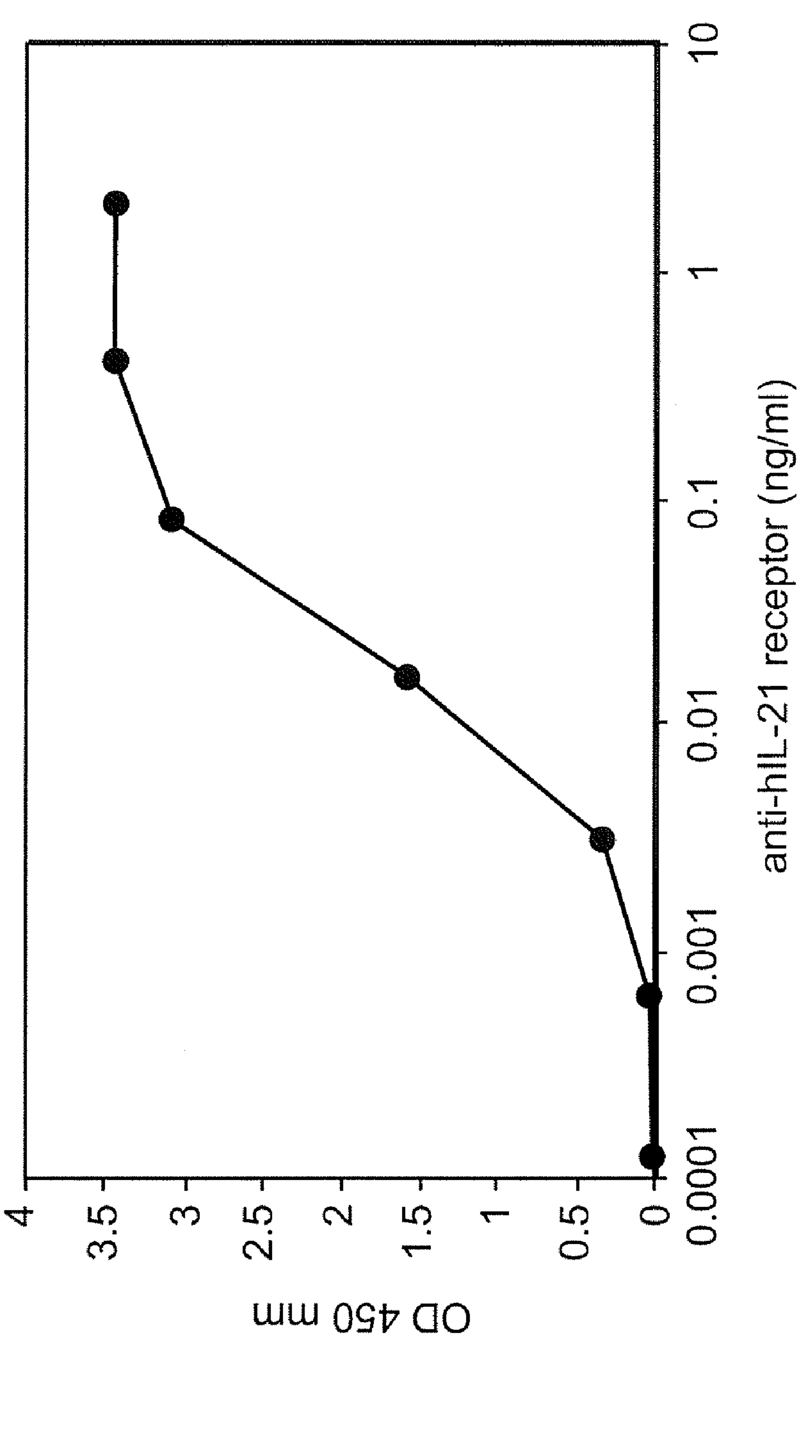
FIG. 1A depicts the result of an ELISA which shows that MU11 specifically bind to human IL-21R.

In order that the present invention may be more readily understood, certain terms are first defined. Additional definitions are set forth throughout the detailed description.

The "antibody" refers to an immunoglobulin or fragment thereof, and encompasses any polypeptide comprising an antigen-binding site. The term is not limited to polyclonal, monoclonal, monospecific, polyspecific, non-specific, humanized, human, single-chain, chimeric, synthetic, recombinant, hybrid, mutated, grafted, and in vitro generated antibodies. Unless preceded by the word "intact," the term "antibody" includes antibody fragments such as Fab, $F(ab')_2$, Fv, scFv, Fd, dAb, and other antibody fragments that retain antigen-binding function. Typically, such fragments would comprise an antigen-binding domain.

The terms "antigen-binding domain" and "antigen-binding fragment" refer to a part of an antibody molecule that comprises amino acids responsible for the specific binding between antibody and antigen. The part of the antigen that is specifically recognized and bound by the antibody is referred to as the "epitope." An antigen-binding domain may comprise an antibody light chain variable region ($V_L$) and an antibody heavy chain variable region ($V_H$); however, it does not have to comprise both. Fd fragments, for example, have two $V_H$ regions and often retain some antigen-binding function of the intact antigen-binding domain. Examples of antigen-binding fragments of an antibody include (1) a Fab fragment, a monovalent fragment consisting of the $V_L$, $V_H$, $C_L$ and $C_H1$ domains; (2) a $F(ab')_2$ fragment, a bivalent fragment comprising two Fab fragments linked by a disulfide bridge at the hinge region; (3) a Fd fragment consisting of the two $V_H$ and $C_H1$ domains; (4) a Fv fragment consisting of the $V_L$ and $V_H$ domains of a single arm of an antibody, (5) a dAb fragment (Ward et al., (1989) *Nature* 341:544-546), which consists of a $V_H$ domain; and (6) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). These antibody fragments are obtained using conventional techniques known to those with skill in the art, and the fragments are screened for utility in the same manner as are intact antibodies.

The term "effective amount" refers to a dosage or amount that is sufficient to regulate IL-21R activity to ameliorate clinical symptoms or achieve a desired biological outcome, e.g., decreased T cell and/or B cell activity, suppression of autoimmunity, suppression of transplant rejection, etc.

The term "human antibody" includes antibodies having variable and constant regions corresponding substantially to human germline immunoglobulin sequences as described by Kabat et al. (See Kabat, et al. (1991) Sequences of Proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

The term "IL-21R activity" refers to at least one cellular process initiated or interrupted as a result of IL-21 binding to IL-21R on the cell. IL-21R activities include at least one of, but are not limited to: (1) binding IL-21 (e.g., human IL-21); (2) associating with signal transduction molecules (e.g., γc and/or JAK-1); (3) stimulating phosphorylation of STAT proteins (e.g., STAT5, STAT3, or combination thereof); (4) activating STAT proteins; and (5) modulating (e.g., increasing or decreasing) proliferation, differentiation, effector cell function, cytolytic activity, cytokine secretion, survival, or combinations thereof, of immune cells. Immune cells may include CD8+ and CD4+ T cells, NK cells, B cells, macrophages, and megakaryocytes. IL-21R activity can be determined in vitro, for example, using T cell proliferation assays as described in Examples 8 and 9. IL-21R activity can also be determined in vivo, for example, by scoring progression of an immune response or disorder as described in Example 12.

The phrase "inhibit" or "antagonize" IL-21R activity and its cognates refer to a reduction, inhibition, or otherwise diminution of at least one activity of IL-21R due to binding an anti-IL-21R antibody, wherein the reduction is relative to the activity of IL-21R in the absence of the same antibody. The activity can be measured as described in Examples 7, 8, 9 and 11. Inhibition or antagonism does not necessarily indicate a total elimination of the IL-21R polypeptide biological activity. A reduction in activity may be about 10%, 20%, 30%, 40%, 50%, 60%, 70%, 80%, 90%, or more.

The term "interleukin-21 receptor" or "IL-21R" refers to a class I cytokine receptor, also known as NILR (WO 01/85792; Parrish-Novak et al. (2000) *Nature* 408:57-63; Ozaki et al. (2000) *Proc. Natl. Acad. Sci. USA* 97:11439-114444). Upon ligand binding, IL-21R interacts with a common γ cytokine receptor chain (γc) (Asao et al. (2001) *J. Immunol.* 167:1-5), and induces the phosphorylation of STAT1 and STAT3 (Asao et al. (2001) supra or STAT5 (Ozaki et al. (2000) supra). IL-21R shows widespread lymphoid tissue distribution. The term "IL-21R" refers to a receptor (which may be mammalian) which is capable of binding to IL-21, and has at least one of the following features: (1) an amino acid sequence of a naturally occurring mammalian IL-21R polypeptide or a fragment thereof, e.g., an amino acid sequence shown as SEQ ID NO:43 (human) or SEQ ID NO:45 (murine) or a fragment thereof; (2) an amino acid sequence substantially identical to, e.g., at least 85%, 90%, 95%, 96%, 97%, 98%, 99% identical to, an amino acid sequence shown as SEQ ID NO:43 (human) or SEQ ID NO:45 (murine) or a fragment thereof; (3) an amino acid sequence which is encoded by a naturally occurring mammalian IL-21R nucleotide sequence or a fragment thereof (e.g., SEQ ID NO:44 (human) or SEQ ID NO:46 (murine) or a fragment thereof); (4) an amino acid sequence encoded by a nucleotide sequence which is substantially identical to, e.g., at least 85%, 90%, 95%, 96%, 97%, 98%, 99% identical to, a nucleotide sequence shown as SEQ ID NO:44 (human) or SEQ ID NO:46 (murine) or a fragment thereof; (5) an amino acid sequence encoded by a nucleotide sequence degenerate to a naturally occurring IL-21R nucleotide sequence or a fragment thereof, e.g., SEQ ID NO:44 (human) or SEQ ID NO:46 (murine) or a fragment thereof; or (6) a nucleotide sequence that hybridizes to one of the foregoing nucleotide sequences under stringent conditions, e.g., highly stringent conditions. The IL-21R may bind to IL-21 of mammalian origin, e.g., human or mouse. (Parrish-Novak et al. (2000) supra).

As used herein, "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term excludes sequences generated by genomic rearrangement in an immune cell.

The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The nucleotide sequence and the predicted amino acid sequence of human IL-21R are shown in SEQ ID NO:44 and SEQ ID NO:43, respectively. Analysis of the human IL-21R amino acid sequence (SEQ ID NO:43) revealed the following structural features: a leader sequence (about amino acids 1-19 of SEQ ID NO:43); a WSXWS motif (about amino acids 213-217 of SEQ ID NO:43); a transmembrane domain (about amino acids 236-252 of SEQ ID NO:43); an extracellular domain (about amino acids 1-235 of SEQ ID NO:43 and about 20-235 of the mature IL-21R sequence); and an intracellular domain from about amino acids 253-538 of SEQ ID NO:43. The mature human IL-21R is believed to have the sequence of amino acids 20-538 of SEQ ID NO:43.

The term "repertoire" refers to a genetically diverse collection of nucleotide sequences derived wholly or partially from sequences encoding immunoglobulins. The sequences may be generated by rearrangement in vivo of the V, D, and J segments of heavy chains, and the V and J segments of light chains. Alternatively, the sequences can be generated from a cell in response to which rearrangement occurs, e.g., in vitro stimulation. Alternatively, part or all of the sequences may be obtained by DNA splicing, nucleotide synthesis, mutagenesis, and other methods, see, e.g., U.S. Pat. No. 5,565,332.

The terms "specific binding", "selective binding" and "selectively binds" refer to two molecules forming a complex that is relatively stable under physiologic conditions. Selective binding is characterized by a high affinity and a low to moderate capacity as distinguished from nonspecific binding which usually has a low affinity with a moderate to high capacity. Typically, binding is considered specific or selective when the affinity constant $K_a$ is higher than $10^6 M^{-1}$. If necessary, nonspecific binding can be reduced without substantially affecting selective binding by varying the binding conditions. The appropriate binding conditions, such as concentration of antibodies, ionic strength of the solution, temperature, time allowed for binding, concentration of a blocking agent (e.g., serum albumin, milk casein), etc., may be optimized by a skilled artisan using routine techniques. Illustrative conditions are set forth in Examples 1-11, but other conditions known to the person of ordinary skill in the art fall within the scope of this invention.

As used herein, the term "stringent" describes conditions for hybridization and washing. Stringent conditions are known to those skilled in the art and can be found in *Current Protocols in Molecular Biology*, John Wiley & Sons, N.Y. (1989), 6.3.1-6.3.6. Aqueous and nonaqueous methods are described in that reference and either can be used. One example of stringent hybridization conditions is hybridization in 6× sodium chloride/sodium citrate (SSC) at about 45° C., followed by at least one wash in 0.2×SSC, 0.1% SDS at 50° C. A second example of stringent hybridization conditions is hybridization in 6×SSC at about 45° C., followed by at least one wash in 0.2×SSC, 0.1% SDS at 55° C. Another example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. High stringent conditions include hybridization in 0.5 M sodium phosphate, 7% SDS at 65° C., followed by at least one wash at 0.2×SSC, 1% SDS at 65° C.

The phrase "substantially as set out," "substantially identical" or "substantially homologous" means that the relevant amino acid or nucleotide sequence (e.g., CDR(s), $V_H$, or $V_L$ domain) will be identical to or have insubstantial differences (through conserved amino acid substitutions) in comparison to the sequences which are set out. Insubstantial differences include minor amino acid changes, such as 1 or 2 substitutions in a 5 amino acid sequence of a specified region. In the case of antibodies, the second antibody has the same specificity and has at least 50% of the affinity of the same.

Sequences substantially identical or homologous (e.g., at least about 85% sequence identity) to the sequences disclosed herein are also part of this application. In some embodiment, the sequence identity can be about 90%, 91%, 92%, 93%, 94%, 95%, 96%, 97%, 98%, 99% or higher. Alternatively, substantial identity or homology exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

The percent identity can be determined by standard alignment algorithms, for example, the Basic Local Alignment Tool (BLAST) described by Altshul et al. ((1990) J. Mol. Biol., 215: 403-410); the algorithm of Needleman et al. ((1970) J. Mol. Biol., 48: 444-453); or the algorithm of Meyers et al. ((1988) Comput. Appl. Biosci., 4: 11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The term “therapeutic agent” is a substance that treats or assists in treating a medical disorder. As used herein, a therapeutic agent refers to a substance, when administered to a subject with anti-IL-21R antibody, provides a better treatment compared to administration of the therapeutic agent or anti-IL-21R antibody alone. These therapeutic agents may include, but are not limited to, substances that modulate immune cells or immune responses in a manner that complements the IL-21R activity of anti-IL-21R antibodies. Non-limiting examples and uses of therapeutic agents are described herein.

As used herein, a “therapeutically effective amount” of an anti-IL-21R antibody refers to an amount of an antibody which is effective, upon single or multiple dose administration to a subject (such as a human patient) at treating, preventing, curing, delaying, reducing the severity of, ameliorating at least one symptom of a disorder or recurring disorder, or prolonging the survival of the subject beyond that expected in the absence of such treatment.

The term “treatment” refers to a therapeutic or preventative measure. The treatment may be administered to a subject having a medical disorder or who ultimately may acquire the disorder, in order to prevent, cure, delay, reduce the severity of, or ameliorate one or more symptoms of a disorder or recurring disorder, or in order to prolong the survival of a subject beyond that expected in the absence of such treatment.

Anti-IL-21R Antibodies

The disclosure provides novel anti-IL-21R antibodies that comprise novel antigen-binding fragments.

In general, antibodies can be made, for example, using traditional hybridoma techniques (Kohler and Milstein (1975) Nature, 256: 495-499), recombinant DNA methods (U.S. Pat. No. 4,816,567), or phage display using antibody libraries (Clackson et al. (1991) Nature, 352: 624-628; Marks et al. (1991) J. Mol. Biol., 222: 581-597). For additional antibody production techniques, see Antibodies: A Laboratory Manual, eds. Harlow et al., Cold Spring Harbor Laboratory, 1988. The present invention is not limited to any particular source, method of production, or other special characteristics of an antibody.

Intact antibodies are immunoglobulins (Ig), and they typically are tetrameric glycosylated proteins composed of two light chains (~25 kDa each) and two heavy chains (~50 kDa each). Light chains are classified into two isotypes (λ and κ) and heavy chains are classified into five isotypes (A, D, E, G, and M). Some heavy chain isotypes are further divided into isotype subclasses, e.g., $IgG_1$, $IgG_2$, $IgG_3$, and $IgG_4$.

The domain and three dimensional structures of different antibodies are known in the art (Harlow et al., supra). In brief, the light chain is composed of a constant domain ($C_L$) and an N-terminal variable domain ($V_L$). The heavy chain is composed of three or four constant domains ($C_H$), a hinge region, and a N-terminal variable domain ($V_H$). The $C_H$ adjacent to the $V_H$ domain is designated $C_H1$. The $V_H$ and $V_L$ domains contain four regions of conserved sequence called framework (FR) regions (FR1, FR2, FR3, and FR4), which form a scaffold for three regions of hypervariable sequence called complementarity determining regions (CDR). The CDRs (CDR1, CDR2, and CDR3) contain most of the antibody amino acids that specifically binds antigen. Heavy chain CDRs are denoted H1, H2, and H3, while light chain CDRs are denoted L1, L2, and L3.

The Fab fragment (Fragment antigen-binding) consists of $V_H$-$C_H1$ and $V_L$-$C_L$ domains covalently linked by a disulfide bond between the constant regions. The $F_v$ fragment is smaller and consists of $V_H$ and $V_L$ domains non-covalently linked. To overcome the tendency of non-covalently domains to dissociate, a single chain $F_v$ fragment ($scF_v$) can be constructed. The $scF_v$ contains a flexible polypeptide that links the (1) C-terminus of $V_H$ to the N-terminus of $V_L$, or the (2) C-terminus of $V_L$ to the N-terminus of $V_H$. A 15-mer $(Gly_4Ser)_3$ peptide may be used as a linker, but other linkers are known in the art.

Antibody diversity is created by use of multiple germline genes encoding variable regions and a variety of somatic events. The somatic events include recombination of variable gene segments and diversity (D) and joining (J) gene segments to make a complete $V_H$ region and the recombination of variable and joining gene segments to make a complete $V_L$ region. CDR3 (H3) is the greatest source of molecular diversity within an antibody sequence. H3, for example, can be as short as two amino acid residues or greater than 26. The smallest antigen-binding fragment is the Fv, which consists of the $V_H$ and the $V_L$ domains.

Antibodies and compositions having identical or similar CDR sequence to those disclosed herein are not likely to have been independently generated. The sequence of antibody genes after assembly and somatic mutation is highly varied, and these varied genes are estimated to encode $10^{10}$ different antibody molecules (Immunoglobulin Genes, 2nd ed., eds. Jonio et al., Academic Press, San Diego, Calif., 1995).

The present disclosure provides novel CDRs derived from human immunoglobulin gene libraries. The structure for carrying a CDR is generally an antibody heavy or light chain or portion thereof, where the CDR is located to a naturally occurring CDR region. The structures and locations of variable domains may be determined as described in Kabat et al., Sequences of Proteins of Immunological Interest, No. 91-3242, National Institutes of Health Publications, Bethesda, Md. (1991).

DNA and amino acid (AA) sequences of illustrative embodiments of he anti-IL-21R antibodies of this invention, including their $scF_v$ fragments, $V_H$ and $V_L$ domains, and CDRs, are set forth in the Sequence Listing and enumerated in Tables 1A and 1B. Specific embodiments of the antibodies are identified as MUF, MUF-germline, MU11, 18G4, 18A5, 19F5, CP5G2 and R18. The CDR positions in the $V_H$ and $V_L$ domains of the antibodies are listed in Table 2.

TABLE 1A

| AA and DNA Sequences of $V_H$ and $V_L$ Domains, $F_V$, and CDRs | | | | | |
|---|---|---|---|---|---|
| REGION | TYPE | MUF | MU11 | 18G4 | 18A5 |
| $V_H$ | AA | SEQ ID NO: 1 | SEQ ID NO: 19 | SEQ ID NO: 47 | SEQ ID NO: 65 |
| $V_L$ | AA | SEQ ID NO: 2 | SEQ ID NO: 20 | SEQ ID NO: 48 | SEQ ID NO: 66 |
| $scF_v$ | AA | SEQ ID NO: 3 | SEQ ID NO: 21 | SEQ ID NO: 49 | SEQ ID NO: 67 |
| H1 | AA | SEQ ID NO: 4 | SEQ ID NO: 22 | SEQ ID NO: 50 | SEQ ID NO: 68 |
| H2 | AA | SEQ ID NO: 5 | SEQ ID NO: 23 | SEQ ID NO: 51 | SEQ ID NO: 69 |
| H3 | AA | SEQ ID NO: 6 | SEQ ID NO: 24 | SEQ ID NO: 52 | SEQ ID NO: 70 |
| L1 | AA | SEQ ID NO: 7 | SEQ ID NO: 25 | SEQ ID NO: 53 | SEQ ID NO: 71 |
| L2 | AA | SEQ ID NO: 8 | SEQ ID NO: 26 | SEQ ID NO: 54 | SEQ ID NO: 72 |
| L3 | AA | SEQ ID NO: 9 | SEQ ID NO: 27 | SEQ ID NO: 55 | SEQ ID NO: 73 |
| $V_H$ | DNA | SEQ ID NO: 10 | SEQ ID NO: 28 | SEQ ID NO: 56 | SEQ ID NO: 74 |
| $V_L$ | DNA | SEQ ID NO: 11 | SEQ ID NO: 29 | SEQ ID NO: 57 | SEQ ID NO: 75 |
| $scF_v$ | DNA | SEQ ID NO: 12 | SEQ ID NO: 30 | SEQ ID NO: 58 | SEQ ID NO: 76 |
| H1 | DNA | SEQ ID NO: 13 | SEQ ID NO: 31 | SEQ ID NO: 59 | SEQ ID NO: 77 |
| H2 | DNA | SEQ ID NO: 14 | SEQ ID NO: 32 | SEQ ID NO: 60 | SEQ ID NO: 78 |
| H3 | DNA | SEQ ID NO: 15 | SEQ ID NO: 33 | SEQ ID NO: 61 | SEQ ID NO: 79 |
| L1 | DNA | SEQ ID NO: 16 | SEQ ID NO: 34 | SEQ ID NO: 62 | SEQ ID NO: 80 |
| L2 | DNA | SEQ ID NO: 17 | SEQ ID NO: 35 | SEQ ID NO: 63 | SEQ ID NO: 81 |
| L3 | DNA | SEQ ID NO: 18 | SEQ ID NO: 36 | SEQ ID NO: 64 | SEQ ID NO: 82 |

TABLE 1B

| AA and DNA Sequences of $V_H$ and $V_L$ Domains, $F_V$ and CDRs | | | | | |
|---|---|---|---|---|---|
| REGION | TYPE | MUF GERMLINE | 19F5 | CP5G2 | R18 |
| $V_H$ | AA | SEQ ID NO: 83 | SEQ ID NO: 101 | SEQ ID NO: 119 | SEQ ID NO: 137 |
| $V_L$ | AA | SEQ ID NO: 84 | SEQ ID NO: 102 | SEQ ID NO: 120 | SEQ ID NO: 138 |
| $scF_v$ | AA | SEQ ID NO: 85 | SEQ ID NO: 103 | SEQ ID NO: 121 | SEQ ID NO: 139 |
| H1 | AA | SEQ ID NO: 86 | SEQ ID NO: 104 | SEQ ID NO: 122 | SEQ ID NO: 140 |
| H2 | AA | SEQ ID NO: 87 | SEQ ID NO: 105 | SEQ ID NO: 123 | SEQ ID NO: 141 |
| H3 | AA | SEQ ID NO: 88 | SEQ ID NO: 106 | SEQ ID NO: 124 | SEQ ID NO: 142 |
| L1 | AA | SEQ ID NO: 89 | SEQ ID NO: 107 | SEQ ID NO: 125 | SEQ ID NO: 143 |
| L2 | AA | SEQ ID NO: 90 | SEQ ID NO: 108 | SEQ ID NO: 126 | SEQ ID NO: 144 |
| L3 | AA | SEQ ID NO: 91 | SEQ ID NO: 109 | SEQ ID NO: 127 | SEQ ID NO: 145 |
| $V_H$ | DNA | SEQ ID NO: 92 | SEQ ID NO: 110 | SEQ ID NO: 128 | SEQ ID NO: 146 |
| $V_L$ | DNA | SEQ ID NO: 93 | SEQ ID NO: 111 | SEQ ID NO: 129 | SEQ ID NO: 147 |
| $scF_v$ | DNA | SEQ ID NO: 94 | SEQ ID NO: 112 | SEQ ID NO: 130 | SEQ ID NO: 148 |
| H1 | DNA | SEQ ID NO: 95 | SEQ ID NO: 113 | SEQ ID NO: 131 | SEQ ID NO: 149 |
| H2 | DNA | SEQ ID NO: 96 | SEQ ID NO: 114 | SEQ ID NO: 132 | SEQ ID NO: 150 |
| H3 | DNA | SEQ ID NO: 97 | SEQ ID NO: 115 | SEQ ID NO: 133 | SEQ ID NO: 151 |
| L1 | DNA | SEQ ID NO: 98 | SEQ ID NO: 116 | SEQ ID NO: 134 | SEQ ID NO: 152 |
| L2 | DNA | SEQ ID NO: 99 | SEQ ID NO: 117 | SEQ ID NO: 135 | SEQ ID NO: 153 |
| L3 | DNA | SEQ ID NO: 100 | SEQ ID NO: 118 | SEQ ID NO: 136 | SEQ ID NO: 154 |

TABLE 2

| Positions of CDRs within AA Sequences | | | | |
|---|---|---|---|---|
| CDR | MUF (SEQ ID NO: 1) | MUF (SEQ ID NO: 2) | MU11 (SEQ ID NO: 21) | 18G4 (SEQ ID NO: 49) |
| H1 | 31-35 | | 31-35 | 31-35 |
| H2 | 50-66 | | 50-66 | 50-66 |
| H3 | 99-105 | | 99-106 | 99-105 |
| L1 | | 23-33 | 156-166 | 156-166 |
| L2 | | 49-55 | 182-188 | 182-188 |
| L3 | | 88-100 | 221-229 | 221-231 |
| CDR | 18A5 (SEQ ID NO: 67) | 19F5 (SEQ ID NO: 103) | CP5G2 (SEQ ID NO: 121) | R18 (SEQ ID NO: 139) |
| H1 | 31-36 | 31-35 | 31-35 | 31-35 |
| H2 | 51-66 | 50-66 | 50-66 | 50-66 |
| H3 | 99-107 | 99-109 | 99-107 | 99-110 |
| L1 | 158-168 | 160-170 | 158-168 | 161-171 |
| L2 | 184-190 | 186-192 | 184-190 | 187-193 |
| L3 | 223-234 | 225-236 | 223-234 | 226-236 |

TABLE 2-continued

| Positions of CDRs within AA Sequences | |
|---|---|
| CDR | MUF GERMLINE (SEQ ID NO: 85) |
| H1 | 31-35 |
| H2 | 50-66 |
| H3 | 99-105 |
| L1 | 156-166 |
| L2 | 182-188 |
| L3 | 221-233 |

Anti-IL-21R antibodies of this invention may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Constant regions are known in the art (see, for example, Kabat et al., Sequences of Proteins of Immunological Interest, No. 91-3242, National Institutes of Health Publications, Bethesda, Md. (1991).

In exemplary embodiments, MUF comprises heavy and light chain constant domains human $IgG_{1\lambda}$, and MU11 comprises the heavy and light chain constant domains of human $IgG_{1\kappa}$. In these antibodies, the sequences of the heavy chains outside of the $V_H$ domain are identical. The DNA and amino acid sequences for the C-terminal fragment of the λ light chain are set forth in SEQ ID NO:40 and SEQ ID NO:39, respectively. The DNA and amino acid sequences for the C-terminal fragment of the κ chain are set forth in SEQ ID NO:42 and SEQ ID NO:41, respectively. The DNA and amino acid sequences for the C-terminal fragment of $IgG_1$ heavy chain are set forth in SEQ ID NO:38 and SEQ ID NO:37, respectively.

Certain embodiments comprise a $V_H$ domain, a $V_L$ domain, or a combination thereof, of the $F_v$ fragment from MUF, MUF-germline, MU11, 18G4, 18A5, 19F5, CP5G2, or R18. Further embodiments comprise one, two, three, four, five or six complementarity determining regions (CDRs) from the $V_H$ and $V_L$ domains. Antibodies whose CDR sequences are set out in SEQ ID NO:1, 2, 3, 4, 5, 6, 7, 8, 9, 19, 20, 21, 22, 23, 24, 25, 26, 27, 47, 48, 49, 50, 51, 52, 53, 54, 55, 65, 66, 67, 68, 69, 70, 71, 72, 73, 83, 84, 85, 86, 87, 88, 89, 90, 91, 101, 102, 103, 104, 105, 106, 107, 108, 109, 119, 120, 121, 122, 123, 124, 125, 126, 127, 137, 138, 139, 140, 141, 142, 143, 144, or 145 are encompassed within the scope of this invention. For example, in one embodiment, an antibody comprises a CDR3 (H3) fragment of the $V_H$ domain of MUF, MUF-germline, MU11, 18G4, 18A5, 19F5, CP5G2, or R18.

In certain embodiments, the $V_H$ and/or $V_L$ domains may be germlined, i.e., the framework regions (FR) of these domains are mutated using conventional molecular biology techniques to match those produced by the germline cells. In other embodiments, the FR sequences remain diverged from the consensus germline sequences.

In one embodiment, the invention provides amino acid and nucleic acid sequences for the germlined MUF. Amino acid sequence for the $V_H$ domain of the germlined MUF is depicted in SEQ ID NO:83 and 85. Amino acid sequence for the $V_L$ domain of the germlined MUF is depicted in SEQ ID NO:84 and 85. Nucleic acid sequence for the germlined MUF $V_H$ domain is depicted in SEQ ID NO:92 and 94 and that for the germlined $V_L$ domain is depicted in SEQ ID NO:93 and 94. Germline sequences for the $V_H$ and $V_L$ domains can be identified by performing amino acid and nucleic acid sequence alignments against the VBASE database (MRC Center for Protein Engineering, UK). In some embodiments, the FR regions of the scFvs are mutated in conformity with the closest matches in the VBASE database and the CDR portions are kept intact.

In certain embodiments, antibodies of this invention specifically react with an epitope in the extracellular domain of human IL-21R. The predicted extracellular domain consists of a sequence from about amino acid 20 to about amino acid 235 of SEQ ID NO:43. In further embodiments, anti-IL-21R antibodies block the binding of IL-21 to IL-21R. In other embodiments, the anti-IL-21R antibodies specifically react with an epitope in the extracellular domain of mouse IL-21R. The extracellular domain of murine IL-21R consists of a sequence from about amino acid 20 to about amino acid 236 of SEQ ID NO:45. The extracellular domain of mouse IL-21R is about 65% identical to the human counterpart.

It is contemplated that antibodies of this invention may bind other proteins, such as, for example, recombinant proteins comprising all or portion of the IL-21R extracellular domain.

One of ordinary skill in the art will recognize that the disclosed antibodies may be used to detect, measure, and/or inhibit proteins that differ somewhat from IL-21R. For example, these proteins may be homologs of IL-21R. Anti-IL-21R antibodies are expected to bind proteins that comprise a sequence which is at least about 60%, 70%, 80%, 90%, 95%, 96%, 97%, 98%, 99% or more identical to any sequence of at least 100, 80, 60, 40, or 20 contiguous amino acids in the sequence set forth SEQ ID NO:43.

In addition to sequence homology analyses, epitope mapping (see, e.g., Epitope Mapping Protocols, ed. Morris, Humana Press, 1996), and secondary and tertiary structure analyses can be carried out to identified specific 3D structures assumed by the presently disclosed antibodies and their complexes with antigens. Such methods include, but are not limited to, X-ray crystallography (Engstom (1974) Biochem. Exp. Biol., 11:7-13) and computer modeling of virtual representations of the present antibodies (Fletterick et al. (1986) Computer Graphics and Molecular Modeling, in Current Communications in Molecular Biology, Cold Spring Harbor Laboratory, Cold Spring Harbor, N.Y.).

The disclosure provides a method for obtaining anti-IL-21R antibodies that comprises creating antibodies with altered Tables 1A and 1B $V_H$ and/or $V_L$ sequence(s). Such antibodies may be derived by a skilled artisan using techniques known in the art. For example, amino acid substitutions, deletions, or additions can be introduced in FR and/or CDR regions. FR changes are usually designed to improve the stability and immunogenicity of the antibody, while CDR changes are typically designed to increase antibody affinity for its antigen. The changes that increase affinity may be tested by altering CDR sequence and measuring antibody affinity for its target (see Antibody Engineering, 2nd ed., Oxford University Press, ed. Borrebaeck, 1995).

Antibodies whose CDR sequences differ insubstantially from those set out in SEQ ID NO:1, 2, 3, 4, 5, 6, 7, 8, 9, 19, 20, 21, 22, 23, 24, 25, 26, 27, 47, 48, 49, 50, 51, 52, 53, 54, 55, 65, 66, 67, 68, 69, 70, 71, 72, 73, 83, 84, 85, 86, 87, 88, 89, 90, 91, 101, 102, 103, 104, 105, 106, 107, 108, 109, 119, 120, 121, 122, 123, 124, 125, 126, 127, 137, 138, 139, 140, 141, 142, 143, 144, or 145 are encompassed within the scope of this invention. Typically, this involves substitution of an amino acid with an amino acid having similar charge, hydrophobic, or stereochemical characteristics. More drastic substitutions in FR regions, in contrast to CDR regions, may also be made as long as they do not adversely affect the binding properties of the antibody: Substitutions may also be made to germline the antibody or stabilize the antigen binding site.

Conservative modifications will produce molecules having functional and chemical characteristics similar to those of the molecule from which such modifications are made. In contrast, substantial modifications in the functional and/or chemical characteristics of the molecules may be accomplished by selecting substitutions in the amino acid sequence that differ significantly in their effect on maintaining (1) the structure of the molecular backbone in the area of the substitution, for example, as a sheet or helical conformation, (2) the charge or hydrophobicity of the molecule at the target site, or (3) the size of the molecule.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24).

Desired amino acid substitutions (whether conservative or non-conservative) can be determined by those skilled in the art at the time such substitutions are desired. For example, amino acid substitutions can be used to identify important residues of the molecule sequence, or to increase or decrease the affinity of the molecules described herein. Exemplary amino acid substitutions are set forth in Table 3.

TABLE 3

Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

In one embodiment, the method for making a variant $V_H$ domain comprises adding, deleting, or substituting at least one amino acid in the disclosed $V_H$ domains, or combining the disclosed $V_H$ domains with at least one $V_L$ domain, and testing the variant $V_H$ domain for IL-21R binding or modulation of IL-21R activity.

An analogous method for making a variant $V_L$ domain comprises adding, deleting, or substituting at least one amino acid in the disclosed $V_L$ domains, or combining the disclosed $V_L$ domains with at least one $V_H$ domain, and testing the variant $V_L$ domain for IL-21R binding or modulation of IL-21R activity.

A further aspect of the disclosure provides a method for preparing antigen-binding fragments that bind IL-21R. The method comprises:

(a) providing a starting repertoire of nucleic acids encoding a $V_H$ domain which lacks one or more of CDR1, 2 or 3 or contains a CDR1, 2 or 3 to be replaced;

(b) inserting into or replacing the CDR1, 2 or 3 region of the starting repertoire with a nucleic acid encoding an amino acid sequence as substantially as set out herein for a $V_H$ CDR 1, 2 or 3, yielding a product repertoire;

(c) expressing the nucleic acids of the product repertoire;

(d) selecting a specific antigen-binding fragment that binds to IL-21R; and (e) recovering the specific antigen-binding fragment or nucleic acid encoding it.

An analogous method in which the $V_L$ CDR1, 2 or 3 of the invention is combined with a repertoire of nucleic acids encoding a $V_L$ domain which lacks a CDR1, 2 or 3 or contains a CDR1, 2 or 3 to be replaced.

Using recombinant DNA methodology, a disclosed CDR sequence may be introduced into a repertoire of $V_H$ or $V_L$ domains lacking the respective CDR (Marks et al. (BioTechnology (1992) 10: 779-783). For example, a primer adjacent to the 5' end of the variable domain and a primer to the third FR can be used to generate a repertoire of variable domain sequences lacking CDR3. This repertoire can be combined with a CDR3 of a disclosed antibody. Using analogous techniques, portions of a disclosed CDR sequence may be shuffled with portions of CDR sequences from other antibodies to provide a repertoire of antigen-binding fragments that bind IL-21R. Either repertoire can be expressed in a host system such as phage display (described in WO 92/01047) so suitable antigen-binding fragments that bind to IL-21R can be selected.

A further alternative uses random mutagenesis of the disclosed $V_H$ or $V_L$ sequences to generate variant $V_H$ or $V_L$ domains still capable of binding IL-21R. A technique using error-prone PCR is described by Gram et al. (Proc. Nat. Acad. Sci. U.S.A. (1992) 89: 3576-3580).

Another method uses direct mutagenesis of the disclosed $V_H$ or $V_L$ sequences. Such techniques are disclosed by Barbas et al. (Proc. Nat. Acad. Sci. U.S.A. (1994) 91: 3809-3813) and Schier et al. (J. Mol. Biol. (1996) 263: 551-567).

A portion of a variable domain will comprise at least one CDR region substantially as set out herein and, optionally, intervening framework regions from the $V_H$ or $V_L$ domains as set out herein. The portion may include the C-terminal half of FR1 and/or the N-terminal half of FR4. Additional residues at the N-terminal or C-terminal end of the variable domain may not be same residues found in naturally occurring antibodies. For example, construction of antibodies by recombinant DNA techniques often introduces N- or C-terminal residues from its use of linkers. Some linkers may be used to join variable domains to other variable domains (e.g., diabodies), constant domains, or proteinaceous labels.

Although the embodiments illustrated in the Examples comprise a "matching" pair of $V_H$ and $V_L$ domains, a skilled artisan will recognize that alternative embodiments may comprise antigen-binding fragments containing only a single CDR from either $V_L$ or $V_H$ domain. Either one of the single chain specific antigen-binding domains can be used to screen for complementary domains capable of forming a two-domain specific antigen-binding fragment capable of, for example, binding to IL-21R. The screening may be accomplished by phage display screening methods using the so-called hierarchical dual combinatorial approach disclosed in WO 92/01047. In this approach, an individual colony containing either a H or L chain clone is used to infect a complete library of clones encoding the other chain (L or H), and the resulting two-chain specific antigen-binding domain is selected in accordance with phage display techniques as described.

In some alternative embodiments, the anti-IL-21R antibodies can be linked to a protein (e.g., albumin) by chemical cross-linking or recombinant methods. The disclosed antibodies may also be linked to a variety of nonproteinaceous polymers (e.g., polyethylene glycol, polypropylene glycol, or polyoxyalkylenes) in manners set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their half-life in blood circulation. Exemplary polymers and attachment methods are shown in U.S. Pat. Nos. 4,766,106; 4,179,337; 4,495,285; and 4,609,546.

The disclosed antibodies can be modified to alter their glycosylation; that is, at least one carbohydrate moiety can be deleted or added to the antibody. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the antibody (see WO 87/05330 and Aplin et al. (1981) *CRC Crit. Rev. Biochem.,* 22: 259-306). Removal of carbohydrate moieties can also be accomplished chemically or enzymatically (see Hakimuddin et al. (1987) *Arch. Biochem. Biophys.,* 259: 52; Edge et al. (1981) *Anal. Biochem.,* 118: 131; Thotakura et al. (1987) *Meth. Enzymol.,* 138: 350).

Methods for altering an antibody constant region are known in the art. Antibodies with altered function (e.g., altered affinity for an effector ligand such as FcR on a cell or the C1 component of complement) can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar types of alterations could be described which if applied to a murine or other species antibody would reduce or eliminate similar functions.

For example, it is possible to alter the affinity of an Fc region of an antibody (e.g., an IgG, such as a human IgG) for FcR (e.g., Fc gamma R1) or C1q. The affinity may be altered by replacing at least one specified residue with at least one residue having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821).

For example, replacing residue 297 (asparagine) with alanine in the IgG constant region significantly inhibits recruitment of effector cells, while only slightly reducing (about three fold weaker) affinity for Clq (see e.g., U.S. Pat. No. 5,624,821). The numbering of the residues in the heavy chain is that of the EU index (see Kabat et al., 1991 supra). This alteration destroys the glycosylation site and it is believed that the presence of carbohydrate is required for Fc receptor binding. Any other substitution at this site that destroys the glycosylation site is believed cause a similar decrease in lytic activity. Other amino acid substitutions, e.g., changing any one of residues 318 (Glu), 320 (Lys) and 322 (Lys), to Ala, are also known to abolish Clq binding to the Fc region of IgG antibodies (see e.g., U.S. Pat. No. 5,624,821).

Modified antibodies can be produced which have a reduced interaction with an Fc receptor. For example, it has been shown that in human $IgG_3$, which binds to the human Fc gamma R1 receptor, changing Leu 235 to Glu destroys its interaction with the receptor. Mutations on adjacent or close sites in the hinge link region of an antibody (e.g., replacing residues 234, 236 or 237 with Ala) can also be used to affect antibody affinity for the Fc gamma R1 receptor. The numbering of the residues in the heavy chain is based in the EU index (see Kabat et al., 1991 supra).

Additional methods for altering the lytic activity of an antibody, for example, by altering at least one amino acid in the N-terminal region of the CH2 domain, are described in WO 94/29351 by Morgan et al. and U.S. Pat. No. 5,624,821, the contents of all of which are hereby expressly incorporated by reference.

The antibodies of this invention may be tagged with a detectable or functional label. These labels include radiolabels (e.g., $^{131}I$ or $^{99}Tc$), enzymatic labels (e.g., horseradish peroxidase or alkaline phosphatase), and other chemical moieties (e.g., biotin).

One of skill in the art will appreciate that the modifications described above are not all-exhaustive, and that many other modifications are obvious to a skilled artisan in light of the teachings of the present disclosure.

Nucleic Acids, Cloning and Expression Systems

The disclosure provides isolated nucleic acids encoding the disclosed antibodies. The nucleic acids may comprise DNA or RNA, and they may be synthetic (completely or partially) or recombinant (completely or partially). Reference to a nucleotide sequence as set out herein encompasses a DNA molecule with the specified sequence, and encompasses a RNA molecule with the specified sequence in which U is substituted for T.

Also provided are nucleic acids that comprise a coding sequence for one, two, or three CDR's, a $V_H$ domain, a $V_L$ domain, or combinations thereof, as disclosed herein, or a sequence substantially identical thereto (e.g., a sequence at least 85%, 90%, 95%, 96%, 97%, 98%, 99% or higher identical thereto, or which is capable of hybridizing under stringent conditions to the sequences disclosed).

In one embodiment, the isolated nucleic acids have nucleotide sequences encoding heavy chain and light chain variable regions of an anti-IL-21R antibody having at least one CDR chosen from the amino acid sequences of SEQ ID NO:4, 5, 6, 7, 8, 9, 22, 23, 24, 25, 26, 27, 50, 51, 52, 53, 54, 55, 68, 69, 70, 71, 72, 73, 86, 87, 88, 89, 90, 91, 104, 105, 106, 107, 108, 109, 122, 123, 124, 125, 126, 127, 140, 141, 142, 143, 144 and 145 or sequence encoding a CDR which differs by one or two amino acids from the sequences described herein. In some embodiments, the amino acid sequence of a CDR includes conservative amino acid substitutions of one or more amino acids in sequences shown in SEQ ID NO:4, 5, 6, 7, 8, 9, 22, 23, 24, 25, 26, 27, 50, 51, 52, 53, 54, 55, 68, 69, 70, 71, 72, 73, 86, 87, 88, 89, 90, 91, 104, 105, 106, 107, 108, 109, 122, 123, 124, 125, 126, 127, 140, 141, 142, 143, 144 and 145.

A nucleic acid may encode only the light chain or the heavy chain variable region, or may also encode an antibody light or heavy chain constant region, operatively linked to the corresponding variable region. In one embodiment, a light chain variable region ($V_L$) is linked to a constant region chosen from a kappa or a lambda constant region. The light chain constant region may also be a human kappa or lambda type. In another embodiment, a heavy chain variable region ($V_H$) is linked to a heavy chain constant region of an antibody isotype chosen from IgG (e.g., $IgG_1$, $IgG_2$, $IgG_3$, $IgG_4$), IgM, $IgA_1$, $IgA_2$, IgD, and IgE. The heavy chain constant region may be an IgG (e.g., an $IgG_1$) isotype.

Nucleic acid compositions of the present invention, while often in the native sequence (of cDNA or genomic DNA or mixtures thereof) except for modified restriction sites and the like, may be mutated in accordance with standard techniques to provide gene sequences. For coding sequences, these mutations, may affect amino acid sequence as desired. In particular, nucleotide sequences substantially identical to or derived from native V, D, J, constant, switches and other such sequences described herein are contemplated (where "derived" indicates that a sequence is identical or modified from another sequence).

In one embodiment, a nucleic acid differs (e.g., differs by substitution, insertion, or deletion) from that of the sequences provided (e.g., as follows: by at least one but less than 10, 20, 30, or 40 nucleotides; at least one but less than 1%, 5%, 10% or 20% of the nucleotides in the subject nucleic acid). If necessary for this analysis the sequences should be aligned for maximum homology. "Looped" out sequences from deletions or insertions, or mismatches, are considered differences. The difference may be at a nucleotide(s) encoding a nonessential residue(s), or the difference may be a conservative substitution(s). The disclosure also provides nucleic acid constructs in the form of plasmids, vectors, transcription or expression cassettes, which comprise at least one nucleic acid as described herein.

The disclosure further provides a host cell that comprises at least one nucleic acid construct described herein. Also provided are the methods of making the encoded protein(s) from the nucleic acid(s) comprising sequence described herein. The method comprises culturing host cells under appropriate conditions so they express the protein from the nucleic acid. Following expression and production, the $V_H$ or $V_L$ domain, or specific binding member may be isolated and/or purified using any suitable technique, then used as appropriate.

Antigen-binding fragments, $V_H$ and/or $V_L$ domains, and encoding nucleic acid molecules and vectors may be isolated and/or purified from their natural environment, in substantially pure or homogenous form, or, in the case of nucleic acid, free or substantially free of nucleic acid or genes of origin other than the sequence encoding a polypeptide with the require function.

Systems for cloning and expressing polypeptides in a variety of host cells are known in the art. Cells suitable for producing antibodies are described in, for example, Fernandez et al. (1999) Gene Expression Systems, Academic Press, eds. In brief, suitable host cells include mammalian cells, insect cells, plant cells, yeast cells, or prokaryotic cells, e.g., *E. coli*. Mammalian cells available in the art for heterologous polypeptide expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cell. In one embodiment, the MUF and MU11 antibodies are expressed in HEK293 or CHO cells. In other embodiments, nucleic acids encoding the antibodies of-the invention are placed under the control of a tissue-specific promoter (e.g., a mammary specific promoter) and the antibodies are produced in transgenic animals. For example, antibodies are secreted into the milk of the transgenic animal, such as a transgenic cow, pig, horse, sheep, goat or rodent. Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone. For details, see Sambrook et al., Molecular Cloning: A Laboratory Manual, 2nd ed., Cold Spring Harbor Laboratory Press (1989). Many established techniques used with vectors, including the manipulation, preparation, mutagenesis, sequencing, and transfection of DNA, are described in Current Protocols in Molecular Biology, Second Edition, Ausubel et al. eds., John Wiley & Sons (1992).

A further aspect of the disclosure provides a method of introducing the nucleic acid into a host cell. For eukaryotic cells, suitable transfection techniques may include calcium phosphate, DEAE-Dextran, electroporation, liposome-mediated transfection, and transduction using retrovirus or other viruses, e.g., vaccinia or baculovirus. For bacterial cells, suitable techniques may include calcium chloride transformation, electroporation, and transfection using bacteriophage. DNA introduction may be followed by a selection method (e.g., drug resistance) to select cells that contain the nucleic acid.

Biological Deposits

CHO cells transformed with vectors containing MUF heavy chain and light chain, and CHO cells transformed with vectors containing MU11 heavy and light chain, were deposited on Mar. 5, 2003, at American Tissue Culture Collection (ATCC) under respective Deposit Designation Numbers PTA-5031 and PTA-5030. The address of the depository is 10801 University Blvd, Manassas, Va. 20110, U.S.A.

Uses of Anti-IL-21R Antibodies

Anti-IL-21R antibodies that act as antagonists to IL-21R can be used to regulate at least one IL-21R-mediated immune response, such as, one or more of cell proliferation, cytokine secretion, chemokine secretion, and cytolytic activity, of T cells, B cells, NK cells, macrophages, or synovial cells. Accordingly, the antibodies of the invention can be used to inhibit the activity (e.g., proliferation, differentiation, and/or survival) of an immune or hematopoietic cell (e.g., a cell of myeloid, lymphoid, or erythroid lineage, or precursor cells thereof), and, thus, can be used to treat a variety of immune disorders and hyperproliferative disorders. Non-limiting examples of immune disorders that can be treated include, but are not limited to, transplant rejection, graft-versus-host disease, allergies (for example, atopic allergy) and autoimmune diseases. Autoimmune diseases may include diabetes mellitus, arthritic disorders (including rheumatoid arthritis, juvenile rheumatoid arthritis, osteoarthritis, psoriatic arthritis, and ankylosing spondylitis), spondyloarthropathy, multiple sclerosis, encephalomyelitis, myasthenia gravis, systemic lupus erythematosis, cutaneous lupus erythematosus, autoimmune thyroiditis, dermatitis (including atopic dermatitis and eczematous dermatitis), psoriasis, Sjögren's Syndrome, IBD (including Crohn's disease and ulcerative colitis), asthma (including intrinsic asthma and allergic asthma), scleroderma and vasculitis.

Multiple sclerosis is a central nervous system disease that is characterized by inflammation and loss of myelin sheaths—the fatty material that insulates nerves and is needed for proper nerve function. Inflammation that results from an immune response that is dependent on IL-21 can be treated with the antibodies and compositions of this invention. In the experimental autoimmune encephalitis (EAE) mouse model for multiple sclerosis (Tuohy et al. (J. Immunol. (1988) 141: 1126-1130), Sobel et al. (J. Immunol. (1984) 132: 2393-2401), and Traugott (Cell Immunol. (1989) 119: 114-129), treatment of mice with MU11 injections prior (and continuously) to EAE induction profoundly delays the onset of the disease. The antibodies of this invention may similarly be used to treat multiple sclerosis in humans.

Arthritis is a disease characterized by inflammation in the joints. Rheumatoid Arthritis (RA) is the most frequent form of arthritis, involving inflammation of connective tissue and the synovial membrane, a membrane that lines the joint. The inflamed synovial membrane often infiltrates the joint and damages joint cartilage and bone. Studies show that treatment of synovial cells and macrophages with IL-21 induces these cells to secrete cytokines and chemokines associated with inflammation. In the collagen induced arthritis (CIA) mouse model for rheumatoid arthritis (Courtenay et al. (Nature (1980) 283: 666-628) and Williams et al. (Immunol. (1995) 84: 433-439)), treatment of mice with IL-21 subsequently (and continuously) to CIA induction exacerbates the disease. Increased secretion of inflammatory cytokines and chemokines, and more importantly, increased disease resulting from immune responses that are dependent on IL-21 may be treated with the antibodies of this invention. Similarly, the antibodies and compositions of this invention may be used to treat RA or other arthritic diseases in humans.

Transplant rejection is the immunological phenomenon where tissues from a donor are specifically "attacked" by immune cells of the host. The principle "attacking" cells are T cells, whose T cell receptors recognize the donor's MHC molecules as "foreign." This recognition activates the T cell, which proliferates and secretes a variety of cytokines and cytolytic proteins that ultimately destroy the transplant. T cells in a mixed lymphocyte reaction (MLR), an in vitro assay of transplant rejection, proliferate more strongly when supplemented with IL-21. MLR and transplantation models have been described by Current Protocols in Immunology, Second Edition, Coligan et al. eds., John Wiley & Sons, 1994; Kasaian et al. (Immunity (2002) 16: 559-569); Fulmer et al. (Am. J. Anat. (1963) 113: 273-285), and Lenschow et al. (Science (1992) 257: 789-792). The antibodies and compositions of this invention may be used to reduce the MLR and treat transplant rejection and related diseases (e.g.; graft versus host disease) in humans that are dependent on IL-21.

Systemic Lupus Erythematosis (SLE) is an autoimmune disease characterized by the presence of autoantibodies, including antibodies to DNA, nuclear antigens, and ribonucleoproteins. These autoantibodies are associated with tissue and organ damage. The cause of SLE is unknown, but the occurrence of autoantibodies suggests inadequate inhibition of autoreactive T cells or B cells. The antibodies and compositions of this invention can be used to inhibit the IL-21 mediated activities of autoreactive T cells and B cells, and treat SLE or related diseases in NZB×NZW mice (the mouse model for SLE) (Immunologic Defects in Laboratory Animals, Gershwin et al. eds., Plenum Press, 1981) or in humans.

Antibodies of this invention can also be used to treat hyperproliferative disorders associated with aberrant activity of IL-21-responsive cells and IL-21R-responsive cells. Examples of such cells include neoplastic cells of hematopoietic origin, e.g., cells arising from myeloid, lymphoid or erythroid lineages, or precursor cells thereof. Examples of such neoplastic disorders include leukemic cancers, and tumors of the blood, bone marrow (e.g., myeloma), and lymph tissue (e.g., lymphomas). In certain embodiments, the present invention is directed to the treatment of various leukemic cancers including, but not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267-97). Examples of lymphoid malignancies that may be treated by the subject methods include, but are not limited to, acute lymphoblastic leukemia (ALL, which includes B-lineage ALL and T-lineage ALL), chronic lymphocytic leukemia (CLL), prolymphocytic leukemia (PLL), hairy cell leukemia (HLL), and Waldenstrom's macroglobulinemia (WM). Additional forms of malignant lymphomas that can be treated by the present invention include, but not limited to, non-Hodgkin's lymphoma, peripheral T cell lymphomas, adult T cell leukemia/lymphoma (ATL), cutaneous T cell lymphoma (CTCL), large granular lymphocytic leukemia (LGF), Hodgkin's lymphoma, and variants thereof.

Combination Therapy

In one embodiment, a pharmaceutical composition comprising at least one anti-IL-21R antibody and at least one therapeutic agent is administered in combination therapy. The therapy is useful for treating pathological conditions or disorders, such as immune and inflammatory disorders. The term "in combination" in this context means that the antibody composition and the therapeutic agent are given substantially contemporaneously, either simultaneously or sequentially. If given sequentially, at the onset of administration of the second compound, the first of the two compounds may stilt be detectable at effective concentrations at the site of treatment.

For example, the combination therapy can include at least one anti-IL-21R antibody co-formulated with, and/or co-administered with, at least one additional therapeutic agent. The additional agents may include at least one cytokine inhibitor, growth factor inhibitor, immunosuppressant, anti-inflammatory agent, metabolic inhibitor, enzyme inhibitor, cytotoxic agent, and cytostatic agent, as described in more detail below. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-21/IL-21R pathway, and thus are expected to enhance and/or synergize with the effects of the anti-IL-21R antibodies.

Therapeutic agents used in combination with anti-IL-21R antibodies may be those agents that interfere at different stages in the autoimmune and subsequent inflammatory response. In one embodiment, at least one anti-IL-21R antibody described herein may be co-formulated with, and/or co-administered with, at least one cytokine and/or growth factor antagonist. The antagonists may include soluble receptors, peptide inhibitors, small molecules, ligand fusions, antibodies (that bind cytokines or growth factors or their receptors or other cell surface molecules), and "anti-inflammatory cytokines" and agonists thereof.

Non-limiting examples of the agents that can be used in combination with the anti-IL-21R antibodies described herein, include, but are not limited to, antagonists of at least one interleukin (e.g., IL-1, IL-2, IL-6, IL-7, IL-8, IL-12, IL-13, IL-15, IL-16, IL-17, IL-18, and IL-22); cytokine (e.g., TNFα, LT, EMAP-II, and GM-CSF); and growth factor (e.g., FGF and PDGF). The agents may also include, but not limited to, antagonists of at least one receptor for an interleukin, cytokine, and growth factor. Anti-IL-21R antibodies can also be combined with inhibitors (e.g., antibodies) to cell surface molecules such as CD2, CD3, CD4, CD8, CD25, CD28, CD30, CD40, CD45, CD69, CD80 (B7.1), CD86 (B7.2), CD90, or their ligands (e.g., CD154 (gp39, CD40L)), or LFA-1/ICAM-1 and VLA-4/VCAM-1 (Yusuf-Makagiansar et al. (2002) *Med Res Rev* 22(2):146-67)). Antagonists that can be used in combination with anti-IL-21R antibodies described herein may include antagonists of IL-1, IL-12, TNFα, IL-15, IL-17, IL-18, IL-22, and their receptors.

Examples of those agents include IL-12 antagonists (such as antibodies that bind IL-12 (see e.g., WO 00/56772, Genetics Institute/BASF)); IL-12 receptor inhibitors (such as antibodies to the IL-12 receptor); and soluble IL-12 receptor and fragments thereof. Examples of IL-15 antagonists include antibodies against IL-15 or its receptor, soluble fragments of the IL-15 receptor, and IL-15-binding proteins. Examples of IL-18 antagonists include antibodies to IL-18, soluble fragments of the IL-18 receptor, and IL-18 binding proteins (IL-18BP, Mallet et al. (2001) Circ. Res. 28). Examples of IL-1 antagonists include Interleukin-1-Converting Enzyme (ICE) inhibitors (such as Vx740), IL-1 antagonists (e.g., IL-1RA (ANIKINRA, AMGEN)), sIL-1RII (Immunex), and anti-IL-1 receptor antibodies.

Examples of TNF antagonists include antibodies to TNF (e.g., human TNFα), such as D2E7 (human anti-TNFα antibody, U.S. Pat. No. 6,258,562, Humira™, BASF); CDP-571/CDP-870/BAY-10-3356 (humanized anti-TNFα antibodies, Celltech/Pharmacia); cA2 (chimeric anti-TNFα antibody, Remicade™, Centocor); and anti-TNF antibody fragments (e.g., CPD870). Other examples include soluble TNF receptor (e.g., human p55 or p75) fragments and derivatives, such as p55 kdTNFR-IgG (55 kD TNF receptor-IgG fusion protein, Lenercept™) and 75 kdTNFR-IgG (75 kD TNF receptor-IgG fusion protein, Enbrel™, Immunex, see, e.g., Arthritis & Rheumatism (1994) Vol. 37, S295; J. Invest. Med. (1996) Vol. 44, 235A). Further examples include enzyme antagonists (e.g., TNFα converting enzyme inhibitors (TACE) such as alpha-sulfonyl hydroxamic acid derivative (WO 01/55112) or N-hydroxyformamide inhibitor (GW 3333, -005, or -022)) and TNF-bp/s-TNFR (soluble TNF binding protein, see e.g., Arthritis & Rheumatism (1996) Vol. 39, No. 9 (supplement), S284; and Am. J. Physiol. Heart Circ. Physiol. (1995) Vol. 268, pp. 37-42). TNF antagonists may be soluble TNF receptor (e.g., human p55 or p75) fragments and derivatives, such as 75 kdTNFR-IgG; and TNFα converting enzyme (TACE) inhibitors.

In other embodiments, the anti-IL-21R antibodies described herein can be administered in combination with at least one of the following: IL-13 antagonists, such as soluble IL-13 receptors and/or anti-IL-13 antibodies; and IL-2 antagonists, such as IL-2 fusion proteins (e.g., DAB 486-IL-2 and/or DAB 389-IL-2, Seragen, see e.g., Arthritis & Rheumatism (1993) Vol. 36, 1223) and anti-IL-2R antibodies (e.g., anti-Tac (humanized antibody, Protein Design Labs, see Cancer Res. 1990 Mar. 1; 50(5):1495-502)). Another combination includes anti-IL-21R antibodies in combination with non-depleting anti-CD4 inhibitors such as IDEC-CE9.1/SB 210396 (anti-CD4 antibody, IDEC/SmithKline). Yet other combinations include anti-IL-21R antibodies with CD80 (B7.1) and CD86 (B7.2) co-stimulatory pathway antagonists (such as antibodies, soluble receptors, or antagonistic ligands); P-selectin glycoprotein ligand (PSGL); and anti-inflammatory cytokines and agonists thereof (e.g., antibodies). The anti-inflammatory cytokines may include IL-4 (DNAX/Schering); IL-10 (SCH 52000, recombinant IL-10, DNAX/Schering); IL-13; and TGF.

In other embodiments, at least one anti-IL-21R antibody can be co-formulated with, and/or co-administered with, at least one anti-inflammatory drug, immunosuppressant, metabolic inhibitor, and enzymatic inhibitor. Non-limiting examples of the drugs or inhibitors that can be used in combination with the IL-21 antagonists described herein, include, but are not limited to, at least one of: non-steroidal anti-inflammatory drug (NSAID) (such as ibuprofen, Tenidap (see e.g., Arthritis & Rheumatism (1996) Vol. 39, No. 9 (supplement), S280)), Naproxen (see e.g., Neuro Report (1996) Vol. 7, pp. 1209-1213), Meloxicam, Piroxicam, Diclofenac, and Indomethacin); Sulfasalazine (see e.g., Arthritis & Rheumatism (1996) Vol. 39, No. 9 (supplement), S281); corticosteroid (such as prednisolone); cytokine suppressive anti-inflammatory drug (CSAID); and an inhibitor of nucleotide biosynthesis (such as an inhibitor of purine biosynthesis (e.g., folate antagonist such as methotrexate) and an inhibitor of pyrimidine biosynthesis (e.g., a dihydroorotate dehydrogenase (DHODH) inhibitor such as leflunomide (see e.g., *Arthritis & Rheumatism* (1996) Vol. 39, No. 9 (supplement), S131; Inflammation Research (1996) Vol. 45, pp. 103-107)). Therapeutic agents for use in combination with IL-21/IL-21R antagonists may include NSAIDs, CSAIDs, DHODH inhibitors (such as leflunomide), and folate antagonists (such as methotrexate).

Examples of additional inhibitors include at least one of: corticosteroid (oral, inhaled and local injection); immunosuppressant (such as cyclosporin and tacrolimus (FK-506)); a mTOR inhibitor (such as sirolimus (rapamycin) or a rapamycin derivative (e.g., ester rapamycin derivative such as CCI-779 (Elit. L. (2002) *Current Opinion Investig. Drugs* 3(8): 1249-53; Huang, S. et al. (2002) *Current Opinion Investig. Drugs* 3(2):295-304))); an agent which interferes with the signaling of proinflammatory cytokines such as TNFα and IL-1 (e.g., IRAK, NIK, IKK, p38 or a MAP kinase inhibitor); a COX2 inhibitor (e.g., celecoxib and variants thereof (MK-966), see e.g., Arthritis & Rheumatism (1996) Vol. 39, No. 9 (supplement), S81); a phosphodiesterase inhibitor (such as R973401, see e.g., Arthritis & Rheumatism (1996) Vol. 39, No. 9 (supplement), S282)); a phospholipase inhibitor (e.g., an inhibitor of cytosolic phospholipase 2 (cPLA2) such as trifluoromethyl ketone analogs (U.S. Pat. No. 6,350,892)); an inhibitor of vascular endothelial cell growth factor (VEGF); an inhibitor of the VEGF receptor; and an inhibitor of angiogenesis. Therapeutic agents for use in combination with anti-IL-21R antibodies may include immunosuppresants (such as cyclosporine and tacrolimus (FK-506)); and mTOR inhibitors (such as sirolimus (rapamycin) or rapamycin derivatives (e.g., ester rapamycin derivatives such as CCI-779)); COX2 inhibitors (such as celecoxib and variants thereof); and phospholipase inhibitors (such as inhibitors of cytosolic phospholipase 2 (cPLA2) (e.g., trifluoromethyl ketone analogs)).

Examples of therapeutic agents that can be co-administered and/or co-formulated with at least one anti-IL-21R antibody, include, but are not limited to, at least one of: TNF antagonists (such as anti-TNF antibodies); soluble fragments of TNF receptors (e.g., human p55 and p75) and derivatives thereof (such as p55 kdTNFR-IgG (55 kD TNF receptor-IgG fusion protein, Lenercept™) and 75 kdTNFR-IgG (75 kD TNF receptor-IgG fusion protein, Enbrel™)); TNF enzyme antagonists (such as TACE inhibitors); antagonists of IL-12, IL-15, IL-17, IL-18, and IL-22; T cell and B cell depleting agents (such as anti-CD4 or anti-CD22 antibodies); small molecule inhibitors (such as methotrexate and leflunomide); sirolimus (rapamycin) and analogs thereof (such as CCI-779); Cox-2 and cPLA2 inhibitors; p38, TPL-2, Mk-2 and NFκB inhibitors; RAGE and soluble RAGE; P-selectin and PSGL-1 inhibitors (such as antibodies to and small molecule inhibitors); and estrogen receptor beta (ERB) agonists, and ERB-NFkb antagonists. Therapeutic agents that can be co-administered and/or co-formulated with at least one anti-IL-21R antibody may include at least one of: a soluble fragment of a TNF receptor (e.g., human p55 or p75) such as 75 kdTNFR-IgG (75 kD TNF receptor-IgG fusion protein, Enbrel™); methotrexate; leflunomide; and sirolimus (rapamycin) and analogs thereof (such as CCI-779).

The anti-IL-21R antibodies disclosed herein can be used in combination with other therapeutic agents to treat specific immune disorders as discussed in further detail below.

Non-limiting examples of agents for treating arthritic disorders (e.g., rheumatoid arthritis, inflammatory arthritis, rheumatoid arthritis, juvenile rheumatoid arthritis, osteoarthritis and psoriatic arthritis), with which an anti-IL-21R antibody can be combined include at least one of the following: TNF antagonists (such as anti-TNF antibodies); soluble fragments of TNF receptors (e.g., human p55 and p75) and derivatives thereof (such as p55 kdTNFR-IgG (55 kD TNF receptor-IgG fusion protein, Lenercept™) and 75 kdTNFR-IgG (75 kD TNF receptor-IgG fusion protein, Enbrel™)); TNF enzyme antagonists (such as TACE inhibitors); antagonists of IL-12, IL-15, IL-17, IL-18, and IL-22; T cell and B cell depleting agents (such as anti-CD4 or anti-CD22 antibodies); small molecule inhibitors (such as methotrexate and leflunomide); sirolimus (rapamycin) and analogs thereof (e.g., CCI-779); Cox-2 and cPLA2 inhibitors; NSAIDs; p38, TPL-2, Mk-2, and NFκB inhibitors; RAGE or soluble RAGE; P-selectin or PSGL-1 inhibitors (such as small molecule inhibitors and antibodies to); estrogen receptor beta (ERB) agonists, and ERB-NFκB antagonists. Therapeutic agents that can be co-administered and/or co-formulated with at least one IL-21/IL-21R antagonist may include at least one of: a soluble fragment of a TNF receptor (e.g., human p55 or p75) such as 75 kdTNFR-IgG (75 kD TNF receptor-IgG fusion protein, Enbrel™); methotrexate; leflunomide; and sirolimus (rapamycin) or an analog thereof (e.g., CCI-779).

Non-limiting examples of agents for treating multiple sclerosis with which anti-IL-21R antibody can be combined include interferon-β (for example, IFNβ-1a and IFNβ-1b), copaxone, corticosteroids, IL-I inhibitors, TNF inhibitors, antibodies to CD40 ligand, antibodies to CD80, and IL-12 antagonists.

Non-limiting examples of agents for treating inflammatory bowel disease or Crohn's disease with which an anti-IL-21R antibody can be combined include budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13, and/or TGFβ or agonists thereof (e.g., agonist antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

In other embodiments, an anti-IL-21R antibody can be used in combination with at least one antibody directed at other targets involved in regulating immune responses, e.g., transplant rejection or graft versus host disease. Non-limiting examples of agents for treating immune responses with which an IL-21/IL-21R antagonist of the invention can be combined include the following: antibodies against cell surface molecules, including but not limited to CD25 (IL-2 receptor α), CD11a (LFA-1), CD54 (ICAM-1), CD4, CD45, CD28/CTLA4, CD80 (B7-1), CD86 (B7-2), or combinations thereof. In another embodiment, an anti-IL-21R antibody is used in combination with at least one general immunosuppressive agent, such as cyclosporin A or FK506.

Another aspect of the present invention accordingly relates to kits for carrying out the combined administration of anti-IL-21R antibodies with other therapeutic agents. In one embodiment, the kit comprises at least one anti-IL-21R antibody formulated in a pharmaceutical carrier, and at least one therapeutic agent, formulated as appropriate in one or more separate pharmaceutical preparations.

Diagnostic Uses

Antibodies according to this invention may also be used to detect the presence of IL-21R in biological samples. By correlating the presence or level of these proteins with a medical condition, one of skill in the art can diagnose the associated medical condition. For example, stimulated T cells increase their expression of IL-21R, and an unusually high concentration of IL-21R expressing T cells in joints may indicate joint inflammation and possible arthritis. Illustrative medical conditions that may be diagnosed by the antibodies of this invention include multiple sclerosis, rheumatoid arthritis, and transplant rejection.

Antibody-based detection methods are well known in the art, and include ELISA, radioimmunoassays, immunoblots, Western blots, flow cytometry, immunofluorescence, immunoprecipitation, and other related techniques. The antibodies may be provided in a diagnostic kit that incorporates at least one of these procedures to detect IL-21R. The kit may contain other components, packaging, instructions, or other material to aid the detection of the protein and use of the kit.

Antibodies may be modified with detectable markers, including ligand groups (e.g., biotin), fluorophores and chromophores, radioisotopes, electron-dense reagents, or enzymes. Enzymes are detected by their activity. For example, horseradish peroxidase is detected by its ability to convert tetramethylbenzidine (TMB) to a blue pigment, quantifiable with a spectrophotometer. Other suitable binding partners include biotin and avidin, IgG and protein A, and other receptor-ligand pairs known in the art.

Antibodies can also be functionally linked (e.g., by chemical coupling, genetic fusion, non-covalent association or otherwise) to at least one other molecular entity, such as another antibody (e.g., a bispecific or a multispecific antibody), toxins, radioisotopes, cytotoxic or cytostatic agents, among others. Other permutations and possibilities are apparent to those of ordinary skill in the art, and they are considered equivalents within the scope of this invention.

Pharmaceutical Compositions and Methods of Administration

Certain embodiments of the invention include compositions comprising the disclosed antibodies. The compositions may be suitable for pharmaceutical use and administration to patients. The compositions comprise an antibody of the present invention and a pharmaceutical excipient. As used herein, "pharmaceutical excipient" includes solvents, dispersion media, coatings, antibacterial and antifungal agents, isotonic and absorption delaying agents, etc., that are compatible with pharmaceutical administration. Use of these agents for pharmaceutically active substances is well known in the art. Compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. It may also be possible to create compositions which may be topically or orally administered, or which may be capable of transmission across mucous membranes. For example, the administration may be intravenous, intraperitoneal, intramuscular, intracavity, subcutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, Cremophor EL™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin.

Oral compositions include an inert diluent or edible carrier. The composition can be enclosed in gelatin or compressed into tablets. For the purpose of oral administration, the antibodies can be incorporated with excipients and placed in tablets, troches, or capsules. Pharmaceutically compatible binding agents or adjuvant materials can be included in the composition. The tablets, troches, and capsules, may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; or (6) a sweetening agent or a flavoring agent.

Compositions may also be administered by a transmucosal or transdermal route. For example, antibodies that comprise a Fc portion may be capable of crossing mucous membranes in the intestine, mouth, or lungs (via Fc receptors). Transmucosal administration can be accomplished through the use of lozenges, nasal sprays, inhalers, or suppositories. Transdermal administration can also be accomplished through the use of composition containing ointments, salves, gels, or creams known in the art. For transmucosal or transdermal administration, penetrants appropriate to the barrier to be permeated are used. For administration by inhalation, antibodies are delivered in an aerosol spray from a pressured container or dispenser, which contains a propellant (e.g., liquid or gas) or a nebulizer.

In certain embodiments, antibodies of this invention are prepared with carriers to protect the antibodies against rapid elimination from the body. Biodegradable polymers (e.g., ethylene vinyl acetate, polyanhydrides, polyglycolic acid, collagen, polyorthoesters, polylactic acid) are often used. Methods for the preparation of such formulations are known by those skilled in the art. Liposomal suspensions can be used as pharmaceutically acceptable carriers too. The liposomes can be prepared according to established methods known in the art (U.S. Pat. No. 4,522,811).

Antibodies or antibody compositions of the invention are administered in therapeutically effective amounts as described. Therapeutically effective amounts may vary with the subject's age, condition, sex, and severity of medical condition. Appropriate dosage may be determined by a physician based on clinical indications. Antibodies or compositions may be given as a bolus dose to maximize the circulating levels of antibodies for the greatest length of time. Continuous infusion may also be used after the bolus dose.

As used herein, the term "subject" is intended to include human and non-human animals. Subjects may include a human patient having a disorder characterized by cells that express IL-21R, e.g., a cancer cell or an immune cell. The term "non-human animals" of the invention includes all vertebrates, such as non-human primates, sheep, dogs, cows, chickens, amphibians, reptiles, etc.

Examples of dosage ranges that can be administered to a subject can be chosen from: 1 μg/kg to 20 mg/kg, 1 μg/kg to 10 mg/kg, 1 μg/kg to 1 mg/kg, 10 μg/kg to 1 mg/kg, 10 μg/kg to 100 μg/kg, 100 μg to 1 mg/kg, 500 μg/kg to 1 mg/kg.

It may be advantageous to formulate compositions in dosage unit form for ease of administration and uniformity of dosage. Dosage unit form as used herein refers to physically discrete units suited for the patient. Each dosage unit contains a predetermined quantity of antibody calculated to produce a therapeutic effect in association with the carrier. The dosage unit depends on the characteristics of the antibodies and the particular therapeutic effect to be achieved.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices may be less toxic and/or more therapeutically effective.

The data obtained from the cell culture assays and animal studies can be used to formulate a dosage range in humans. The dosage of these compounds may lie within the range of circulating antibody concentrations in the blood, that includes an $ED_{50}$ with little or no toxicity. The dosage may vary within this range depending upon the dosage composition form employed and the route of administration. For any antibody used in the present invention, the therapeutically effective dose can be estimated initially using cell culture assays. A dose may be formulated in animal models to achieve a circulating plasma concentration range that includes the $IC_{50}$ (i.e., the concentration of antibody which achieves a half-maximal inhibition of symptoms). The effects of any particular dosage can be monitored by a suitable bioassay. Examples of suitable bioassays include DNA replication assays, transcription-based assays, IL-21R/IL-21 binding assays, and other immunological assays.

The following examples do not in any way limit the scope of the invention. One of ordinary skill in the art will recognize the numerous modifications and variations that may be performed without altering the spirit or scope of the present invention. Such modifications and variations are encompassed within the scope of the invention. The entire contents of all references, patents and published patent applications cited throughout this application are incorporated by reference.

EXAMPLES

Example 1

Selection of MUF and MU11 Anti-IL-21R $scF_v$'s

An $scF_v$ phagemid library, which is an expanded version of the $1.38\times10^{10}$ library described by Vaughan et al. ((1996) *Nature Biotech.*, 14: 309-314), was used to select antibodies specific for human IL-21R. Wells of microtiter plates were coated with soluble IL-21R fusion protein or control fusion protein (5-20 μg/ml in phosphate buffered saline (PBS)) and incubated overnight at 4° C. Wells were washed in PBS, then blocked for 1 hour at 37° C. in MPBS (3% milk powder in PBS). Purified phage ($10^{12}$ transducing units), blocked for 1 hour in MPBS, were added to the control fusion protein coated wells and incubated for 1 hour. The unbound phage was then transferred to IL-21R fusion protein wells and incubated for one hour. Wells were washed 5 times with PBST (0.1% v/v Tween 20 in PBS), then 5 times with PBS. Bound phage were eluted and used to infect exponentially growing *E. coli* TG1. Infected cells were grown in 2TY broth for 1 hour at 37° C., then streaked onto 2TYAG plates and incubated overnight at 30° C. The next day, colonies were transferred into 10 ml of 2TY broth plus 15% glycerol and stored at −70° C. Later, colonies from this first round of selection were thawed and superinfected with helper phage to rescue (generate) $scF_v$ antibody-expressing phage for a second round of selection.

Example 2

Selection of R18 and 19F5 Anti-IL-21R scFvs

Anti-IL21 R scFv (R18) was isolated using 200 nM of biotinylated human IL-21R fusion protein (bio.hIL21R) (Wyeth, Giralda Farms, N.J.) in solution. Purified scFv phage ($10^{12}$ tu) was blocked with MPBS and 125 μg/ml control fusion protein, as described above in Example 1. Biotinylated IL-21R fusion protein was added to the blocked phage to a final concentration of 200 nM and incubated for 1 hour at room temperature. Phage/antigen was added to 75 μl of Dynal M280 Streptavidin magnetic beads (Dynal Biotech Inc., Lake Success, N.Y.) that had been blocked for 90 minutes at room temperature in 1 ml of 3% MPBS. The mixture was incubated for 15 minutes at room temperature with mixing. Beads were captured using a magnetic rack and washed 5 times in 1 ml PBST followed by three washes in PBS. Bound phage were eluted with 500 μl of 10 μg/ml trypsin in 0.2 M sodium phosphate buffer, pH 7.0 and incubated at 37° C. for 30 minutes. Eluted phage were used to infect 10 ml exponentially growing *E. coil* TG-1 cells as described above. ScFv clones were isolated after three rounds of selection.

ScFv production was induced by addition of 1 mM IPTG to exponentially growing cultures and incubation overnight at 30° C. Crude scFv-containing periplasmic extracts (Griffiths et al. (1993) *EMBO J.,* 12:725-734) were screened for the ability to inhibit the binding of human IL-21R fusion protein to human IL-21-FLAG tagged protein. Briefly, anti-FLAG antibody was immobilized onto plastic and used to capture FLAG-tagged human IL-21 protein. Binding of human IL-21R fusion protein was detected with a Europium-labelled antibody to the IL-21R fusion protein, and time resolved fluorescence was detected with the DELFIA reagent kit (PerkinElmer, Boston, Mass.). Purified scFv R18 clone exhibited an $IC_{50}$ value of 770 nM for inhibition of IL-21R fusion protein binding to IL-21-FLAG tagged protein.

Anti-IL21R clone 19F5 was isolated by selection method as used for R18, except that 50 nM of human IL-21R fusion protein was used in the third round of selection.

Example 3

Selection of 18A5 and 18G4 Anti-IL-21R scFvs

Anti-IL21R scFvs, 18A5 and 18G4, were isolated by selecting on IL-21R expressing cell lines and IL-21R fusion protein in solution. Transfected hBaf3Mu-1 cells (Wyeth, Giralda Farms, N.J.) expressing the human IL-21R on the cell surface were cultured using standard tissue culture methods. Purified scFv phage ($10^{12}$ tu) were blocked with $1\times10^8$ untransfected Baf3 cells for 1 hour at room temperature in MPBS.

Blocked phage were added to $1\times10^7$ hBaf3Mu-1 cells, which had been pre-incubated in MPBS for 1 hour. This was followed by incubation for one hour at room temperature with mixing. The hBaf3Mu-1 cells were subsequently washed 6 times in PBST. Specifically bound phage were eluted from the cells using 10 μg/ml of trypsin in 0.2 M sodium phosphate buffer, pH 7.0, and incubated at 37° C. for 30 minutes with shaking. The eluted phage supernatant was used to infect *E. coli* TG-1 cells as described above.

ScFv-expressing phage for the second round of selection were produced as described above. Phage were blocked with MPBS and 125 μg/ml control fusion protein. Selection was carried out in solution with biotinylated human IL-21R fusion protein (Wyeth) following selection method described for R18, except that beads were washed 5 times in 1 ml of MPBS/0.1% (v/v) Tween 20 followed by three washes in PBS.

ScFv antibody-expressing phage particles were then further selected using selection method using hBaf3Mu-1 cells, as described above.

Example 4

Selection of CP5G2 Anti-IL-21R scFv

Clone CP5G2 was isolated by selection on murine IL-21R tagged with hexahistidine and a Flag affinity tag (hIL21 R.His.Flag) (Wyeth, Giralda Farms, N.J.). Purified scFv phage ($10^{12}$ tu) were blocked with MPBS plus 30 μl anti-Flag agarose beads for 1 hour at room temperature. hIL-21R.His.Flag, at a final concentration of 25 nM in MPBS, was added to blocked phage and incubated at room temperature for 1 hour. The library/antigen mixture was then added to 100 μl of anti-Flag agarose beads that had been blocked in MPBS for 2 hours at room temperature, washed 3 times in PBS, and incubated a further 30 minutes with mixing. The beads were washed 4 times with PBST, followed by 4 times with PBS and the phage were eluted from the beads with 0.5 μg/ml trypsin in 50 mM Tris, pH 8.0, 1 mM $CaCl_2$, as described above. Beads were collected using centrifugation. Eluted phage were used to infect 10 ml *E. coli* TG-1 cells, as described above. A second round of soluble selection was carried out, also as described above.

Colonies were picked into 96 well plates containing 100 μl of 2TYAG. Crude scFv-containing periplasmic extracts were produced as described above, except the buffer used was 20% (w/v) sucrose, 50 mM Tris-HCl, pH 7.5, 1 mM EDTA. Crude scFv-containing extracts were screened for the ability to inhibit the binding of 16 ng/ml biotinylated murine IL-21 (bio.mIL21) to murine IL-21R protein immobilized on plastic in a 96 well microtitre plate assay. Binding of bio.mIL21 was detected with Europium-labelled streptavidin and TRF detected using the DELFIA reagent kit (PerkinElmer, Boston, Mass.).

Purified CP5G2 scFv exhibited an $IC_{50}$ value of 590 nM in the above assay for inhibition of binding of IL-21 to IL-21R.

Example 5

Identification of $scF_v$'s from MUF and MU11 Phage Clones

To establish the specificity of the $scF_v$'s for IL-21R, a phage ELISA was performed against the IL-21R fusion protein. Individual TG1 cell colonies from the second selection were transferred to microtiter wells containing 100 μl of 2TYAG medium. M13K07 helper phage (10 moi) was added to the exponentially growing TG1 culture, and the samples were incubated for one hour at 37° C. Plates were centrifuged and supernatant was removed, then the remaining pellets were suspended in 100 μl of 2TYAG and incubated overnight at 30° C. with shaking. The next day, plates were centrifuged and phage supernatant was transferred to new microtiter plate wells. Phage was blocked in MPBS prior to ELISA.

Wells of microtiter plates were coated with IL-21R fusion protein or control fusion protein (0.5-2.5 μg/ml) and incubated overnight at 4° C. The next day, fusion protein solution was removed and wells were blocked for 1 hour in MPBS. Wells were washed with PBS, then 50 μl of blocked phage was added. Plates were incubated for 1 hour, then washed 3 times with PBST and 3 times with PBS. Anti-M13-HRP conjugate (Pharmacia, Peapack, N.J.) was added to wells, and the samples were incubated for one hour. Wells were washed 3 times with PBST and 3 times with PBS. TMB was added to wells, and the samples were incubated until color developed. The reaction was stopped with 25 μl of 0.5 M $H_2SO_4$. The color signal was measured by reading absorbance at 450 nm using a microtiter plate reader. Two phage clones showed specific binding to the IL-21R fusion protein and not the control fusion protein, and these clones are referred to in this application as MUF and MU11 phage clones.

Individual TG-1 colonies containing MUF and MU11 phage clones were streaked onto 2TYAG plates and incubated overnight at 30° C. Using pCANTAB6 vector specific oligos, the $V_H$ and $V_L$ regions of the phage were amplified by PCR and sequenced. Database searches revealed that the $V_L$ region of the MUF phage clone originated from lambda chain, and the $V_L$ region of the MU11 phage done originated from kappa chain.

Example 6

Conversion of $scF_v$ to IgG

The $V_H$ and $V_L$ regions from the MUF and MU11 phage clones were amplified by PCR using clone-specific primers. The PCR products were digested with restriction enzymes and subcloned into appropriate vectors (see Example 2) containing the human $IgG_1$ heavy chain constant domain (Takahashi et al. (1982) Cell 29, 671) or the human lambda light chain constant domain or the human kappa light chain constant domain (Hieter et al. (1982) Nature 294: 536). The four constructs encode polypeptides referred to in this application as MUF heavy chain, MUF light chain, MU11 heavy chain, and MU11 light chain.

Vectors containing MUF heavy chain, MUF light chain, MU11 heavy chain, and MU11 light chain, were prepared, sequenced, and used to transfect HEK293 or CHO cells using standard techniques. Cells expressing MUF heavy and light chains produced MUF antibody, which is referred to in this application as "MUF", and cells expressing MU11 heavy and light chains produced MU11 antibody, which is referred to in this application as "MU11." Secreted antibodies were purified using protein A Sepharose (Pharmacia), then dialyzed with PBS.

Binding specificity of antibodies were determined as follows: ELISA plates were coated overnight with 2.5 μg/ml of IL-21R fusion protein. Plates were washed with PBSB (PBS+1% bovine serum albumin), then incubated with various concentrations of MUF or MU11 for 2 hours at 25° C. The plates were washed, then a saturating amount of HRP-conjugated goat anti-human antibody was added. The plates were incubated for 1 hour at 25° C., then washed with PBSB, and developed with using TMB. An example of the results obtained by the ELISA is presented in FIG. 1A.

Figure 1B:
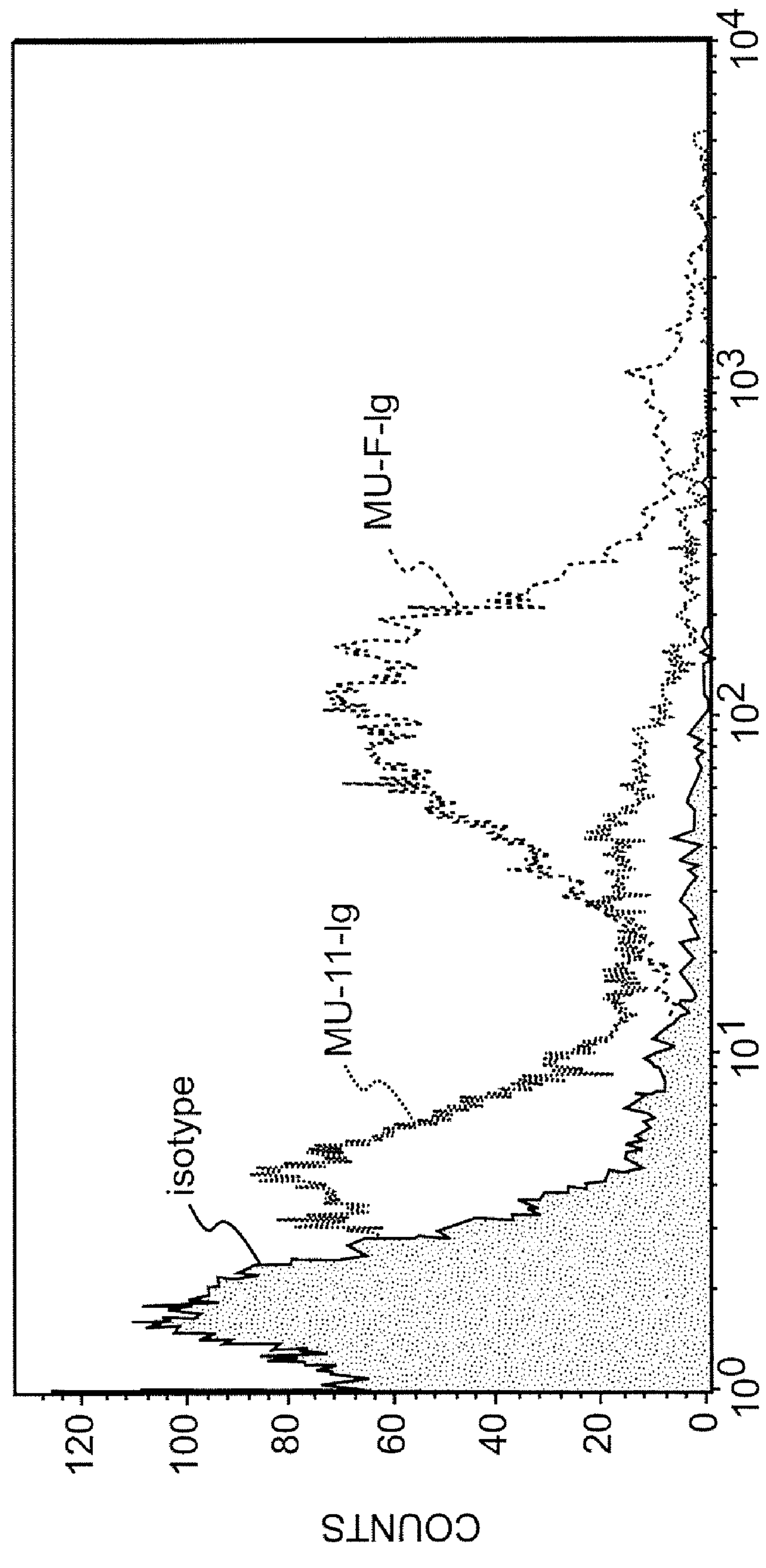
FIG. 1B depicts the result of a binding assay analyzed by FACS which shows that both MUF and MU11 bind on the surface of human IL-21R.
Figure 1C:
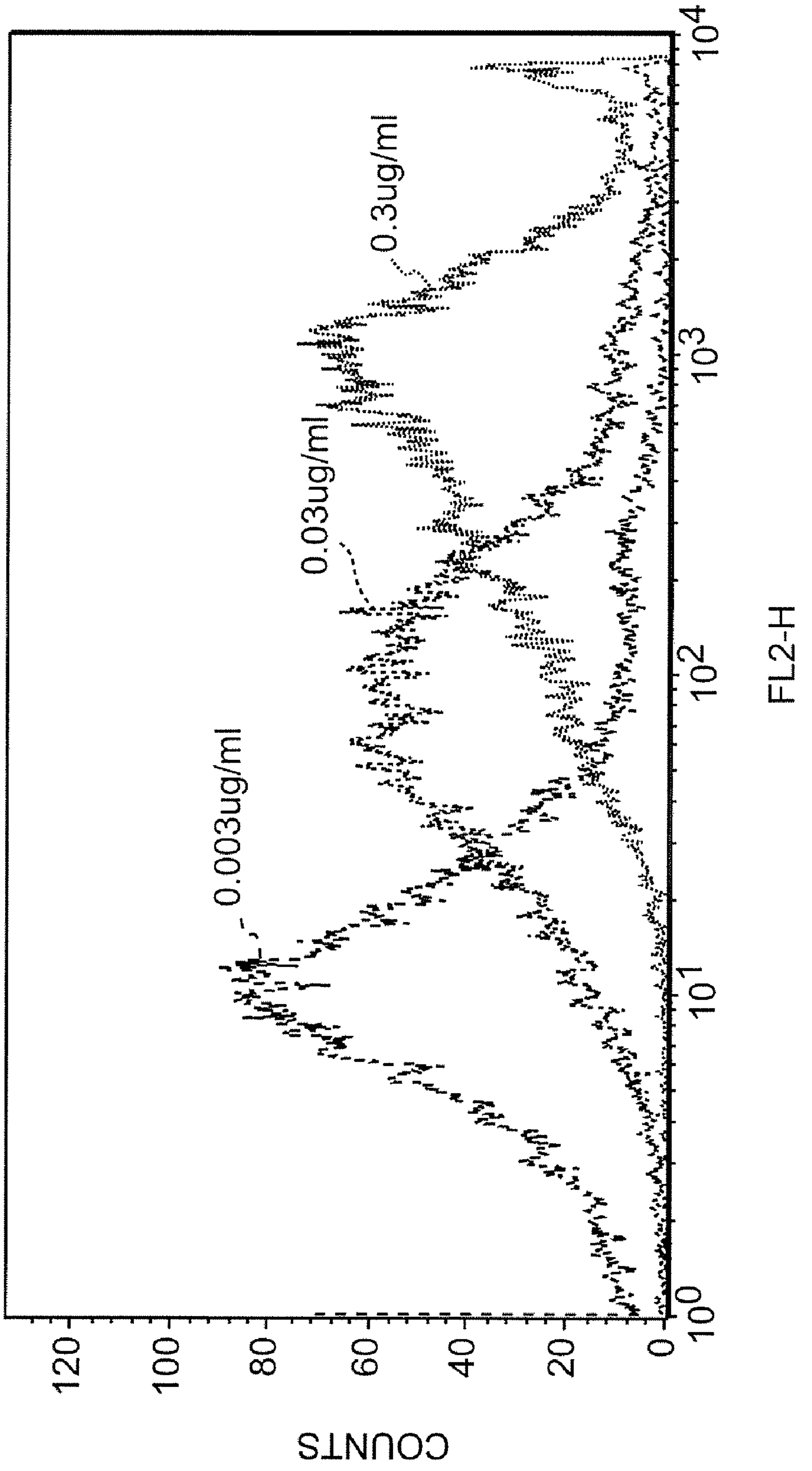
FIG. 1C depicts the result of a binding assay analyzed by FACS which shows that MUF binds IL-21R on mouse B cells.

Binding specificity of the antibodies was further confirmed by cell surface staining. Human IL-21R transduced TF-1 cells were bound with purified or biotinylated MUF or MU11 (1 mg/ml). Cells were incubated on ice for 30 minutes, washed with PBSB, then suspended in a solution containing PE-conjugated anti-human IgG antibody or PE-conjugated avidin. Cells were incubated on ice for 30 minutes, washed, then analyzed on a FACScan. The results are presented in FIG. 1B. Purified mouse B cells were similarly stained with MUF, and the results are presented in FIG. 1C.

Example 7

MUF Blocks Binding of IL-21 to IL-21R

Figure 2:
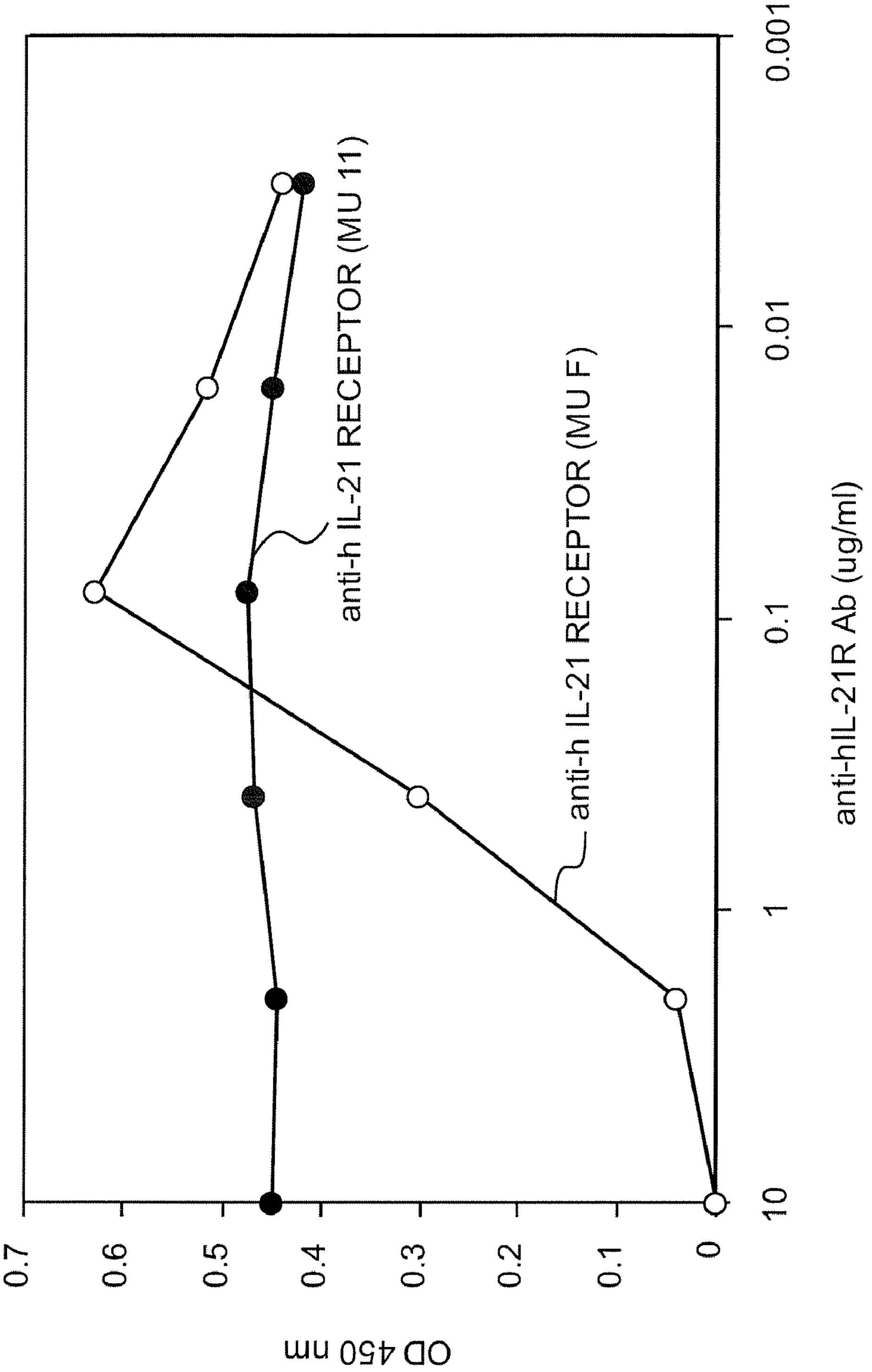
FIG. 2 depicts the result of an ELISA which shows that MUF inhibits the binding of human IL-21 to human IL-21R.

Inhibition assays were performed to assess the ability of the antibodies to block binding of IL-21 to IL-21R. The ELISA was performed as described in Example 3 with the following modifications. After incubation with MUF or MU11 for 2 hours at 25° C., biotin-conjugated IL-21 (1 μg/ml) was added, and the samples were incubated for 1 hour at 25° C. After washing, saturating amount of avidin-HRP was added, and the samples were further incubated for 1 hour at 25° C. The wells were washed with PBSB, and the samples were developed using TMB. Results are presented in FIG. 2. Under these conditions, MUF blocked the binding of IL-21 to IL-21R, whereas MU11 did not. These data suggest that MUF and MU11 recognize different epitopes of IL-21R.

Example 8

MUF and MU11 Decrease T Cell Responses

Figure 3A:
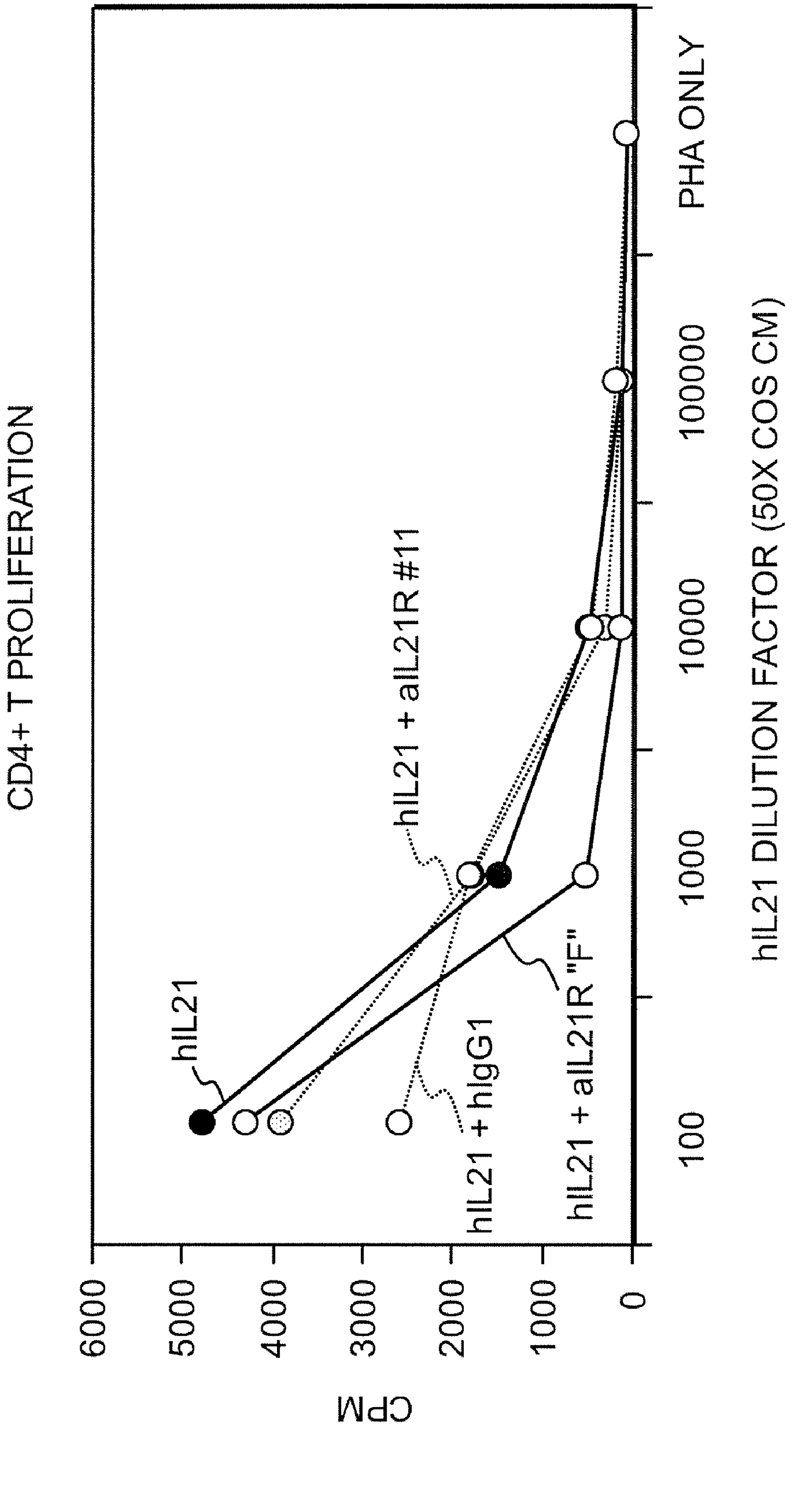
FIG. 3A depicts the result of a cell-proliferation assay which shows that addition of MUF blocked the ability of IL-21 to increase the proliferation of human CD4+ T cells.

Proliferation assays were performed to assess the antibody's ability to block the IL-21 mediated T cell proliferation. Human CD4+ T cells ($5\times10^4$ cells/well) were stimulated with PHA (phytohemagglutinin) and human IL-21. IL-21 in COS cell culture media (COS CM) was added to different samples at various concentrations. In indicated samples, MUF, MU11, or human $IgG_1$ isotype control were added. After 72 hours, $^3$H-thymidine was added, and cell proliferation was measured by incorporated radioactivity using a LKB 1205 liquid scintillation counter. As shown in FIG. 3A, IL-21 increased the proliferation of PHA-stimulated T cells. Addition of MUF blocked the ability of IL-21 to increase proliferation in the range between about 1:500 and 1:10,000. MUF blockage was overcome at higher doses of IL-21. Addition of MU11 or isotype control antibody did not significantly affect IL-21 augmented proliferation of human T cells.

Figure 3B:
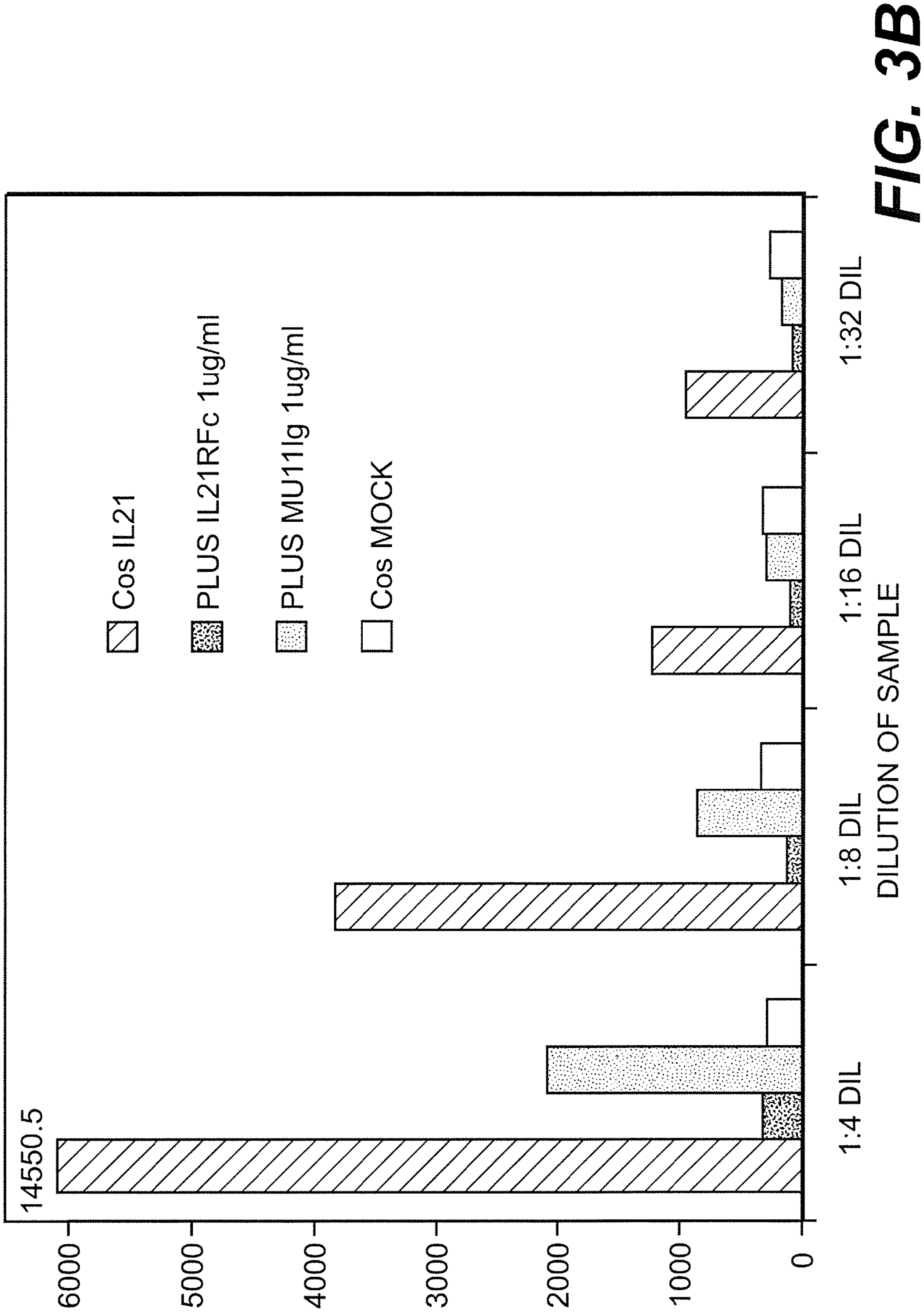
FIG. 3B depicts the result of a cell-proliferation assay which shows that MU11 blocked the ability of IL-21 in COS cell culture media to increase the proliferation of mouse CD4+ T cells.

In FIG. 3B, a PLP-specific mouse CD4+ T cell line was stimulated with PLP peptide (1 μg/ml) and SJL mouse spleen cells. IL-21 in COS cell culture media (COS IL-21) was titered as shown on the X-axis. "Cos Mock" is COS culture medium without IL-21. In indicated samples, MU11 (1 μg/ml) was added. After 72 hours, $^3$H-thymidine was added, and proliferation was measured by incorporated radioactivity. As shown in FIG. 3B, IL-21 increased the proliferation of stimulated mouse T cells. Addition MU11 blocked the ability of IL-21 to increase proliferation of mouse CD4+ T cells. These data suggest that MU11 acts as a non-competitive inhibitor: it blocks IL-21's ability to increase proliferation even though it does not block IL-21 binding to the receptor.

Figure 3C:
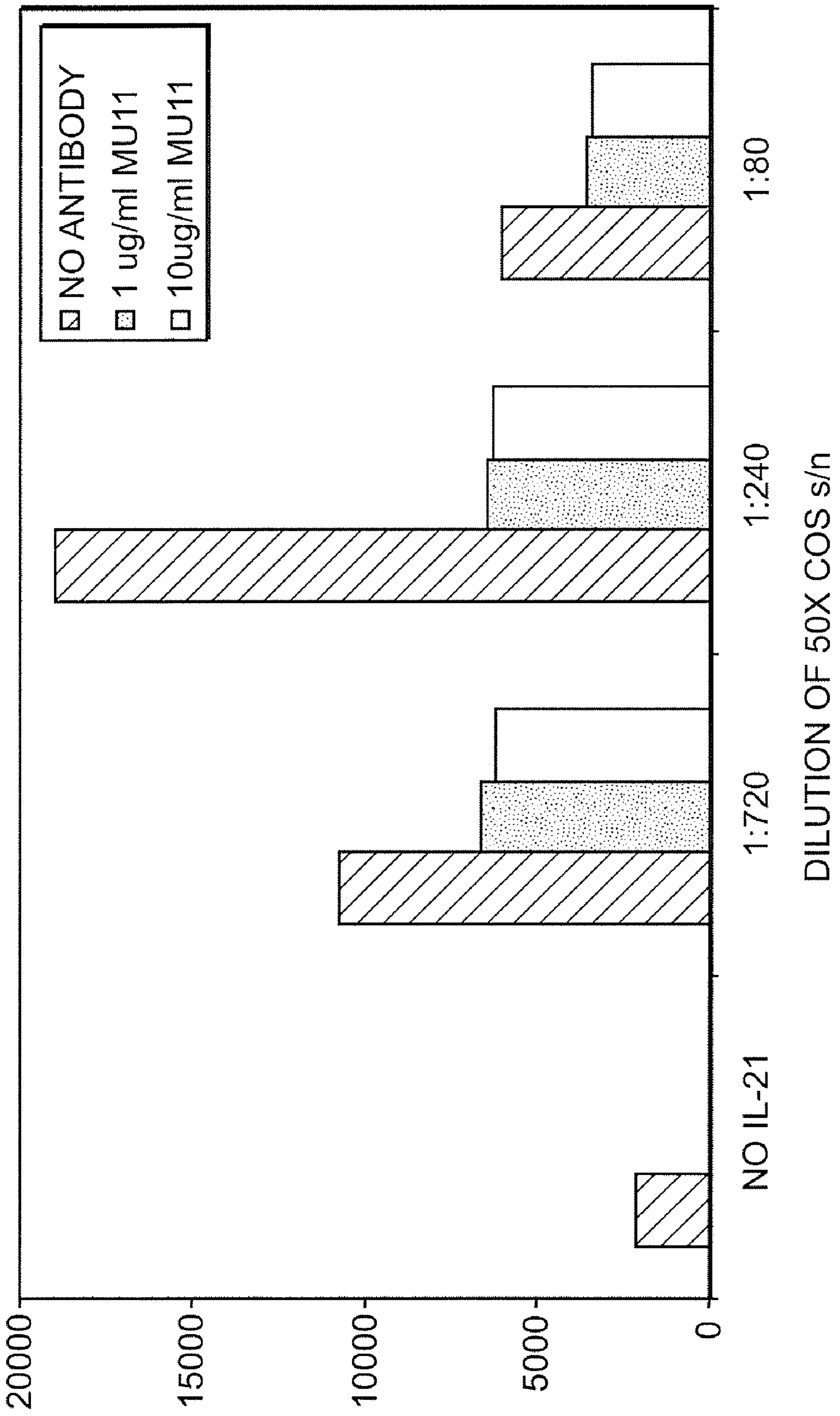
FIG. 3C depicts the result of a cell-proliferation assay which shows that MU11 blocked the ability of IL-21 in COS cell culture media to increase the proliferation of mouse CD8+ T cells, in a dose-dependent manner.

In FIG. 3C, purified CD8+ mouse T cells were stimulated with tosyl-beads (Dynal, Great Neck, N.Y.) coated with anti-CD3 antibody. IL-21 in COS cell culture media (COS s/n) was titered as indicated in the X-axis. The sample labeled "no antibody" was used as a control. In indicated samples, MU11 was added at the marked concentration. After 72 hours, $^3$H-thymidine was added, and proliferation was measured by incorporated radioactivity. As shown in FIG. 3C, the addition of MU11 blocked, in a dose dependent manner, the ability of IL-21 to increase the proliferation of CD8+ T cells.

Example 9

Inhibition of Cell Proliferation by scFvs and IgGs

Antibodies of the invention were tested in a cell-based assay for IL-21R antagonism. In one such experiment, various scFv phage clones that were isolated as described in Examples 1-3, were tested in a cell-based assay for their potency to inhibit cell-proliferation by blocking IL-21 binding to IL-21R. A hBaf3Mu-1 cell suspension expressing human IL21 R was used for such an assay. hBaf3Mu-1 cells (Wyeth) were washed to remove traces of murine IL-3 from their growth medium and incubated for 2 hours in growth RPMI Glutamax with 10% fetal bovine serum without IL-3 at 37° C. in a 5% $CO_2$ incubator. About 10,000 to 20,000 Baf3Mu-1 cells were added to each well of a 96-well tissue culture plate and then incubated with an scFv or IgG for 30 minutes at 37° C. IL-21 (Wyeth, Giralda Farms, N.J.) was then added to a concentration of 5 ng/ml and the cells were incubated for 24 hours. Cells were then pulse-labeled with 0.1 mCi/well $^3$H thymidine overnight at 37° C. and subsequently harvested to measure thymidine incorporation as an indication of proliferation of cells. An alternative protocol, IL-21 was added to a concentration of 0.3 ng/ml and the cells were incubated for 48 hours. Cells were then warmed to room temperature, and 15 ml/well CellTiter-Glo (Promega, Wis.) were added. After mixing and a 10 minute incubation period, luminescence was measured on a Wallac MicroBeta 1450 TriLux counter (PerkinElmer, Boston, Mass.) as an indication of cell proliferation or viability.

Figure 4:
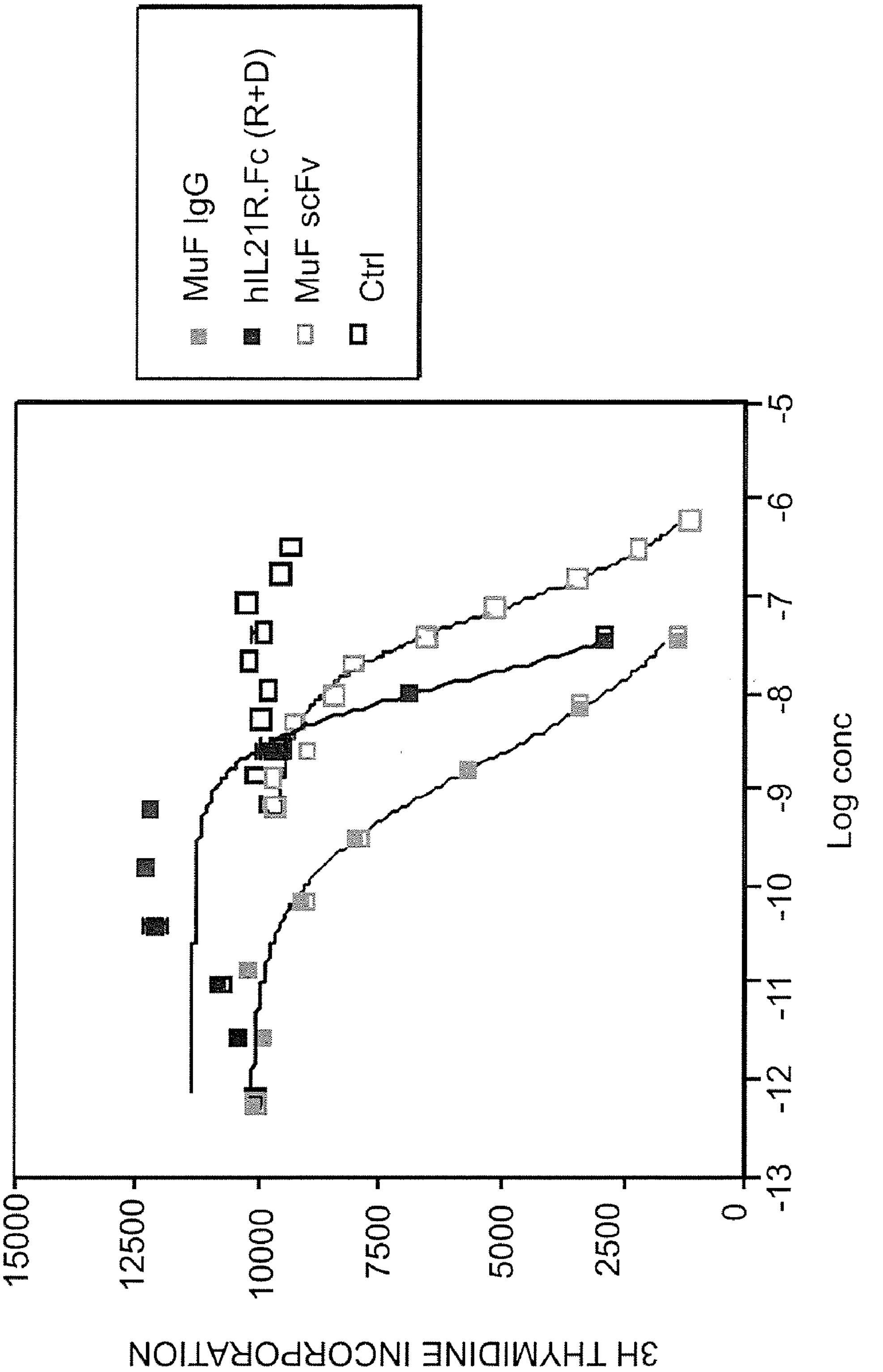
FIG. 4 depicts the result of a cell-proliferation assay which shows that both MUF scFv and MUF IgG blocked the ability of IL-21 to increase the proliferation of Baf3Mu-1 cells which express an IL-21R.

An $IC_{50}$ value (i.e., concentration of an antibody required for 50% competition) for each scFv can be determined by plotting a measure of cell proliferation, e.g., thymidine incorporation, against the log concentration of IL-21. Typically, the lower an $IC_{50}$, the better affinity an antibody has for IL-21R. In one experiment depicted in FIG. 4, MUF inhibited cell response to IL-21 with an $IC_{50}$ of 268 nM as an scFv and 3 nM as an IgG. The $IC_{50}$ values of other scFv clones were subsequently compared with that of MUF, as summarized in Table 4 below.

TABLE 4

$IC_{50}$ values of various scFvs

| Clone | $IC_{50}$ Value (nM) ScFv |
|---|---|
| MUF | 140 |
| hIL21R18 | 473 |
| 18A5 | 213 |
| 18G4 | 522 |
| 19F5 | 91 |
| CP5G2 | 329 |

Example 10

MUF Germlining

Sequence data for the scFv clones was used to identify the nearest germline sequence for the heavy and light chain of the MUF clone using VBASE. Mutations were made using standard site directed mutagenesis techniques with the appropriate mutagenic primers. Mutation of scFv sequences was confirmed by sequence analysis. Germlined scFv and $V_H$ and $V_L$ domain sequences for MUF are set forth in SEQ ID NO:85, 83 and 84, respectively.

The MUF scFv germlined sequence was subsequently assayed for its ability to block IL-21 induced hBaf3Mu-1 cell line proliferation in the assay described herein. There was no significant difference in the potency of the germlined MUF to block Baf3Mu-1 cell proliferation when compared to the non-germlined MUF scFv.

Example 11

Epitope Competition Assay

The scFv clones 18A5, 19F5 and 18G4 were further tested in an epitope competition assay in order to determine whether they bound the same or a different epitope than MUF. ScFv-containing periplasmic extracts were prepared as described above for the various clones. Final buffer used was 50 mM MOPS, pH 7.4, 0.5 mM EDTA, 0.5 M sorbitol. The scFv-containing crude periplasmic extracts were screened for the ability to inhibit the binding of biotinylated human IL-21R fusion protein (bio.hIL21R) to MuF IgG protein immobilized on plastic in a 96 well microtitre plate assay. Binding of bio.hIL21R was detected with Europium-labelled streptavidin and TRF detected using the DELFIA reagent kit (PerkinElmer). Positive clones were used in an epiope competition assay described herein.

The $IC_{50}$ values obtained for the various clones in the epitope competition assay are summarized in Table 5.

TABLE 5

Epitope Competition Assay

| Clone | $IC_{50}$ (nM) |
|---|---|
| MUF IgG | 0.4 |
| negative control | 0.0 |
| 18A5 | 114 |
| 18G4 | 1.4 |
| 19F5 | weak inhibition |

Example 12

Treatment of Arthritis

IL-21 was used to study its effect on cells from the synovial membrane, the membrane that lines the joints. Human fibroblast-like synoviocytes (HFLS) (Cell Applications (San Diego, Calif.)) were isolated from synovial tissues of rheumatoid arthritis patients undergoing joint surgery. HFLS cells were cultured with human IL-21 for 48 hours, and the supernatants were removed and tested for chemokines MCP-1 (monocyte chemoattractant protein or CCL11), GRO (growth-regulated oncogene or CXC ligand 1), I-309 (CCL1), TARC (thymus and activation-regulated chemokine), Eotaxin, MDC (macrophage-derived chemokine or CCL22), LYMPH (lymphotactin or XCL1), SDF-1B (stromal derived factor-1B or CXC ligand 12), IP-10 (CXC ligand 10), I-TAC (T-cell attracting chemokine or CXC ligand 11), MG (monokine induced by interferon or CXC ligand 9), MP3B (macrophage inhibitory protein) and cytokines IFN-α, TNF-α, IL-6, and IL-8 by ELISA. These chemokines and cytokines are known in the art to promote inflammation through a number of activities, and increased concentrations in the joints caused by IL-21 exacerbates inflammation and RA.

Figure 5B:
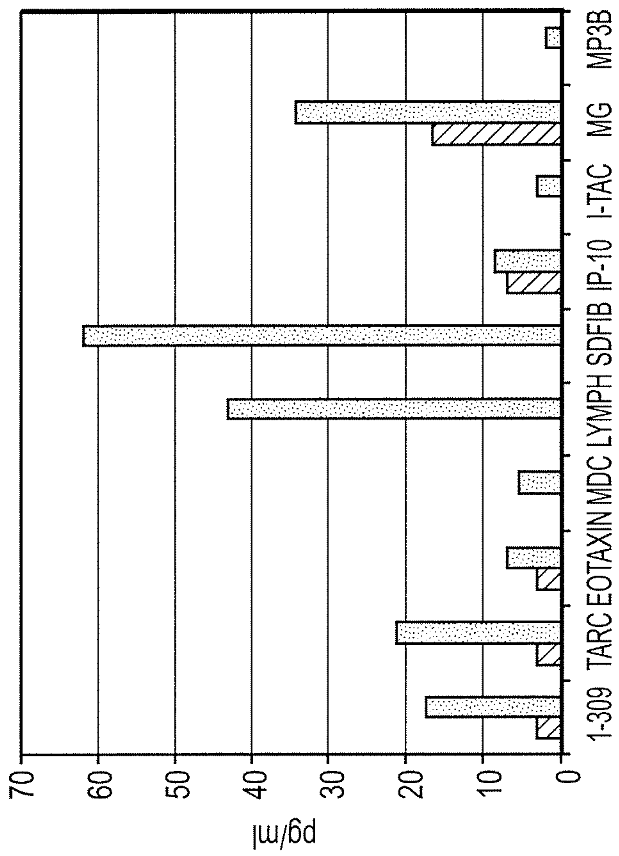
FIG. 5B depicts that addition of IL-21 to human fibroblast-like synoviocytes isolated from arthritis patients leads to an increase in the secretion of chemokines 1-309, TARC, Eotaxin, MDC, Lymph, SDFIB, IP-10, I-TAC, MG and MP3B.
Figure 5A:
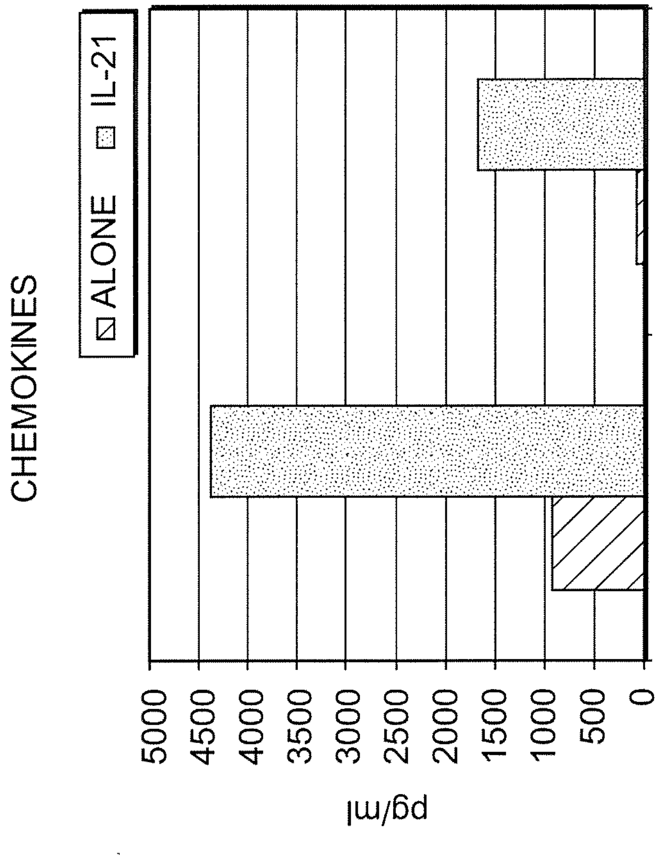
FIG. 5A depicts that addition of IL-21 to human fibroblast-like synoviocytes isolated from arthritis patients leads to an increase in the secretion of chemokines MCP-1 and GRO.
Figure 5C:
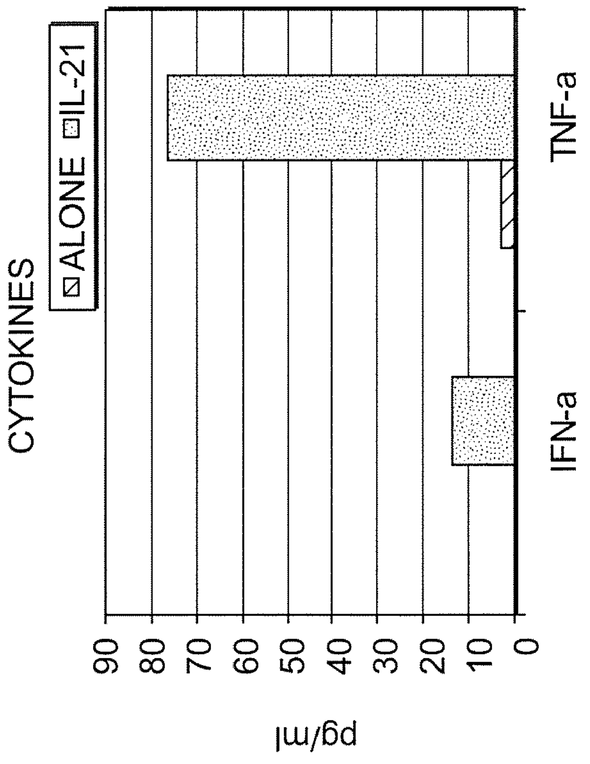
FIGS. 5C and 5D depict that addition of IL-21 to human fibroblast-like synoviocytes isolated from arthritis patients leads to an increase in the secretion of cytokines IFN-alpha and TNF-alpha (FIG. 5C) and IL-6 and IL8 (FIG. 5D).
Figure 5D:
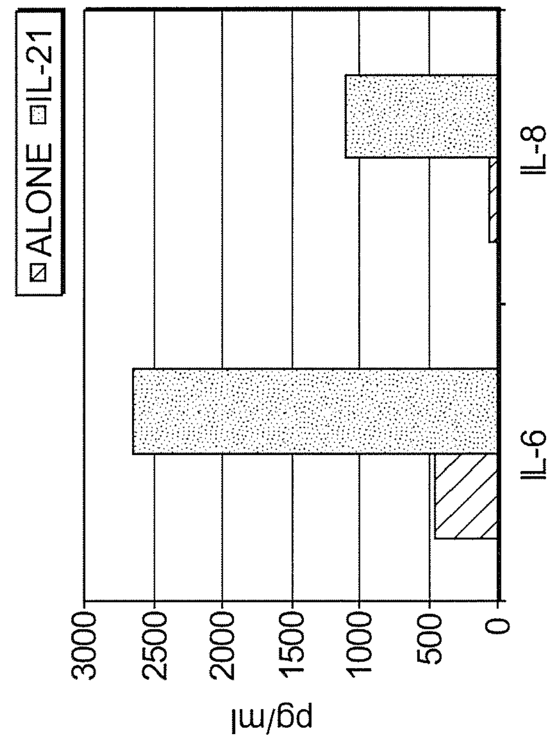
Figure 5E:
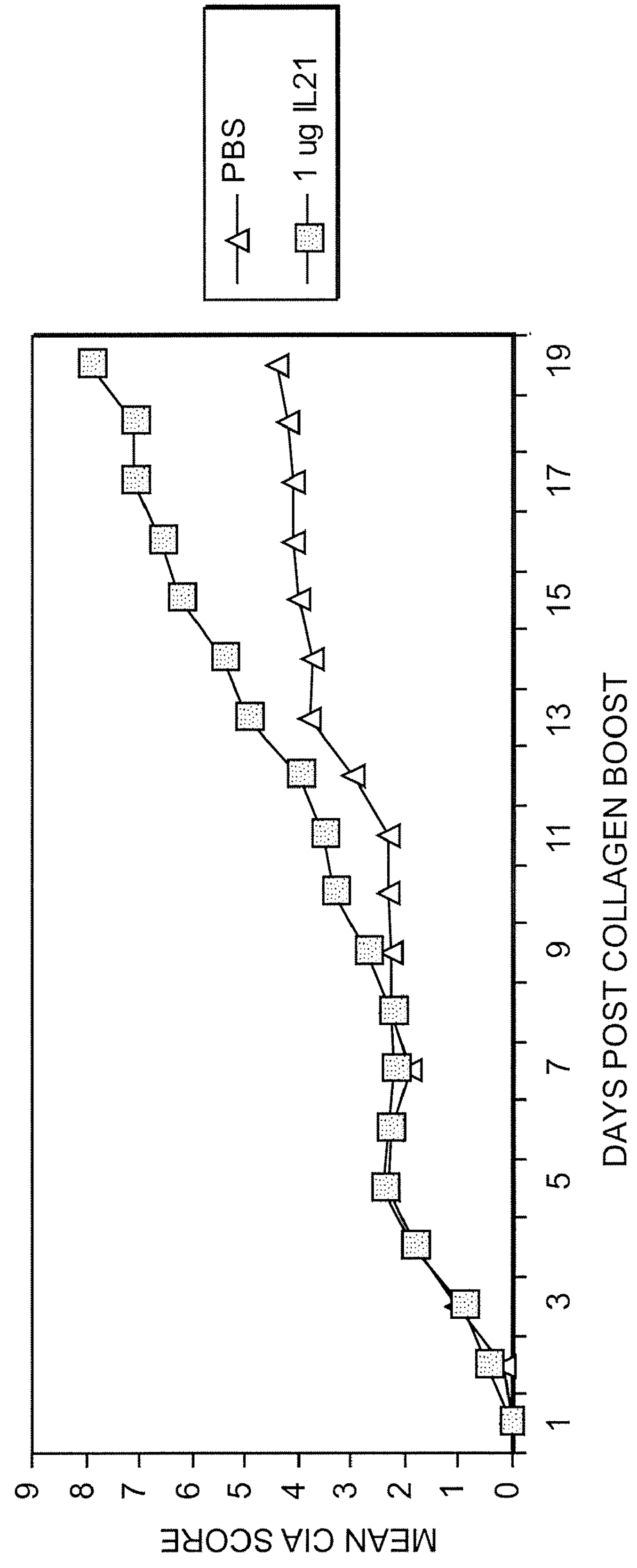
FIG. 5E shows that IL-21 exacerbates collagen induced arthritis (CIA) in a mouse model for arthritis, as measured by the indicia for CIA.

As shown in FIGS. 5A-5D, IL-21 repeatedly increased HFLS secretion of chemokines MCP-1, GRO, 1-309, TARC, Eotaxin, MDC, LYMPH, SDF-1B, IP-10, I-TAC, MG, MP3B and cytokines cytokines IFN-α, TNF-α, IL-6, and IL-8. IL-21 was used to regulate the clinical progression of CIA (Collagen Induced Arthritis). CIA is the standard mouse and rat model for studying rheumatoid arthritis, see e.g., Holmdahl et al., (2002) Ageing Res. Rev., 1:135. On day 0, mice were injected with 100 μg of Collagen Type II in complete Freund's adjuvant, and on day 21, the mice were boosted with 100 μg of Collagen Type II in incomplete Freund's adjuvant. On day 21, the mice were also injected daily with 1 μg of IL-21, and each day, the mice were examined for disease. The clinical signs were scored as follows: 0=no swelling, 1=1 to 2 swollen digits or swollen ankle, 2=more than 2 swollen digits or mild paw swelling, 3=extensive paw swelling, and 4=ankylosis of paw. As shown in FIG. 5E, mice injected with PBS after the collagen injections progressively developed disease. Mice injected with IL-21 after the collagen injections progressively developed more severe disease. Because treatment with IL-21 specifically exacerbates CIA, treatment with anti-IL-21R antibodies is expected to suppress or delay CIA. Thus, since this model predicts treatment efficacy for RA, treatment with anti-IL-21R antibodies would also be expected to suppress or delay RA in humans.

Example 13

Treatment of Transplant Rejection

Transplant rejection is the immunological phenomenon where tissues from a donor are specifically "attacked" by immune cells of the host. One assay to study transplant rejection in vitro is the mixed lymphocyte reaction (MLR). In the MLR assay, "donor" cells and "host" cells are mixed in vitro, and the host cells become activated and proliferate. Between day 3 and 5, $^3$H-thymidine is added, and proliferation is measured by incorporated radioactivity using a liquid scintillation counter.

Figure 6:
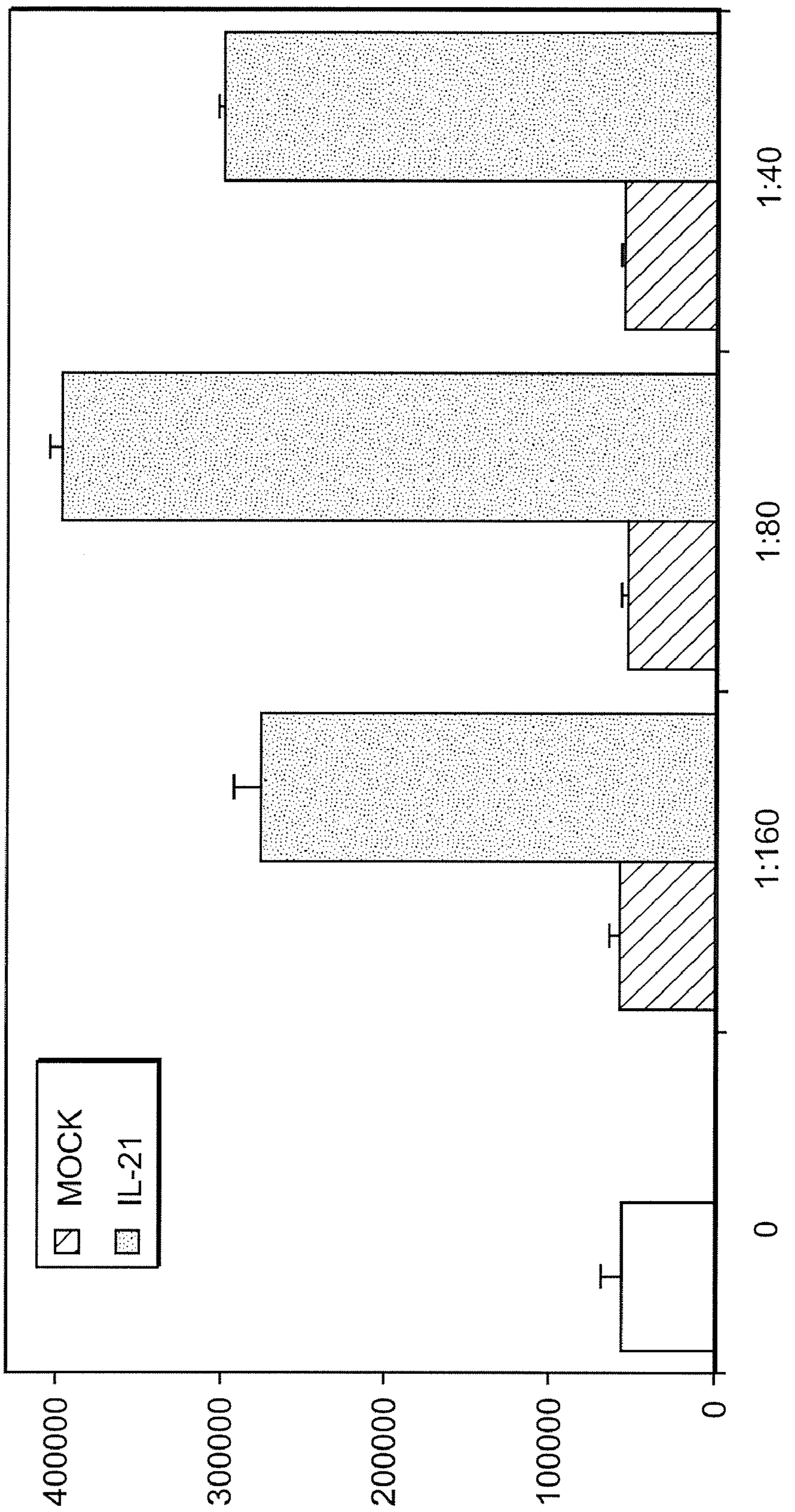
FIG. 6 shows that IL-21 increases the proliferation of C57BL/6J cells in a mixed lymphocyte reaction, an in vitro model for transplant rejection.

In FIG. 6, C57BL/6J mouse spleen cells (500,000) and irradiated BDF1 mouse spleen cells (500,000) were suspended in 200 μl of culture media in a microtiter plate well. Three duplicate wells were supplemented with different amounts of mouse IL-21. On day 4, $^3$H-thymidine was added, and day 5, incorporated radioactivity was measured using a LKB 1205 liquid scintillation counter. Samples "0" and "mock" indicate cultures without IL-21. In the absence of IL-21, C57BL/6J cells proliferated modestly (~6000 rads). In the presence of IL-21, C57BL/6J cells proliferated more strongly (~28,000-38,000 rads). Treatment with IL-21 augments the proliferation of C57BL/6J cells (the "host" or alloreactive cells), suggesting that IL-21 mediates MLR. Addition or treatment with anti-IL-21R antibodies is, therefore, expected to suppress or delay MLR and transplant rejection and related diseases (e.g., graft versus host disease).

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

We claim:

1. An isolated nucleic acid encoding an antibody comprising an amino acid sequence that is at least 95% identical to an amino acid sequence selected from the group consisting of SEQ ID NOs:65, 66, and 67, wherein the antibody selectively binds to an extracellular domain of a human or a mouse IL-21 receptor.

2. An expression vector comprising the nucleic acid of claim 1.

3. A host cell transformed with the vector of claim 2.

4. The host cell of claim 3, wherein the host cell is a bacterial, mammalian, yeast, plant, or insect cell.

5. A method of generating an antibody or antigen-binding fragment that binds to an extracellular domain of a human or a mouse IL-21 receptor comprising:

(a) providing a repertoire of nucleic acids encoding a $V_H$ domain that either includes a CDR 1, 2 and 3 to be replaced or lacks a CDR 1, 2 and 3 encoding region;

(b) combining the repertoire with donor nucleic acids encoding amino acid sequences set forth in SEQ ID NOs:68, 69, and 70, such that the donor nucleic acids are inserted into the CDR 1, 2 and 3 region in the repertoire, so as to provide a product repertoire of nucleic acids encoding a $V_H$ domain;

(c) expressing the nucleic acids of the product repertoire; and (d) selecting an antibody or antigen-binding fragment expressed from the product repertoire of nucleic acids, wherein the antibody or antigen-binding fragment is specific for the extracellular domain of the IL-21 receptor.

6. A method of generating an antibody or antigen-binding fragment that binds to an extracellular domain of a human or a mouse IL-21 receptor comprising:

(a) providing a repertoire of nucleic acids encoding a variable domain that either includes a $V_L$ to be replaced, or lacks a $V_L$ encoding region;

(b) combining the repertoire with a donor nucleic acid encoding the amino acid sequence set forth in SEQ ID NO:66, such that the donor nucleic acid is inserted into the $V_L$ region in the repertoire, so as to provide a product repertoire of nucleic acids encoding a variable domain;

(c) expressing the nucleic acids of the product repertoire; and (d) selecting an antibody or antigen-binding fragment expressed from the product repertoire of nucleic acids, wherein the antibody or antigen-binding fragment is specific for the extracellular domain of the IL-21 receptor.

7. A method of generating an antibody or antigen-binding fragment that binds to an extracellular domain of a human or a mouse IL-21 receptor comprising:

(a) providing a repertoire of nucleic acids encoding a $V_L$ domain that either includes a CDR 1, 2 and 3 to be replaced or lacks a CDR 1, 2 and 3 encoding region;

(b) combining the repertoire with donor nucleic acids encoding amino acid sequences set forth in SEQ ID NOs:71, 72, and 73, such that the donor nucleic acids are inserted into the CDR 1, 2 and 3 region in the repertoire, so as to provide a product repertoire of nucleic acids encoding a $V_L$ domain;

(c) expressing the nucleic acids of the product repertoire; and (d) selecting an antibody or antigen-binding fragment expressed from the product repertoire of nucleic acids, wherein the antibody or antigen-binding fragment is specific for the extracellular domain of the IL-21 receptor.

8. A method of generating an antibody or antigen-binding fragment that binds to an extracellular domain of a human or a mouse IL-21 receptor comprising:

(a) providing a repertoire of nucleic acids encoding a variable domain that either includes a $V_H$ to be replaced, or lacks a $V_H$ encoding region;

(b) combining the repertoire with a donor nucleic acid encoding the amino acid sequence set forth in SEQ ID NO:65, such that the donor nucleic acid is inserted into the $V_H$ region in the repertoire, so as to provide a product repertoire of nucleic acids encoding a variable domain;

(c) expressing the nucleic acids of the product repertoire; and (d) selecting an antibody or antigen-binding fragment expressed from the product repertoire of nucleic acids, wherein the antibody or antigen-binding fragment is specific for the extracellular domain of the IL-21 receptor.

9. The method of any one of claims 5-7, further comprising the step of germlining.

10. An isolated nucleic acid encoding an antibody comprising a $V_H$ domain having an amino acid sequence that is at least 95% identical to an amino acid sequence set forth as SEQ ID NO:65, and a $V_L$ domain having an amino acid sequence that is at least 95% identical to an amino acid sequence set forth as SEQ ID NO:66, wherein the antibody selectively binds to an extracellular domain of a human or a mouse IL-21 receptor.

11. An isolated nucleic acid encoding an antibody comprising a $V_H$ domain that comprises:

(a) CDR sequences set forth in SEQ ID NOs:68, 69, and 70, or (b) conservative amino acid substitutions thereof, wherein the $V_H$ domain comprises CDR sequences with one conservative amino acid substitution of SEQ ID NO:68, two or less conservative amino acid substitutions of SEQ ID NO:69, and/or one conservative amino acid substitution of SEQ ID NO:70, wherein the antibody selectively binds an extracellular domain of a human or a mouse IL-21 receptor.

12. An isolated nucleic acid encoding an antibody comprising a $V_L$ domain that comprises:

(a) CDR sequences set forth in SEQ ID NOs:71, 72, and 73, or (b) conservative amino acid substitutions thereof, wherein the $V_L$ domain comprises CDR sequences with two or less conservative amino acid substitutions of SEQ ID NO:71, one conservative amino acid substitution of SEQ ID NO:72, and/or two or less conservative amino acid substitutions of SEQ ID NO:73, wherein the antibody selectively binds an extracellular domain of a human or a mouse IL-21 receptor.

* * * * *

SEQUENCE LISTING

```
<160> NUMBER OF SEQ ID NOS: 154

<210> SEQ ID NO 1
<211> LENGTH: 113
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Asn Ile Tyr
            20                  25                  30

Ser Val Ser Trp Val Arg Gln Ala Pro Gly Gln Gly Leu Glu Trp Met
        35                  40                  45

Gly Arg Ile Ile Pro Met Arg Asp Ile Ala Asn Tyr Ala Gln Arg Phe
    50                  55                  60

Gln Gly Arg Val Thr Leu Thr Ala Asp Lys Ser Ser Gly Thr Ala Tyr
65                  70                  75                  80

Met Glu Leu Arg Gly Leu Arg Ser Asp Asp Thr Ala Val Tyr Trp Cys
                85                  90                  95

Ala Thr Leu Ala Gly Pro Leu Asp Ser Trp Gly Gln Gly Thr Leu Val
            100                 105                 110

Thr


<210> SEQ ID NO 2
<211> LENGTH: 113
<212> TYPE: PRT
```

-continued

<213> ORGANISM: Homo sapiens

<400> SEQUENCE: 2

```
Ser Ser Glu Leu Thr Gln Asp Pro Ala Val Ser Val Gly Leu Gly Gln
  1               5                  10                  15

Thr Val Thr Ile Thr Cys Gln Gly Gly Ser Leu Arg Gln Tyr Tyr Ala
             20                  25                  30

Ser Trp Tyr Gln Gln Lys Pro Gly Gln Ala Pro Val Val Val Ile Tyr
         35                  40                  45

Gly Lys Asn Lys Arg Pro Ser Gly Ile Pro Asp Arg Phe Ser Gly Thr
     50                  55                  60

Thr Ser Gly Asn Thr Ala Ser Leu Thr Ile Thr Gly Ala Gln Ala Glu
 65                  70                  75                  80

Asp Glu Ala Asp Tyr Tyr Cys Lys Ser Arg Asp Ser Ser Gly Asn His
                 85                  90                  95

Pro Leu Tyr Val Phe Gly Ala Gly Thr Lys Leu Thr Val Leu Gly Glu
            100                 105                 110

Ser
```

<210> SEQ ID NO 3
<211> LENGTH: 253
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ser
  1               5                  10                  15

Ser Val Arg Val Ser Cys Lys Ala Ser Gly Gly Thr Phe Asn Ile Tyr
             20                  25                  30

Ser Val Ser Trp Val Arg Gln Ala Pro Gly Gln Gly Leu Glu Trp Met
         35                  40                  45

Gly Arg Ile Ile Pro Met Arg Asp Ile Ala Asn Tyr Ala Gln Arg Phe
     50                  55                  60

Gln Gly Arg Val Thr Leu Thr Ala Asp Lys Ser Ser Gly Thr Ala Tyr
 65                  70                  75                  80

Met Glu Leu Arg Gly Leu Arg Ser Asp Asp Thr Ala Val Tyr Trp Cys
                 85                  90                  95

Ala Thr Leu Ala Gly Pro Leu Asp Ser Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ala Leu Ser Ser Glu Leu Thr Gln Asp Pro Ala Val Ser
    130                 135                 140

Val Gly Leu Gly Gln Thr Val Thr Ile Thr Cys Gln Gly Gly Ser Leu
145                 150                 155                 160

Arg Gln Tyr Tyr Ala Ser Trp Tyr Gln Gln Lys Pro Gly Gln Ala Pro
                165                 170                 175

Val Val Val Ile Tyr Gly Lys Asn Lys Arg Pro Ser Gly Ile Pro Asp
            180                 185                 190

Arg Phe Ser Gly Thr Thr Ser Gly Asn Thr Ala Ser Leu Thr Ile Thr
        195                 200                 205

Gly Ala Gln Ala Glu Asp Glu Ala Asp Tyr Tyr Cys Lys Ser Arg Asp
    210                 215                 220

Ser Ser Gly Asn His Pro Leu Tyr Val Phe Gly Ala Gly Thr Lys Leu
225                 230                 235                 240
```

-continued

```
Thr Val Leu Gly Ala Ala Ala His His His His His His
                245                 250


<210> SEQ ID NO 4
<211> LENGTH: 5
<212> TYPE: PRT
<213> ORGANISM: Homo sapiens

<400> SEQUENCE: 4

Ile Tyr Ser Val Ser
  1               5


<210> SEQ ID NO 5
<211> LENGTH: 17
<212> TYPE: PRT
<213> ORGANISM: Homo sapiens

<400> SEQUENCE: 5

Arg Ile Ile Pro Met Arg Asp Ile Ala Asn Tyr Ala Gln Arg Phe Gln
  1               5                  10                  15

Gly


<210> SEQ ID NO 6
<211> LENGTH: 7
<212> TYPE: PRT
<213> ORGANISM: Homo sapiens

<400> SEQUENCE: 6

Leu Ala Gly Pro Leu Asp Ser
  1               5


<210> SEQ ID NO 7
<211> LENGTH: 11
<212> TYPE: PRT
<213> ORGANISM: Homo sapiens

<400> SEQUENCE: 7

Gln Gly Gly Ser Leu Arg Gln Tyr Tyr Ala Ser
  1               5                  10


<210> SEQ ID NO 8
<211> LENGTH: 7
<212> TYPE: PRT
<213> ORGANISM: Homo sapiens

<400> SEQUENCE: 8

Gly Lys Asn Lys Arg Pro Ser
  1               5


<210> SEQ ID NO 9
<211> LENGTH: 13
<212> TYPE: PRT
<213> ORGANISM: Homo sapiens

<400> SEQUENCE: 9

Lys Ser Arg Asp Ser Ser Gly Asn His Pro Leu Tyr Val
  1               5                  10


<210> SEQ ID NO 10
<211> LENGTH: 339
<212> TYPE: DNA
<213> ORGANISM: Homo sapiens

<400> SEQUENCE: 10

caggtccagc tggtgcagtc tggggctgag gtgaagaagc ctgggtcctc ggtgagggtc     60
```

-continued tcctgcaagg cttctggagg caccttcaac atctatagtg tcagctgggt gcgacaggcc 120
cctggacagg ggcttgagtg gatgggaagg atcatcccta tgcgtgatat tgcaaactac 180
gcgcagaggt tccagggcag ggtcacactt accgcggaca agtcctcggg gacagcctac 240
atggagttgc gcggcctgag atctgacgac acggccgtct attggtgtgc gacattggct 300 ggcccccttgg actcctgggg ccagggcacc ctggtcacc 339

<210> SEQ ID NO 11
<211> LENGTH: 339
<212> TYPE: DNA
<213> ORGANISM: Homo sapiens

<400> SEQUENCE: 11
tcgtctgagc tgactcagga cccagctgtg tctgtgggct tgggacagac agtcacgatc 60
acatgtcaag gcggcagcct cagacaatat tatgcaagtt ggtaccaaca gaagccagga 120
caggcccctg tggttgtcat ctatggtaaa aataagcgac cctcagggat cccagaccga 180
ttctctggca ccacctcagg caacacagct tccttgacca tcactggggc tcaggcggaa 240
gatgaggctg actactattg taagtcccgg gacagcagtg gtaaccatcc cctttatgtc 300
ttcggagcag ggaccaagct gaccgtccta ggtgagtca 339

<210> SEQ ID NO 12
<211> LENGTH: 759
<212> TYPE: DNA
<213> ORGANISM: Homo sapiens

<400> SEQUENCE: 12
caggtgcagc tggtgcagtc tggggctgag gtgaagaagc ctgggtcctc ggtgagggtc 60
tcctgcaagg cttctggagg caccttcaac atctatagtg tcagctgggt gcgacaggcc 120
cctggacagg ggcttgagtg gatgggaagg atcatcccta tgcgtgatat tgcaaactac 180
gcgcagaggt tccagggcag ggtcacactt accgcggaca agtcctcggg gacagcctac 240
atggagttgc gcggcctgag atctgacgac acggccgtct attggtgtgc gacattggct 300
ggccccttgg actcctgggg ccagggcacc ctggtcaccg tctcgagtgg aggcggcggt 360
tcaggcggag gtggctctgg cggtggcgga agtgcacttt cttctgagct gactcaggac 420
ccagctgtgt ctgtgggctt gggacagaca gtcacgatca catgtcaagg cggcagcctc 480
agacaatatt atgcaagttg gtaccaacag aagccaggac aggcccctgt ggttgtcatc 540
tatggtaaaa ataagcgacc ctcagggatc ccagaccgat tctctggcac cacctcaggc 600
aacacagctt ccttgaccat cactggggct caggcggaag atgaggctga ctactattgt 660
aagtcccggg acagcagtgg taaccatccc ctttatgtct tcggagctgg gaccaagctg 720
accgtcctag gtgcggccgc acatcatcat caccatcac 759

<210> SEQ ID NO 13
<211> LENGTH: 15
<212> TYPE: DNA
<213> ORGANISM: Homo sapiens

<400> SEQUENCE: 13
atctatagtg tcagc 15

<210> SEQ ID NO 14
<211> LENGTH: 51
<212> TYPE: DNA
<213> ORGANISM: Homo sapiens

<400> SEQUENCE: 14
aggatcatcc ctatgcgtga tattgcaaac tacgcgcaga ggttccaggg c 51

<210> SEQ ID NO 15
<211> LENGTH: 21
<212> TYPE: DNA
<213> ORGANISM: Homo sapiens

<400> SEQUENCE: 15
ttggctggcc ccttggactc c 21

<210> SEQ ID NO 16
<211> LENGTH: 33
<212> TYPE: DNA
<213> ORGANISM: Homo sapiens

<400> SEQUENCE: 16
caaggcggca gcctcagaca atattatgca agt 33

<210> SEQ ID NO 17
<211> LENGTH: 21
<212> TYPE: DNA
<213> ORGANISM: Homo sapiens

<400> SEQUENCE: 17
ggtaaaaata agcgaccctc a 21

<210> SEQ ID NO 18
<211> LENGTH: 39
<212> TYPE: DNA
<213> ORGANISM: Homo sapiens

<400> SEQUENCE: 18
aagtcccggg acagcagtgg taaccatccc ctttatgtc 39

<210> SEQ ID NO 19
<211> LENGTH: 118
<212> TYPE: PRT
<213> ORGANISM: Homo sapiens

<400> SEQUENCE: 19

Glu Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Asp Glu Asp Thr Ala Val Tyr Tyr Cys
85 90 95

Ala Arg His Gly Gln Tyr Ala Leu Asp Ile Trp Gly Gln Gly Thr Met
100 105 110

Val Thr Val Ser Ser Gly
115

<210> SEQ ID NO 20
<211> LENGTH: 108

<212> TYPE: PRT
<213> ORGANISM: Homo sapiens

<400> SEQUENCE: 20

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Arg Ala Pro Lys Val Leu Ile
         35                  40                  45

Tyr Lys Ala Ser Thr Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gln Gly Thr Lys Leu Glu Ile Lys Arg
            100                 105
```

<210> SEQ ID NO 21
<211> LENGTH: 242
<212> TYPE: PRT
<213> ORGANISM: Homo sapiens

<400> SEQUENCE: 21

```
Glu Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Asp Glu Asp Thr Ala Val Tyr Tyr Cys
                 85                  90                  95

Ala Arg His Gly Gln Tyr Ala Leu Asp Ile Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Asp Ile Val Met Thr Gln Ser Pro Ser Thr Leu Ser
    130                 135                 140

Ala Ser Val Gly Asp Arg Val Thr Ile Thr Cys Arg Ala Ser Gln Gly
145                 150                 155                 160

Ile Ser Ser Trp Leu Ala Trp Tyr Gln Gln Lys Pro Gly Arg Ala Pro
                165                 170                 175

Lys Val Leu Ile Tyr Lys Ala Ser Thr Leu Glu Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Trp Thr Phe Gly Gln Gly Thr Lys Leu Glu Ile Lys Arg
225                 230                 235                 240

Ala Ala
```

<210> SEQ ID NO 22
<211> LENGTH: 5
<212> TYPE: PRT
<213> ORGANISM: Homo sapiens

<400> SEQUENCE: 22

Ser Tyr Gly Met His
1 5

<210> SEQ ID NO 23
<211> LENGTH: 17
<212> TYPE: PRT
<213> ORGANISM: Homo sapiens

<400> SEQUENCE: 23

Val Ile Ser Tyr Asp Gly Ser Asn Lys Tyr Tyr Ala Asp Ser Val Lys
1 5 10 15

Gly

<210> SEQ ID NO 24
<211> LENGTH: 9
<212> TYPE: PRT
<213> ORGANISM: Homo sapiens

<400> SEQUENCE: 24

His Gly Gln Tyr Ala Leu Asp Ile Trp
1 5

<210> SEQ ID NO 25
<211> LENGTH: 11
<212> TYPE: PRT
<213> ORGANISM: Homo sapiens

<400> SEQUENCE: 25

Arg Ala Ser Gln Gly Ile Ser Ser Trp Leu Ala
1 5 10

<210> SEQ ID NO 26
<211> LENGTH: 7
<212> TYPE: PRT
<213> ORGANISM: Homo sapiens

<400> SEQUENCE: 26

Lys Ala Ser Thr Leu Glu Ser
1 5

<210> SEQ ID NO 27
<211> LENGTH: 9
<212> TYPE: PRT
<213> ORGANISM: Homo sapiens

<400> SEQUENCE: 27

Gln Gln Ser Tyr Ser Thr Pro Trp Thr
1 5

<210> SEQ ID NO 28
<211> LENGTH: 417
<212> TYPE: DNA
<213> ORGANISM: Homo sapiens

<400> SEQUENCE: 28
atgaaattct tagtcaacgt tgcccttgtt tttatggtcg tgtacatttc ttacatctat 60
gcccaggtgc agctggtgga gtctggggga ggcgtggtcc agcctgggag gtccctgaga 120

```
ctctcctgtg cagcctctgg attcaccttc agtagctatg gcatgcactg ggtccgccag    180

gctccaggca aggggctgga gtgggtggca gttatatcat atgatggaag taataaatac    240

tatgcagact ccgtgaaggg ccgattcacc atctccagag acaattccaa gaacacgctg    300

tatctgcaaa tgaacagcct gagagacgag gacacggctg tgtattactg tgcgaggcat    360

ggtcagtacg ctcttgatat ctgggggcaa gggacaatgg tcaccgtctc ctcaggt       417
```

```
<210> SEQ ID NO 29
<211> LENGTH: 381
<212> TYPE: DNA
<213> ORGANISM: Homo sapiens

<400> SEQUENCE: 29

atgggatgga gctgtatcat cctcttcttg gtagcaacag ctacaggcgc gcactccgac     60

atccagatga cccagtctcc ttccaccctg tctgcatctg taggagacag agtcaccatc    120

acttgccggg ccagtcaggg tattagtagc tggttggcct ggtatcagca gaaaccaggg    180

agagccccta aggtcttgat ctataaggca tctactttag aaagtggggt cccatcaagg    240

ttcagcggca gtggatctgg gacagatttc actctcacca tcagcagtct gcaacctgaa    300

gattttgcaa cttactactg tcaacagagt tacagtaccc cgtggacgtt cggccaaggg    360

accaagctcg agatcaaacg t                                              381
```

```
<210> SEQ ID NO 30
<211> LENGTH: 728
<212> TYPE: DNA
<213> ORGANISM: Homo sapiens

<400> SEQUENCE: 30

gaggtgcagc tggtgcagtc tgggggaggc gtggtccagc ctgggaggtc cctgagactc     60

tcctgtgcag cctctggatt caccttcagt agctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agacgaggac acggctgtgt attactgtgc gaggcatggt    300

cagtacgctc ttgatatctg ggggcaaggg acaatggtca ccgtctcttc aggtggaggc    360

ggttcaggcg gaggtggcag cggcggtggc ggatcggaca tcgtgatgac ccagtctcct    420

tccaccctgt ctgcatctgt aggagacaga gtcaccatca cttgccgggc cagtcagggt    480

attagtagct ggttggcctg gtatcagcag aaaccaggga gagcccctaa ggtcttgatc    540

tataaggcat ctactttaga aagtggggtc ccatcaaggt tcagcggcag tggatctggg    600

acagatttca ctctcaccat cagcagtctg caacctgaag attttgcaac ttactactgt    660

caacagagtt acagtacccc gtggacgttc ggccaaggga ccaagctgga gatcaaacgt    720

gcggccgc                                                             728
```

```
<210> SEQ ID NO 31
<211> LENGTH: 18
<212> TYPE: DNA
<213> ORGANISM: Homo sapiens

<400> SEQUENCE: 31

agtagctatg gcatgcac                                                   18
```

```
<210> SEQ ID NO 32
<211> LENGTH: 51
```

<212> TYPE: DNA
<213> ORGANISM: Homo sapiens

<400> SEQUENCE: 32
gttatatcat atgatggaag taataaatac tatgcagact ccgtgaaggg c 51

<210> SEQ ID NO 33
<211> LENGTH: 30
<212> TYPE: DNA
<213> ORGANISM: Homo sapiens

<400> SEQUENCE: 33
aggcatggtc agtacgctct tgatatctgg 30

<210> SEQ ID NO 34
<211> LENGTH: 33
<212> TYPE: DNA
<213> ORGANISM: Homo sapiens

<400> SEQUENCE: 34
cgggccagtc agggtattag tagctggttg gcc 33

<210> SEQ ID NO 35
<211> LENGTH: 21
<212> TYPE: DNA
<213> ORGANISM: Homo sapiens

<400> SEQUENCE: 35
aaggcatcta ctttagaaag t 21

<210> SEQ ID NO 36
<211> LENGTH: 27
<212> TYPE: DNA
<213> ORGANISM: Homo sapiens

<400> SEQUENCE: 36
caacagagtt acagtacccc gtggacg 27

<210> SEQ ID NO 37
<211> LENGTH: 329
<212> TYPE: PRT
<213> ORGANISM: Homo sapiens

<400> SEQUENCE: 37

Ala Ser Thr Lys Gly Pro Ser Val Phe Pro Leu Ala Pro Ser Ser Gly
1 5 10 15

Thr Ser Gly Gly Thr Ala Ala Leu Gly Cys Leu Val Lys Asp Tyr Phe
20 25 30

Pro Glu Pro Val Thr Val Ser Trp Asn Ser Gly Ala Leu Thr Ser Gly
35 40 45

Val His Thr Phe Pro Ala Val Leu Gln Ser Ser Gly Leu Tyr Ser Leu
50 55 60

Ser Ser Val Val Thr Val Pro Ser Ser Ser Leu Gly Thr Gln Thr Tyr
65 70 75 80

Ile Cys Asn Val Asn His Lys Pro Ser Asn Thr Lys Val Asp Lys Lys
85 90 95

Val Glu Pro Lys Ser Cys Asp Lys Thr His Thr Cys Pro Pro Cys Pro
100 105 110

Ala Pro Glu Leu Leu Gly Gly Pro Ser Val Phe Leu Phe Pro Pro Lys
115 120 125

Pro Lys Asp Thr Leu Met Ile Ser Arg Thr Pro Glu Val Thr Cys Val

```
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325


<210> SEQ ID NO 38
<211> LENGTH: 1599
<212> TYPE: DNA
<213> ORGANISM: Homo sapiens

<400> SEQUENCE: 38

gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtc cacaccttcc cggctgtcct acagtcctca     180

ggactctact ccctcagcag cgtagtgacc gtgccctcca gcagcttggg cacccagacc     240

tacatctgca acgtgaatca caagcccagc aacaccaagg tggacaagaa agttggtgag     300

aggccagcac agggagggag ggtgtctgct ggaagccagg ctcagcgctc ctgcctggac     360

gcatcccggc tatgcagccc cagtccaggg cagcaaggca ggccccgtct gcctcttcac     420

ccggaggcct ctgcccgccc cactcatgct cagggagagg gtcttctggc tttttcccca     480

ggctctgggc aggcacaggc taggtgcccc taacccaggc cctgcacaca aaggggcagg     540

tgctgggctc agacctgcca agagccatat ccgggaggac cctgcccctg acctaagccc     600

accccaaagg ccaaactctc cactccctca gctcggacac cttctctcct cccagattcc     660

agtaactccc aatcttctct ctccagagcc caaatcttgt gacaaaactc acacatgccc     720

accgtgccca ggtaagccag cccaggcctc gccctccagc tcaaggcggg acaggtgccc     780

tagggtagcc tgcatccagg gacaggcccc agccgggtgc tgacacgtcc acctccatct     840

cttcctcagc acctgaactc ctggggggac cgtcagtctt cctcttcccc ccaaaaccca     900

aggacaccct catgatctcc cggacccctg aggtcacatg cgtggtggtg gacgtgagcc     960

acgaagaccc tgaggtcaag ttcaactggt acgtggacgg cgtggaggtg cataatgcca    1020
```

```
agacaaagcc gcgggaggag cagtacaaca gcacgtaccg tgtggtcagc gtcctcaccg   1080

tcctgcacca ggactggctg aatggcaagg agtacaagtg caaggtctcc aacaaagccc   1140

tcccagcccc catcgagaaa accatctcca aagccaaagg tgggacccgt ggggtgcgag   1200

ggccacatgg acagaggccg gctcggccca ccctctgccc tgagagtgac cgctgtacca   1260

acctctgtcc ctacagggca gccccgagaa ccacaggtgt acaccctgcc cccatcccgg   1320

gatgagctga ccaagaacca ggtcagcctg acctgcctgg tcaaaggctt ctatcccagc   1380

gacatcgccg tggagtggga gagcaatggg cagccggaga acaactacaa gaccacgcct   1440

cccgtgctgg actccgacgg ctccttcttc ctctacagca agctcaccgt ggacaagagc   1500

aggtggcagc aggggaacgt cttctcatgc tccgtgatgc atgaggctct gcacaaccac   1560

tacacgcaga agagcctctc cttaagtccg ggaaaataa                          1599
```

<210> SEQ ID NO 39
<211> LENGTH: 106
<212> TYPE: PRT
<213> ORGANISM: Homo sapiens

<400> SEQUENCE: 39

```
Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
     50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 40
<211> LENGTH: 321
<212> TYPE: DNA
<213> ORGANISM: Homo sapiens

<400> SEQUENCE: 40

```
ggtcagccca aggctgcccc ctcggtcact ctgttcccgc cctcctctga ggagcttcaa     60

gccaacaagg ccacactggt gtgtctcata agtgacttct acccgggagc cgtgacagtg    120

gcctggaagg cagatagcag ccccgtcaag gcgggagtgg agaccaccac accctccaaa    180

caaagcaaca acaagtacgc ggccagcagc tacctgagcc tgacgcctga gcagtggaag    240

tcccacagaa gctacagctg ccaggtcacg catgaaggga gcaccgtgga gaagacagtg    300

gcccctacag aatgttcata g                                              321
```

<210> SEQ ID NO 41
<211> LENGTH: 105
<212> TYPE: PRT
<213> ORGANISM: Homo sapiens

<400> SEQUENCE: 41

```
Val Ala Ala Pro Ser Val Phe Ile Phe Pro Pro Ser Asp Glu Gln Leu
  1               5                  10                  15
```

```
Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105


<210> SEQ ID NO 42
<211> LENGTH: 324
<212> TYPE: DNA
<213> ORGANISM: Homo sapiens

<400> SEQUENCE: 42

ggaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagttcacc ggtgacaaag     300

agcttcaaca ggggagagtg ttag                                            324


<210> SEQ ID NO 43
<211> LENGTH: 538
<212> TYPE: PRT
<213> ORGANISM: Homo sapiens

<400> SEQUENCE: 43

Met Pro Arg Gly Trp Ala Ala Pro Leu Leu Leu Leu Leu Leu Gln Gly
  1               5                  10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
```

-continued

```
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
    290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
    530                 535
```

<210> SEQ ID NO 44
<211> LENGTH: 2665
<212> TYPE: DNA
<213> ORGANISM: Homo sapiens

<400> SEQUENCE: 44

```
gtcgactgga ggcccagctg cccgtcatca gagtgacagg tcttatgaca gcctgattgg      60

tgactcgggc tgggtgtgga ttctcacccc aggcctctgc ctgctttctc agaccctcat     120
```

-continued

```
ctgtcacccc cacgctgaac ccagctgcca cccccagaag cccatcagac tgcccccagc    180
acacggaatg gatttctgag aaagaagccg aaacagaagg cccgtgggag tcagcatgcc    240
gcgtggctgg gccgcccccct tgctcctgct gctgctccag ggaggctggg gctgccccga    300
cctcgtctgc tacaccgatt acctccagac ggtcatctgc atcctggaaa tgtggaacct    360
ccaccccagc acgctcaccc ttacctggca agaccagtat gaagagctga aggacgaggc    420
cacctcctgc agcctccaca ggtcggccca caatgccacg catgccacct acacctgcca    480
catggatgta ttccacttca tggccgacga cattttcagt gtcaacatca cagaccagtc    540
tggcaactac tcccaggagt gtggcagctt tctcctggct gagagcatca agccggctcc    600
ccctttcaac gtgactgtga ccttctcagg acagtataat atctcctggc gctcagatta    660
cgaagaccct gccttctaca tgctgaaggg caagcttcag tatgagctgc agtacaggaa    720
ccggggagac ccctgggctg tgagtccgag gagaaagctg atctcagtgg actcaagaag    780
tgtctccctc ctcccccctgg agttccgcaa agactcgagc tatgagctgc aggtgcgggc    840
agggcccatg cctggctcct cctaccaggg gacctggagt gaatggagtg acccggtcat    900
ctttcagacc cagtcagagg agttaaagga aggctggaac cctcacctgc tgcttctcct    960
cctgcttgtc atagtcttca ttcctgcctt ctggagcctg aagacccatc cattgtggag   1020
gctatggaag aagatatggg ccgtccccag ccctgagcgg ttcttcatgc ccctgtacaa   1080
gggctgcagc ggagacttca agaaatgggt gggtgcaccc ttcactggct ccagcctgga   1140
gctgggaccc tggagcccag aggtgccctc caccctggag gtgtacagct gccacccacc   1200
acggagcccg gccaagaggc tgcagctcac ggagctacaa gaaccagcag agctggtgga   1260
gtctgacggt gtgcccaagc ccagcttctg gccgacagcc cagaactcgg ggggctcagc   1320
ttacagtgag gagagggatc ggccatacgg cctggtgtcc attgacacag tgactgtgct   1380
agatgcagag gggccatgca cctggccctg cagctgtgag gatgacggct acccagccct   1440
ggacctggat gctggcctgg agcccagccc aggcctagag gacccactct tggatgcagg   1500
gaccacagtc ctgtcctgtg gctgtgtctc agctggcagc cctgggctag gagggcccct   1560
gggaagcctc ctggacagac taaagccacc ccttgcagat ggggaggact gggctggggg   1620
actgccctgg ggtggccggt cacctggagg ggtctcagag agtgaggcgg gctcacccct   1680
ggccggcctg gatatggaca cgtttgacag tggctttgtg ggctctgact gcagcagccc   1740
tgtggagtgt gacttcacca gccccgggga cgaaggaccc ccccggagct acctccgcca   1800
gtgggtggtc attcctccgc cactttcgag ccctggaccc caggccagct aatgaggctg   1860
actggatgtc cagagctggc caggccactg ggccctgagc cagagacaag gtcacctggg   1920
ctgtgatgtg aagacacctg cagcctttgg tctcctggat gggcctttga gcctgatgtt   1980
tacagtgtct gtgtgtgtgt gtgcatatgt gtgtgtgtgc atatgcatgt gtgtgtgtgt   2040
gtgtgtctta ggtgcgcagt ggcatgtcca cgtgtgtgtg tgattgcacg tgcctgtggg   2100
cctgggataa tgcccatggt actccatgca ttcacctgcc ctgtgcatgt ctggactcac   2160
ggagctcacc catgtgcaca agtgtgcaca gtaaacgtgt ttgtggtcaa cagatgacaa   2220
cagccgtcct ccctcctagg gtcttgtgtt gcaagttggt ccacagcatc tccggggctt   2280
tgtgggatca gggcattgcc tgtgactgag gcggagccca gccctccagc gtctgcctcc   2340
aggagctgca agaagtccat attgttcctt atcacctgcc aacaggaagc gaaaggggat   2400
ggagtgagcc catggtgacc tcgggaatgg caatttttttg ggcggcccct ggacgaaggt   2460
ctgaatcccg actctgatac cttctggctg tgctacctga gccaagtcgc ctcccctctc   2520
```

```
tgggctagag tttccttatc cagacagtgg ggaaggcatg acacacctgg gggaaattgg   2580

cgatgtcacc cgtgtacggt acgcagccca gagcagaccc tcaataaacg tcagcttcct   2640

tcaaaaaaaa aaaaaaaaat ctaga                                         2665


<210> SEQ ID NO 45
<211> LENGTH: 529
<212> TYPE: PRT
<213> ORGANISM: Mus musculus

<400> SEQUENCE: 45

Met Pro Arg Gly Pro Val Ala Ala Leu Leu Leu Leu Ile Leu His Gly
  1               5                  10                  15

Ala Trp Ser Cys Leu Asp Leu Thr Cys Tyr Thr Asp Tyr Leu Trp Thr
             20                  25                  30

Ile Thr Cys Val Leu Glu Thr Arg Ser Pro Asn Pro Ser Ile Leu Ser
         35                  40                  45

Leu Thr Trp Gln Asp Glu Tyr Glu Glu Leu Gln Asp Gln Glu Thr Phe
     50                  55                  60

Cys Ser Leu His Arg Ser Gly His Asn Thr Thr His Ile Trp Tyr Thr
 65                  70                  75                  80

Cys His Met Arg Leu Ser Gln Phe Leu Ser Asp Glu Val Phe Ile Val
                 85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
    290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335

Glu Cys Asp Gly Met Ser Glu Pro Gly His Trp Cys Ile Ile Pro Leu
            340                 345                 350
```

```
Ala Ala Gly Gln Ala Val Ser Ala Tyr Ser Glu Glu Arg Asp Arg Pro
        355                 360                 365

Tyr Gly Leu Val Ser Ile Asp Thr Val Thr Val Gly Asp Ala Glu Gly
    370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
        435                 440                 445

Leu Ser Phe Ala Lys Glu Gly Asp Trp Thr Ala Asp Pro Thr Trp Arg
    450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Pro Val Asp Ser Gly Ala Gln Ser
        515                 520                 525

Ser
```

<210> SEQ ID NO 46
<211> LENGTH: 2628
<212> TYPE: DNA
<213> ORGANISM: Homo sapiens

<400> SEQUENCE: 46

```
gtcgacgcgg cggtaccagc tgtctgccca cttctcctgt ggtgtgcctc acggtcactt     60

gcttgtctga ccgcaagtct gcccatccct ggggcagcca actggcctca gcccgtgccc    120

caggcgtgcc ctgtctctgt ctggctgccc cagccctact gtcttcctct gtgtaggctc    180

tgcccagatg cccggctggt cctcagcctc aggactatct cagcagtgac tcccctgatt    240

ctggacttgc acctgactga actcctgccc acctcaaacc ttcacctccc accaccacca    300

ctccgagtcc cgctgtgact cccacgccca ggagaccacc caagtgcccc agcctaaaga    360

atggctttct gagaaagacc ctgaaggagt aggtctggga cacagcatgc cccggggccc    420

actggctgcc ttactcctgc tgattctcca tggagcttgg agctgcctgg acctcacttg    480

ctacactgac tacctctgga ccatcacctg tgtcctggag acacggagcc ccaaccccag    540

catactcagt ctcacctggc aagatgaata tgaggaactt caggaccaag agaccttctg    600

cagcctacac aggtctggcc acaacaccac acatatatgg tacacgtgcc atatgcgctt    660

gtctcaattc ctgtccgatg aagttttcat tgtcaatgtg acggaccagt ctggcaacaa    720

ctcccaagag tgtggcagct ttgtcctggc tgagagcatc aaaccagctc ccccccttgaa    780

cgtgactgtg gccttctcag gacgctatga tatctcctgg gactcagctt atgacgaacc    840

ctccaactac gtgctgaggg gcaagctaca atatgagctg cagtatcgga acctcagaga    900

cccctatgct gtgaggccgg tgaccaagct gatctcagtg gactcaagaa acgtctctct    960

tctccctgaa gagttccaca aagattctag ctaccagctg caggtgcggg cagcgcctca   1020

gccaggcact tcattcaggg ggacctggag tgagtggagt gaccccgtca tctttcagac   1080

ccaggctggg gagcccgagg caggctggga ccctcacatg ctgctgctcc tggctgtctt   1140
```

-continued

```
gatcattgtc ctggttttca tgggtctgaa gatccacctg ccttggaggc tatggaaaaa   1200
gatatgggca ccagtgccca cccctgagag tttcttccag cccctgtaca gggagcacag   1260
cgggaacttc aagaaatggg ttaatacccc tttcacggcc tccagcatag agttggtgcc   1320
acagagttcc acaacaacat cagccttaca tctgtcattg tatccagcca aggagaagaa   1380
gttcccgggg ctgccgggtc tggaagagca actggagtgt gatggaatgt ctgagcctgg   1440
tcactggtgc ataatcccct tggcagctgg ccaagcggtc tcagcctaca gtgaggagag   1500
agaccggcca tatggtctgg tgtccattga cacagtgact gtgggagatg cagagggcct   1560
gtgtgtctgg ccctgtagct gtgaggatga tggctatcca gccatgaacc tggatgctgg   1620
ccgagagtct ggccctaatt cagaggatct gctcttggtc acagaccctg cttttctgtc   1680
ttgcggctgt gtctcaggta gtggtctcag gcttggaggc tccccaggca gcctactgga   1740
caggttgagg ctgtcatttg caaaggaagg ggactggaca gcagacccaa cctggagaac   1800
tgggtcccca ggagggggct ctgagagtga agcaggttcc ccccctggtc tggacatgga   1860
cacatttgac agtggctttg caggttcaga ctgtggcagc cccgtggaga ctgatgaagg   1920
accccctcga agctatctcc gccagtgggt ggtcaggacc cctccacctg tggacagtgg   1980
agcccagagc agctagcata taataaccag ctatagtgag aagaggcctc tgagcctggc   2040
atttacagtg tgaacatgta ggggtgtgtg tgtgtgtgtg tgtgtgtgtg tgtgtgtgtg   2100
tgtgtgtgtg tgtgtgtgtg tgtcttgggt tgtgtgttag cacatccatg ttgggatttg   2160
gtctgttgct atgtattgta atgctaaatt ctctacccaa agttctaggc ctacgagtga   2220
attctcatgt ttacaaactt gctgtgtaaa ccttgttcct taatttaata ccattggtta   2280
aataaaattg gctgcaacca attactggag ggattagagg tagggggctt ttgagttacc   2340
tgtttggaga tggagaagga gagaggagag accaagagga gaaggaggaa ggagaggaga   2400
ggagaggaga ggagaggaga ggagaggaga ggagaggaga ggagaggaga ggctgccgtg   2460
aggggagagg gaccatgagc ctgtggccag gagaaacagc aagtatctgg ggtacactgg   2520
tgaggaggtg gccaggccag cagttagaag agtagattag ggtgacctc  cagtatttgt   2580
caaagccaat taaaataaca aaaaaaaaaa aaaagcggcc gctctaga                2628
```

```
<210> SEQ ID NO 47
<211> LENGTH: 116
<212> TYPE: PRT
<213> ORGANISM: Homo sapiens

<400> SEQUENCE: 47

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ile Tyr
            20                  25                  30

Ser Val Ser Trp Val Arg Gln Ala Pro Gly Gln Gly Leu Glu Trp Met
        35                  40                  45

Gly Arg Ile Ile Pro Met Arg Asp Ile Ala Asn Tyr Ala Gln Arg Phe
    50                  55                  60

Gln Gly Arg Val Thr Leu Thr Ala Asp Lys Ser Ser Gly Thr Ala Tyr
65                  70                  75                  80

Met Glu Leu Arg Ser Leu Arg Ser Asp Asp Thr Ala Val Tyr Trp Cys
                85                  90                  95

Ala Thr Leu Ala Gly Pro Leu Asp Ser Trp Gly Arg Gly Thr Leu Val
            100                 105                 110
```

Thr Val Ser Ser
115

<210> SEQ ID NO 48
<211> LENGTH: 109
<212> TYPE: PRT
<213> ORGANISM: Homo sapiens

<400> SEQUENCE: 48

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Thr Tyr Tyr Ala
20 25 30

Ser Trp Tyr Gln Lys Arg Pro Gly Gln Ala Pro Ile Leu Val Met Tyr
35 40 45

Gly Arg Asn Lys Arg Pro Ser Gly Ile Pro Asp Arg Phe Ser Gly Ser
50 55 60

Phe Ser Gly Asn Arg Ala Ser Leu Thr Ile Thr Gly Ala Gln Ala Glu
65 70 75 80

Asp Glu Ala Asp Tyr Tyr Cys Lys Ser Arg Ala Tyr Ser Gly Asn Leu
85 90 95

Val Glu Phe Gly Gly Gly Thr Lys Leu Thr Val Leu Gly
100 105

<210> SEQ ID NO 49
<211> LENGTH: 242
<212> TYPE: PRT
<213> ORGANISM: Homo sapiens

<400> SEQUENCE: 49

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Asn Ile Tyr
20 25 30

Ser Val Ser Trp Val Arg Gln Ala Pro Gly Gln Gly Leu Glu Trp Met
35 40 45

Gly Arg Ile Ile Pro Met Arg Asp Ile Ala Asn Tyr Ala Gln Arg Phe
50 55 60

Gln Gly Arg Val Thr Leu Thr Ala Asp Lys Ser Ser Gly Thr Ala Tyr
65 70 75 80

Met Glu Leu Arg Ser Leu Arg Ser Asp Asp Thr Ala Val Tyr Trp Cys
85 90 95

Ala Thr Leu Ala Gly Pro Leu Asp Ser Trp Gly Arg Gly Thr Leu Val
100 105 110

Thr Val Ser Ser Gly Gly Gly Gly Ser Gly Gly Gly Gly Ser Gly Gly
115 120 125

Gly Gly Ser Ala Leu Ser Ser Glu Leu Thr Gln Asp Pro Ala Val Ser
130 135 140

Val Ala Leu Gly Gln Thr Val Arg Ile Thr Cys Gln Gly Asp Ser Leu
145 150 155 160

Arg Thr Tyr Tyr Ala Ser Trp Tyr Gln Lys Arg Pro Gly Gln Ala Pro
165 170 175

Ile Leu Val Met Tyr Gly Arg Asn Lys Arg Pro Ser Gly Ile Pro Asp
180 185 190

Arg Phe Ser Gly Ser Phe Ser Gly Asn Arg Ala Ser Leu Thr Ile Thr
195 200 205

Gly Ala Gln Ala Glu Asp Glu Ala Asp Tyr Tyr Cys Lys Ser Arg Ala

```
    210                 215                 220

Tyr Ser Gly Asn Leu Val Glu Phe Gly Gly Gly Thr Lys Leu Thr Val
225                 230                 235                 240

Leu Gly


<210> SEQ ID NO 50
<211> LENGTH: 5
<212> TYPE: PRT
<213> ORGANISM: Homo sapiens

<400> SEQUENCE: 50

Ile Tyr Ser Val Ser
  1               5


<210> SEQ ID NO 51
<211> LENGTH: 17
<212> TYPE: PRT
<213> ORGANISM: Homo sapiens

<400> SEQUENCE: 51

Arg Ile Ile Pro Met Arg Asp Ile Ala Asn Tyr Ala Gln Arg Phe Gln
  1               5                  10                  15

Gly


<210> SEQ ID NO 52
<211> LENGTH: 7
<212> TYPE: PRT
<213> ORGANISM: Homo sapiens

<400> SEQUENCE: 52

Leu Ala Gly Pro Leu Asp Ser
  1               5


<210> SEQ ID NO 53
<211> LENGTH: 11
<212> TYPE: PRT
<213> ORGANISM: Homo sapiens

<400> SEQUENCE: 53

Gln Gly Asp Ser Leu Arg Thr Tyr Tyr Ala Ser
  1               5                  10


<210> SEQ ID NO 54
<211> LENGTH: 7
<212> TYPE: PRT
<213> ORGANISM: Homo sapiens

<400> SEQUENCE: 54

Gly Arg Asn Lys Arg Pro Ser
  1               5


<210> SEQ ID NO 55
<211> LENGTH: 11
<212> TYPE: PRT
<213> ORGANISM: Homo sapiens

<400> SEQUENCE: 55

Lys Ser Arg Ala Tyr Ser Gly Asn Leu Val Glu
  1               5                  10


<210> SEQ ID NO 56
<211> LENGTH: 348
<212> TYPE: DNA
<213> ORGANISM: Homo sapiens
```

-continued

<400> SEQUENCE: 56
gaggtgcagc tggtgcagtc tggggctgag gtgaagaagc ctgggtcctc ggtgaaggtc 60
tcctgcaagg cttctggagg caccttcaac atctatagtg tcagctgggt gcgacaggcc 120
cctggacagg ggcttgagtg gatgggaagg atcatcccta tgcgtgatat tgcaaactac 180
gcgcagaggt tccagggcag ggtcacactt accgcggaca agtcctcggg gacagcctac 240
atggagttgc gcagcctgag atctgacgac acggccgtct attggtgtgc gacattggct 300
ggccccttgg actcctgggg cagaggaacc ctggtcaccg tctcgagt 348

<210> SEQ ID NO 57
<211> LENGTH: 327
<212> TYPE: DNA
<213> ORGANISM: Homo sapiens

<400> SEQUENCE: 57
tcttctgagc tgactcagga ccctgctgtg tctgtggcct tgggacagac agtcaggatc 60
acatgccagg gagacagcct cagaacttat tatgcgagct ggtaccagaa gaggccagga 120
caggccccta tacttgtcat gtatggtaga aataagaggc cctcagggat cccagaccga 180
ttctctggct ccttctcagg gaacagagct tccttgacca tcactggggc tcaggcggaa 240
gatgaggctg actattactg taaatcccgg gcctacagtg gtaacctcgt agaattcggc 300
ggagggacca agctgaccgt cctaggt 327

<210> SEQ ID NO 58
<211> LENGTH: 726
<212> TYPE: DNA
<213> ORGANISM: Homo sapiens

<400> SEQUENCE: 58
gaggtgcagc tggtgcagtc tggggctgag gtgaagaagc ctgggtcctc ggtgaaggtc 60
tcctgcaagg cttctggagg caccttcaac atctatagtg tcagctgggt gcgacaggcc 120
cctggacagg ggcttgagtg gatgggaagg atcatcccta tgcgtgatat tgcaaactac 180
gcgcagaggt tccagggcag ggtcacactt accgcggaca agtcctcggg gacagcctac 240
atggagttgc gcagcctgag atctgacgac acggccgtct attggtgtgc gacattggct 300
ggccccttgg actcctgggg cagaggaacc ctggtcaccg tctcgagtgg aggcggcggt 360
tcaggcggag gtggctctgg cggtggcgga agtgcacttt cttctgagct gactcaggac 420
cctgctgtgt ctgtggcctt gggacagaca gtcaggatca catgccaggg agacagcctc 480
agaacttatt atgcgagctg gtaccagaag aggccaggac aggcccctat acttgtcatg 540
tatggtagaa ataagaggcc ctcagggatc ccagaccgat tctctggctc cttctcaggg 600
aacagagctt ccttgaccat cactggggct caggcggaag atgaggctga ctattactgt 660
aaatcccggg cctacagtgg taacctcgta gaattcggcg gagggaccaa gctgaccgtc 720
ctaggt 726

<210> SEQ ID NO 59
<211> LENGTH: 15
<212> TYPE: DNA
<213> ORGANISM: Homo sapiens

<400> SEQUENCE: 59
atctatagtg tcagc 15

<210> SEQ ID NO 60
<211> LENGTH: 51
<212> TYPE: DNA
<213> ORGANISM: Homo sapiens

<400> SEQUENCE: 60
aggatcatcc ctatgcgtga tattgcaaac tacgcgcaga ggttccaggg c 51

<210> SEQ ID NO 61
<211> LENGTH: 21
<212> TYPE: DNA
<213> ORGANISM: Homo sapiens

<400> SEQUENCE: 61
ttggctggcc ccttggactc c 21

<210> SEQ ID NO 62
<211> LENGTH: 33
<212> TYPE: DNA
<213> ORGANISM: Homo sapiens

<400> SEQUENCE: 62
cagggagaca gcctcagaac ttattatgcg agc 33

<210> SEQ ID NO 63
<211> LENGTH: 21
<212> TYPE: DNA
<213> ORGANISM: Homo sapiens

<400> SEQUENCE: 63
ggtagaaata agaggccctc a 21

<210> SEQ ID NO 64
<211> LENGTH: 33
<212> TYPE: DNA
<213> ORGANISM: Homo sapiens

<400> SEQUENCE: 64
aaatcccggg cctacagtgg taacctcgta gaa 33

<210> SEQ ID NO 65
<211> LENGTH: 118
<212> TYPE: PRT
<213> ORGANISM: Homo sapiens

<400> SEQUENCE: 65

```
Gln Val Gln Leu Gln Glu Ser Gly Pro Gly Leu Val Lys Thr Ser Glu
  1               5                  10                  15

Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
         35                  40                  45

Ile Gly Ser Ile Ser His Thr Gly Asn Thr Tyr Tyr Asn Pro Pro Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Gly Ile Ser Arg Pro Glu Tyr Trp Gly Lys Gly Thr
            100                 105                 110

Leu Val Thr Val Ser Ser
        115
```

<210> SEQ ID NO 66
<211> LENGTH: 110
<212> TYPE: PRT
<213> ORGANISM: Homo sapiens

<400> SEQUENCE: 66

```
Ser Ser Glu Leu Thr Gln Asp Pro Pro Val Ser Val Ala Leu Gly Gln
  1               5                  10                  15

Thr Val Thr Leu Thr Cys Gln Gly Asp Ser Leu Arg Thr Tyr Tyr Ala
             20                  25                  30

Ser Trp Tyr Gln Gln Lys Ser Gly Gln Ala Pro Ile Leu Leu Leu Tyr
         35                  40                  45

Gly Lys His Lys Arg Pro Ser Gly Ile Pro Asp Arg Phe Ser Gly Ser
     50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Pro
                 85                  90                  95

His Val Leu Phe Gly Gly Gly Thr Gln Leu Thr Val Leu Ser
            100                 105                 110
```

<210> SEQ ID NO 67
<211> LENGTH: 245
<212> TYPE: PRT
<213> ORGANISM: Homo sapiens

<400> SEQUENCE: 67

```
Gln Val Gln Leu Gln Glu Ser Gly Pro Gly Leu Val Lys Thr Ser Glu
  1               5                  10                  15

Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
         35                  40                  45

Ile Gly Ser Ile Ser His Thr Gly Asn Thr Tyr Tyr Asn Pro Pro Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Asn Ser
    210                 215                 220
```

```
Arg Asp Ser Ser Gly Asn Pro His Val Leu Phe Gly Gly Gly Thr Gln
225                 230                 235                 240

Leu Thr Val Leu Ser
                245


<210> SEQ ID NO 68
<211> LENGTH: 6
<212> TYPE: PRT
<213> ORGANISM: Homo sapiens

<400> SEQUENCE: 68

Ser Gly Tyr Tyr Trp Gly
  1               5


<210> SEQ ID NO 69
<211> LENGTH: 16
<212> TYPE: PRT
<213> ORGANISM: Homo sapiens

<400> SEQUENCE: 69

Ser Ile Ser His Thr Gly Asn Thr Tyr Tyr Asn Pro Pro Leu Lys Ser
  1               5                   10                  15


<210> SEQ ID NO 70
<211> LENGTH: 9
<212> TYPE: PRT
<213> ORGANISM: Homo sapiens

<400> SEQUENCE: 70

Gly Gly Gly Ile Ser Arg Pro Glu Tyr
  1               5


<210> SEQ ID NO 71
<211> LENGTH: 11
<212> TYPE: PRT
<213> ORGANISM: Homo sapiens

<400> SEQUENCE: 71

Gln Gly Asp Ser Leu Arg Thr Tyr Tyr Ala Ser
  1               5                   10


<210> SEQ ID NO 72
<211> LENGTH: 7
<212> TYPE: PRT
<213> ORGANISM: Homo sapiens

<400> SEQUENCE: 72

Gly Lys His Lys Arg Pro Ser
  1               5


<210> SEQ ID NO 73
<211> LENGTH: 12
<212> TYPE: PRT
<213> ORGANISM: Homo sapiens

<400> SEQUENCE: 73

Asn Ser Arg Asp Ser Ser Gly Asn Pro His Val Leu
  1               5                   10


<210> SEQ ID NO 74
<211> LENGTH: 354
<212> TYPE: DNA
<213> ORGANISM: Homo sapiens

<400> SEQUENCE: 74
```

-continued caggtgcagc tgcaggagtc gggcccagga ctggtgaaga cttcggagac cctgtccctc 60
acctgcgctg tctctggtta ctccatcagc agtggttact actggggctg gatccggcag 120
cccccaggga aggggttgga gtggattggg agtatctctc atactgggaa cacctactac 180
aacccgcccc tcaagagtcg cgtcaccata tcagtagaca cgtccaagaa ccagttctcc 240
ctgaaactga gctctgtgac cgccgcagac acggccgtgt attactgtgc gcgaggtggg 300
ggaattagca ggccggagta ctggggcaaa ggcaccctgg tcaccgtctc gagt 354

<210> SEQ ID NO 75
<211> LENGTH: 330
<212> TYPE: DNA
<213> ORGANISM: Homo sapiens

<400> SEQUENCE: 75
tcttctgagc tgactcagga ccctcctgtg tctgtggcct tgggacagac agtcacgctc 60
acatgccaag gagacagcct cagaacctat tatgcaagct ggtaccagca gaagtcagga 120
caggccccta tacttctcct ctatggtaaa cacaaacggc cctcagggat cccagaccgc 180
ttctctggct ccacctcagg agacacagct tccttgacca tcactggggc tcaggcggaa 240
gacgaggctg actattactg taactcccgg gactccagtg gcaacccccca tgttctgttc 300 ggcggaggga cccagctcac cgttttaagt 330

<210> SEQ ID NO 76
<211> LENGTH: 735
<212> TYPE: DNA
<213> ORGANISM: Homo sapiens

<400> SEQUENCE: 76
caggtgcagc tgcaggagtc gggcccagga ctggtgaaga cttcggagac cctgtccctc 60
acctgcgctg tctctggtta ctccatcagc agtggttact actggggctg gatccggcag 120
cccccaggga aggggttgga gtggattggg agtatctctc atactgggaa cacctactac 180
aacccgcccc tcaagagtcg cgtcaccata tcagtagaca cgtccaagaa ccagttctcc 240
ctgaaactga gctctgtgac cgccgcagac acggccgtgt attactgtgc gcgaggtggg 300
ggaattagca ggccggagta ctggggcaaa ggcaccctgg tcaccgtctc gagtggaggc 360
ggcggttcag gcggaggtgg ctctggcggt ggcggaagtg cactttcttc tgagctgact 420
caggaccctc ctgtgtctgt ggccttggga cagacagtca cgctcacatg ccaaggagac 480
agcctcagaa cctattatgc aagctggtac cagcagaagt caggacaggc ccctatactt 540
ctcctctatg gtaaacacaa acggccctca gggatcccag accgcttctc tggctccacc 600
tcaggagaca cagcttcctt gaccatcact ggggctcagg cggaagacga ggctgactat 660
tactgtaact cccgggactc cagtggcaac ccccatgttc tgttcggcgg agggacccag 720
ctcaccgttt taagt 735

<210> SEQ ID NO 77
<211> LENGTH: 18
<212> TYPE: DNA
<213> ORGANISM: Homo sapiens

<400> SEQUENCE: 77
agtggttact actggggc 18

<210> SEQ ID NO 78
<211> LENGTH: 48
<212> TYPE: DNA

<213> ORGANISM: Homo sapiens

<400> SEQUENCE: 78
agtatctctc atactgggaa cacctactac aacccgcccc tcaagagt 48

<210> SEQ ID NO 79
<211> LENGTH: 27
<212> TYPE: DNA
<213> ORGANISM: Homo sapiens

<400> SEQUENCE: 79
ggtgggggaa ttagcaggcc ggagtac 27

<210> SEQ ID NO 80
<211> LENGTH: 33
<212> TYPE: DNA
<213> ORGANISM: Homo sapiens

<400> SEQUENCE: 80
caaggagaca gcctcagaac ctattatgca agc 33

<210> SEQ ID NO 81
<211> LENGTH: 21
<212> TYPE: DNA
<213> ORGANISM: Homo sapiens

<400> SEQUENCE: 81
ggtaaacaca aacggccctc a 21

<210> SEQ ID NO 82
<211> LENGTH: 36
<212> TYPE: DNA
<213> ORGANISM: Homo sapiens

<400> SEQUENCE: 82
aactcccggg actccagtgg caaccccat gttctg 36

<210> SEQ ID NO 83
<211> LENGTH: 116
<212> TYPE: PRT
<213> ORGANISM: Homo sapiens

<400> SEQUENCE: 83

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Ile Tyr
             20                  25                  30

Ser Val Ser Trp Val Arg Gln Ala Pro Gly Gln Gly Leu Glu Trp Met
         35                  40                  45

Gly Arg Ile Ile Pro Met Arg Asp Ile Ala Asn Tyr Ala Gln Arg Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Leu Ala Gly Pro Leu Asp Ser Trp Gly Gln Gly Thr Leu Val
            100                 105                 110

Thr Val Ser Ser
        115
```

<210> SEQ ID NO 84

<211> LENGTH: 111
<212> TYPE: PRT
<213> ORGANISM: Homo sapiens

<400> SEQUENCE: 84

```
Ser Ser Glu Leu Thr Gln Asp Pro Ala Val Ser Val Ala Leu Gly Gln
  1               5                  10                  15

Thr Val Arg Ile Thr Cys Gln Gly Gly Ser Leu Arg Gln Tyr Tyr Ala
             20                  25                  30

Ser Trp Tyr Gln Gln Lys Pro Gly Gln Ala Pro Val Leu Val Ile Tyr
         35                  40                  45

Gly Lys Asn Lys Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Lys Ser Arg Asp Ser Ser Gly Asn His
                 85                  90                  95

Pro Leu Tyr Val Phe Gly Ala Gly Thr Lys Leu Thr Val Leu Gly
            100                 105                 110
```

<210> SEQ ID NO 85
<211> LENGTH: 244
<212> TYPE: PRT
<213> ORGANISM: Homo sapiens

<400> SEQUENCE: 85

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Ile Tyr
             20                  25                  30

Ser Val Ser Trp Val Arg Gln Ala Pro Gly Gln Gly Leu Glu Trp Met
         35                  40                  45

Gly Arg Ile Ile Pro Met Arg Asp Ile Ala Asn Tyr Ala Gln Arg Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Leu Ala Gly Pro Leu Asp Ser Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ala Leu Ser Ser Glu Leu Thr Gln Asp Pro Ala Val Ser
    130                 135                 140

Val Ala Leu Gly Gln Thr Val Arg Ile Thr Cys Gln Gly Gly Ser Leu
145                 150                 155                 160

Arg Gln Tyr Tyr Ala Ser Trp Tyr Gln Gln Lys Pro Gly Gln Ala Pro
                165                 170                 175

Val Leu Val Ile Tyr Gly Lys Asn Lys Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Lys Ser Arg Asp
    210                 215                 220

Ser Ser Gly Asn His Pro Leu Tyr Val Phe Gly Ala Gly Thr Lys Leu
225                 230                 235                 240
```

Thr Val Leu Gly

<210> SEQ ID NO 86
<211> LENGTH: 5
<212> TYPE: PRT
<213> ORGANISM: Homo sapiens

<400> SEQUENCE: 86

Ile Tyr Ser Val Ser
1 5

<210> SEQ ID NO 87
<211> LENGTH: 17
<212> TYPE: PRT
<213> ORGANISM: Homo sapiens

<400> SEQUENCE: 87

Arg Ile Ile Pro Met Arg Asp Ile Ala Asn Tyr Ala Gln Arg Phe Gln
1 5 10 15

Gly

<210> SEQ ID NO 88
<211> LENGTH: 7
<212> TYPE: PRT
<213> ORGANISM: Homo sapiens

<400> SEQUENCE: 88

Leu Ala Gly Pro Leu Asp Ser
1 5

<210> SEQ ID NO 89
<211> LENGTH: 11
<212> TYPE: PRT
<213> ORGANISM: Homo sapiens

<400> SEQUENCE: 89

Gln Gly Gly Ser Leu Arg Gln Tyr Tyr Ala Ser
1 5 10

<210> SEQ ID NO 90
<211> LENGTH: 7
<212> TYPE: PRT
<213> ORGANISM: Homo sapiens

<400> SEQUENCE: 90

Gly Lys Asn Lys Arg Pro Ser
1 5

<210> SEQ ID NO 91
<211> LENGTH: 13
<212> TYPE: PRT
<213> ORGANISM: Homo sapiens

<400> SEQUENCE: 91

Lys Ser Arg Asp Ser Ser Gly Asn His Pro Leu Tyr Val
1 5 10

<210> SEQ ID NO 92
<211> LENGTH: 348
<212> TYPE: DNA
<213> ORGANISM: Homo sapiens

<400> SEQUENCE: 92
caggtgcagc tggtgcagtc tggggctgag gtgaagaagc ctgggtcctc ggtgaaggtc 60

-continued

| | |
|---|---|
| tcctgcaagg cttctggagg caccttcaac atctatagtg tcagctgggt gcgacaggcc | 120 |
| cctggacagg ggcttgagtg gatgggaagg atcatcccta tgcgtgatat tgcaaactac | 180 |
| gcgcagaggt tccagggcag ggtcacaatt accgcggaca agtccacgag cacagcctac | 240 |
| atggagttga gcagcctgag atctgaagac acggccgtct attattgtgc gacattggct | 300 |
| ggccccttgg actcctgggg ccagggcacc ctggtcaccg tctcgagt | 348 |

<210> SEQ ID NO 93
<211> LENGTH: 333
<212> TYPE: DNA
<213> ORGANISM: Homo sapiens

<400> SEQUENCE: 93

| | |
|---|---|
| tcttctgagc tgactcagga cccagctgtg tctgtggcct tgggacagac agtcaggatc | 60 |
| acatgtcaag gcggcagcct cagacaatat tatgcaagtt ggtaccaaca gaagccagga | 120 |
| caggcccctg tgcttgtcat ctatggtaaa aataagcgac cctcagggat cccagaccga | 180 |
| ttctctggct cctcctcagg caacacagct tccttgacca tcactggggc tcaggcggaa | 240 |
| gatgaggctg actactattg taagtcccgg gacagcagtg gtaaccatcc cctttatgtc | 300 |
| ttcggagctg ggaccaagct gaccgtccta ggt | 333 |

<210> SEQ ID NO 94
<211> LENGTH: 732
<212> TYPE: DNA
<213> ORGANISM: Homo sapiens

<400> SEQUENCE: 94

| | |
|---|---|
| caggtgcagc tggtgcagtc tggggctgag gtgaagaagc ctgggtcctc ggtgaaggtc | 60 |
| tcctgcaagg cttctggagg caccttcaac atctatagtg tcagctgggt gcgacaggcc | 120 |
| cctggacagg ggcttgagtg gatgggaagg atcatcccta tgcgtgatat tgcaaactac | 180 |
| gcgcagaggt tccagggcag ggtcacaatt accgcggaca agtccacgag cacagcctac | 240 |
| atggagttga gcagcctgag atctgaagac acggccgtct attattgtgc gacattggct | 300 |
| ggccccttgg actcctgggg ccagggcacc ctggtcaccg tctcgagtgg aggcggcggt | 360 |
| tcaggcggag gtggctctgg cggtggcgga agtgcacttt cttctgagct gactcaggac | 420 |
| ccagctgtgt ctgtggcctt gggacagaca gtcaggatca catgtcaagg cggcagcctc | 480 |
| agacaatatt atgcaagttg gtaccaacag aagccaggac aggcccctgt gcttgtcatc | 540 |
| tatggtaaaa ataagcgacc ctcagggatc ccagaccgat tctctggctc ctcctcaggc | 600 |
| aacacagctt ccttgaccat cactggggct caggcggaag atgaggctga ctactattgt | 660 |
| aagtcccggg acagcagtgg taaccatccc ctttatgtct tcggagctgg gaccaagctg | 720 |
| accgtcctag gt | 732 |

<210> SEQ ID NO 95
<211> LENGTH: 15
<212> TYPE: DNA
<213> ORGANISM: Homo sapiens

<400> SEQUENCE: 95

| | |
|---|---|
| atctatagtg tcagc | 15 |

<210> SEQ ID NO 96
<211> LENGTH: 51
<212> TYPE: DNA
<213> ORGANISM: Homo sapiens

<400> SEQUENCE: 96
aggatcatcc ctatgcgtga tattgcaaac tacgcgcaga ggttccaggg c 51

<210> SEQ ID NO 97
<211> LENGTH: 21
<212> TYPE: DNA
<213> ORGANISM: Homo sapiens

<400> SEQUENCE: 97
ttggctggcc ccttggactc c 21

<210> SEQ ID NO 98
<211> LENGTH: 33
<212> TYPE: DNA
<213> ORGANISM: Homo sapiens

<400> SEQUENCE: 98
caaggcggca gcctcagaca atattatgca agt 33

<210> SEQ ID NO 99
<211> LENGTH: 21
<212> TYPE: DNA
<213> ORGANISM: Homo sapiens

<400> SEQUENCE: 99
ggtaaaaata agcgaccctc a 21

<210> SEQ ID NO 100
<211> LENGTH: 39
<212> TYPE: DNA
<213> ORGANISM: Homo sapiens

<400> SEQUENCE: 100
aagtcccggg acagcagtgg taaccatccc ctttatgtc 39

<210> SEQ ID NO 101
<211> LENGTH: 120
<212> TYPE: PRT
<213> ORGANISM: Homo sapiens

<400> SEQUENCE: 101

```
Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Asp Asn
             20                  25                  30

Tyr Ile His Trp Val Arg Gln Ala Pro Gly Gln Gly Leu Glu Trp Met
         35                  40                  45

Gly Trp Ile Asn Pro Lys Thr Gly Gly Thr Asn Tyr Ala Gln Lys Phe
     50                  55                  60

Gln Gly Arg Val Ser Met Thr Arg Asp Thr Ser Ile Asn Thr Ala Tyr
 65                  70                  75                  80

Met Asp Leu Ser Arg Leu Thr Ser Asp Asp Thr Ala Val Tyr Tyr Cys
                 85                  90                  95

Thr Arg Ser Leu Ser Pro Tyr Gly Gly Gln Leu Leu Tyr Trp Gly Arg
            100                 105                 110

Gly Thr Met Val Thr Val Ser Ser
        115                 120
```

<210> SEQ ID NO 102
<211> LENGTH: 110
<212> TYPE: PRT

<213> ORGANISM: Homo sapiens

<400> SEQUENCE: 102

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Arg Tyr Tyr Ala
20 25 30

Ser Trp Phe Gln Gln Lys Pro Gly Gln Ala Pro Val Leu Val Ile Phe
35 40 45

Gly Lys Asn Asn Arg Pro Ser Gly Ile Pro Asp Arg Phe Ser Ala Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Thr Ser Ile Asn His
85 90 95

Pro Val Ile Phe Gly Gly Gly Thr Lys Leu Thr Val Leu Gly
100 105 110

<210> SEQ ID NO 103
<211> LENGTH: 247
<212> TYPE: PRT
<213> ORGANISM: Homo sapiens

<400> SEQUENCE: 103

Glu Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Thr Asp Asn
20 25 30

Tyr Ile His Trp Val Arg Gln Ala Pro Gly Gln Gly Leu Glu Trp Met
35 40 45

Gly Trp Ile Asn Pro Lys Thr Gly Gly Thr Asn Tyr Ala Gln Lys Phe
50 55 60

Gln Gly Arg Val Ser Met Thr Arg Asp Thr Ser Ile Asn Thr Ala Tyr
65 70 75 80

Met Asp Leu Ser Arg Leu Thr Ser Asp Asp Thr Ala Val Tyr Tyr Cys
85 90 95

Thr Arg Ser Leu Ser Pro Tyr Gly Gly Gln Leu Leu Tyr Trp Gly Arg
100 105 110

Gly Thr Met Val Thr Val Ser Ser Gly Gly Gly Gly Ser Gly Gly Gly
115 120 125

Gly Ser Gly Gly Gly Gly Ser Ala Leu Ser Ser Glu Leu Thr Gln Asp
130 135 140

Pro Ala Val Ser Val Ala Leu Gly Gln Thr Val Arg Ile Thr Cys Gln
145 150 155 160

Gly Asp Ser Leu Arg Arg Tyr Tyr Ala Ser Trp Phe Gln Gln Lys Pro
165 170 175

Gly Gln Ala Pro Val Leu Val Ile Phe Gly Lys Asn Asn Arg Pro Ser
180 185 190

Gly Ile Pro Asp Arg Phe Ser Ala Ser Ser Ser Gly Asn Thr Ala Ser
195 200 205

Leu Thr Ile Thr Gly Ala Gln Ala Glu Asp Glu Ala Asp Tyr Tyr Cys
210 215 220

Asn Ser Arg Asp Thr Ser Ile Asn His Pro Val Ile Phe Gly Gly Gly
225 230 235 240

Thr Lys Leu Thr Val Leu Gly
245

<210> SEQ ID NO 104
<211> LENGTH: 5
<212> TYPE: PRT
<213> ORGANISM: Homo sapiens

<400> SEQUENCE: 104

Asp Asn Tyr Ile His
1 5

<210> SEQ ID NO 105
<211> LENGTH: 17
<212> TYPE: PRT
<213> ORGANISM: Homo sapiens

<400> SEQUENCE: 105

Trp Ile Asn Pro Lys Thr Gly Gly Thr Asn Tyr Ala Gln Lys Phe Gln
1 5 10 15

Gly

<210> SEQ ID NO 106
<211> LENGTH: 11
<212> TYPE: PRT
<213> ORGANISM: Homo sapiens

<400> SEQUENCE: 106

Ser Leu Ser Pro Tyr Gly Gly Gln Leu Leu Tyr
1 5 10

<210> SEQ ID NO 107
<211> LENGTH: 11
<212> TYPE: PRT
<213> ORGANISM: Homo sapiens

<400> SEQUENCE: 107

Gln Gly Asp Ser Leu Arg Arg Tyr Tyr Ala Ser
1 5 10

<210> SEQ ID NO 108
<211> LENGTH: 7
<212> TYPE: PRT
<213> ORGANISM: Homo sapiens

<400> SEQUENCE: 108

Gly Lys Asn Asn Arg Pro Ser
1 5

<210> SEQ ID NO 109
<211> LENGTH: 12
<212> TYPE: PRT
<213> ORGANISM: Homo sapiens

<400> SEQUENCE: 109

Asn Ser Arg Asp Thr Ser Ile Asn His Pro Val Ile
1 5 10

<210> SEQ ID NO 110
<211> LENGTH: 360
<212> TYPE: DNA
<213> ORGANISM: Homo sapiens

<400> SEQUENCE: 110
gaggtccagc tggtgcagtc tggagctgag gtgaagaagc ctggggcctc agtgaaggtc 60
tcctgtaagg cttccggata cgccttcacc gacaactata tacactgggt gcgacaggcc 120
cctggacaag ggcttgaatg gatgggatgg atcaacccta agactggtgg cacaaactat 180
gcacaaaagt ttcagggcag ggtcagcatg accagggaca cgtccatcaa cacagcctac 240
atggacctaa gtaggctgac atctgacgac acggccgtct attactgtac gagaagcctt 300
tccccatatg gtggccaact cctctactgg ggccggggga caatggtcac cgtctcgagt 360

<210> SEQ ID NO 111
<211> LENGTH: 330
<212> TYPE: DNA
<213> ORGANISM: Homo sapiens

<400> SEQUENCE: 111
tcttctgagc tgactcagga ccctgctgtg tctgtggcct tgggacagac agtcaggatc 60
acatgccaag gagacagcct cagaagatat tatgcaagct ggttccagca gaagccagga 120
caggcccctg tacttgtcat ctttggtaaa aacaaccggc cctcagggat cccagaccga 180
ttctctgcct ccagttcagg aaacacagct tccttgacca tcactggggc tcaggcggaa 240
gatgaggctg actattactg taactcccgg gacaccagta ttaaccatcc cgtgatattc 300
ggcgggggga ccaagctgac cgtcctaggt 330

<210> SEQ ID NO 112
<211> LENGTH: 741
<212> TYPE: DNA
<213> ORGANISM: Homo sapiens

<400> SEQUENCE: 112
gaggtccagc tggtgcagtc tggagctgag gtgaagaagc ctggggcctc agtgaaggtc 60
tcctgtaagg cttccggata cgccttcacc gacaactata tacactgggt gcgacaggcc 120
cctggacaag ggcttgaatg gatgggatgg atcaacccta agactggtgg cacaaactat 180
gcacaaaagt ttcagggcag ggtcagcatg accagggaca cgtccatcaa cacagcctac 240
atggacctaa gtaggctgac atctgacgac acggccgtct attactgtac gagaagcctt 300
tccccatatg gtggccaact cctctactgg ggccggggga caatggtcac cgtctcgagt 360
ggaggcggcg gttcaggcgg aggtggctct ggcggtggcg gaagtgcact ttcttctgag 420
ctgactcagg accctgctgt gtctgtggcc ttgggacaga cagtcaggat cacatgccaa 480
ggagacagcc tcagaagata ttatgcaagc tggttccagc agaagccagg acaggcccct 540
gtacttgtca tctttggtaa aaacaaccgg ccctcaggga tcccagaccg attctctgcc 600
tccagttcag gaaacacagc ttccttgacc atcactgggg ctcaggcgga agatgaggct 660
gactattact gtaactcccg ggacaccagt attaaccatc ccgtgatatt cggcgggggg 720
accaagctga ccgtcctagg t 741

<210> SEQ ID NO 113
<211> LENGTH: 15
<212> TYPE: DNA
<213> ORGANISM: Homo sapiens

<400> SEQUENCE: 113
gacaactata tacac 15

<210> SEQ ID NO 114
<211> LENGTH: 54
<212> TYPE: DNA
<213> ORGANISM: Homo sapiens

<400> SEQUENCE: 114

-continued tggatcaacc ctaagactgg tggcacaaac tatgcacaaa agtttcaggg cagg 54

<210> SEQ ID NO 115
<211> LENGTH: 33
<212> TYPE: DNA
<213> ORGANISM: Homo sapiens

<400> SEQUENCE: 115
agcctttccc catatggtgg ccaactcctc tac 33

<210> SEQ ID NO 116
<211> LENGTH: 33
<212> TYPE: DNA
<213> ORGANISM: Homo sapiens

<400> SEQUENCE: 116
caaggagaca gcctcagaag atattatgca agc 33

<210> SEQ ID NO 117
<211> LENGTH: 21
<212> TYPE: DNA
<213> ORGANISM: Homo sapiens

<400> SEQUENCE: 117
ggtaaaaaca accggccctc a 21

<210> SEQ ID NO 118
<211> LENGTH: 36
<212> TYPE: DNA
<213> ORGANISM: Homo sapiens

<400> SEQUENCE: 118
aactcccggg acaccagtat taaccatccc gtgata 36

<210> SEQ ID NO 119
<211> LENGTH: 118
<212> TYPE: PRT
<213> ORGANISM: Homo sapiens

<400> SEQUENCE: 119

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Gly Trp Lys Leu Pro Phe Phe Ala Tyr Trp Gly Arg Gly Thr
            100                 105                 110

Leu Val Thr Val Ser Ser
        115
```

<210> SEQ ID NO 120
<211> LENGTH: 110
<212> TYPE: PRT
<213> ORGANISM: Homo sapiens

<400> SEQUENCE: 120

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Phe Tyr Ala
            20                  25                  30

Asn Trp Tyr Gln Gln Lys Pro Gly Gln Ala Pro Ile Leu Val Ile Tyr
        35                  40                  45

Gly Lys Ser Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Tyr Ser Arg Asp Arg Ser Gly Asn His
                85                  90                  95

Leu Gly Met Phe Gly Gly Gly Thr Lys Leu Thr Val Leu Gly
            100                 105                 110

<210> SEQ ID NO 121
<211> LENGTH: 245
<212> TYPE: PRT
<213> ORGANISM: Homo sapiens

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Trp Lys Leu Pro Phe Phe Ala Tyr Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Thr Phe Tyr Ala Asn Trp Tyr Gln Gln Lys Pro Gly Gln
                165                 170                 175

Ala Pro Ile Leu Val Ile Tyr Gly Lys Ser Asn Arg Pro Ser Gly Ile
            180                 185                 190

Pro Asp Arg Phe Ser Gly Ser Ser Ser Gly Asn Thr Ala Ser Leu Thr
        195                 200                 205

Ile Thr Gly Ala Gln Ala Glu Asp Glu Ala Asp Tyr Tyr Cys Tyr Ser
    210                 215                 220

Arg Asp Arg Ser Gly Asn His Leu Gly Met Phe Gly Gly Gly Thr Lys
225                 230                 235                 240

Leu Thr Val Leu Gly
                245

<210> SEQ ID NO 122
<211> LENGTH: 5
<212> TYPE: PRT
<213> ORGANISM: Homo sapiens

<400> SEQUENCE: 122

Ser Tyr Ala Met Ser
1 5

<210> SEQ ID NO 123
<211> LENGTH: 17
<212> TYPE: PRT
<213> ORGANISM: Homo sapiens

<400> SEQUENCE: 123

Ala Ile Ser Gly Ser Gly Gly Ser Thr Tyr Tyr Ala Asp Ser Val Lys
1 5 10 15

Gly

<210> SEQ ID NO 124
<211> LENGTH: 9
<212> TYPE: PRT
<213> ORGANISM: Homo sapiens

<400> SEQUENCE: 124

Gly Trp Lys Leu Pro Phe Phe Ala Tyr
1 5

<210> SEQ ID NO 125
<211> LENGTH: 11
<212> TYPE: PRT
<213> ORGANISM: Homo sapiens

<400> SEQUENCE: 125

Gln Gly Asp Ser Leu Arg Thr Phe Tyr Ala Asn
1 5 10

<210> SEQ ID NO 126
<211> LENGTH: 7
<212> TYPE: PRT
<213> ORGANISM: Homo sapiens

<400> SEQUENCE: 126

Gly Lys Ser Asn Arg Pro Ser
1 5

<210> SEQ ID NO 127
<211> LENGTH: 12
<212> TYPE: PRT
<213> ORGANISM: Homo sapiens

<400> SEQUENCE: 127

Tyr Ser Arg Asp Arg Ser Gly Asn His Leu Gly Met
1 5 10

<210> SEQ ID NO 128
<211> LENGTH: 354
<212> TYPE: DNA
<213> ORGANISM: Homo sapiens

<400> SEQUENCE: 128
gaggtgcagc tgttggagtc tgggggaggc ttggtacagc ctggggggtc cctgagactc 60
tcctgtgcag cctctggatt cacctttagc agctatgcca tgagctgggt ccgccaggct 120

-continued ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtgt attactgtgc ggggggggtgg 300 aaacttccat tttttgccta ctggggccgg ggcaccctgg tcaccgtctc gagt 354

<210> SEQ ID NO 129
<211> LENGTH: 330
<212> TYPE: DNA
<213> ORGANISM: Homo sapiens

<400> SEQUENCE: 129
tcttctgagc tgactcagga ccctgctgtg tctgtggcct tgggacagac agtcaggatc 60
acatgccaag gagacagcct cagaaccttt tatgcaaact ggtaccagca gaagccagga 120
caggccccta tacttgtcat ctatggtaaa agcaaccgtc cctcagggat cccagaccga 180
ttctctggct ccagctcagg aaacacagct tccttgacca tcactggggc tcaggcggaa 240
gatgaggctg actattactg ttactcccgg gacagaagtg gtaaccatct agggatgttc 300
ggcggaggga ccaagctgac cgtcctaggt 330

<210> SEQ ID NO 130
<211> LENGTH: 735
<212> TYPE: DNA
<213> ORGANISM: Homo sapiens

<400> SEQUENCE: 130
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtgt attactgtgc ggggggggtgg 300 aaacttccat tttttgccta ctggggccgg ggcaccctgg tcaccgtctc gagtggaggc 360
ggcggttcag gcggaggtgg ctctggcggt ggcggaagtg cactttcttc tgagctgact 420
caggaccctg ctgtgtctgt ggccttggga cagacagtca ggatcacatg ccaaggagac 480
agcctcagaa ccttttatgc aaactggtac cagcagaagc caggacaggc ccctatactt 540
gtcatctatg gtaaaagcaa ccgtccctca gggatcccag accgattctc tggctccagc 600
tcaggaaaca cagcttcctt gaccatcact ggggctcagg cggaagatga ggctgactat 660
tactgttact cccgggacag aagtggtaac catctaggga tgttcggcgg agggaccaag 720
ctgaccgtcc taggt 735

<210> SEQ ID NO 131
<211> LENGTH: 15
<212> TYPE: DNA
<213> ORGANISM: Homo sapiens

<400> SEQUENCE: 131
agctatgcca tgagc 15

<210> SEQ ID NO 132
<211> LENGTH: 54
<212> TYPE: DNA
<213> ORGANISM: Homo sapiens

<400> SEQUENCE: 132
gctattagtg gtagtggtgg tagcacatac tacgcagact ccgtgaaggg ccgg 54

<210> SEQ ID NO 133
<211> LENGTH: 27
<212> TYPE: DNA
<213> ORGANISM: Homo sapiens

<400> SEQUENCE: 133
gggtggaaac ttccattttt tgcctac 27

<210> SEQ ID NO 134
<211> LENGTH: 33
<212> TYPE: DNA
<213> ORGANISM: Homo sapiens

<400> SEQUENCE: 134
caaggagaca gcctcagaac cttttatgca aac 33

<210> SEQ ID NO 135
<211> LENGTH: 21
<212> TYPE: DNA
<213> ORGANISM: Homo sapiens

<400> SEQUENCE: 135
ggtaaaagca accgtccctc a 21

<210> SEQ ID NO 136
<211> LENGTH: 36
<212> TYPE: DNA
<213> ORGANISM: Homo sapiens

<400> SEQUENCE: 136
tactcccggg acagaagtgg taaccatcta gggatg 36

<210> SEQ ID NO 137
<211> LENGTH: 121
<212> TYPE: PRT
<213> ORGANISM: Homo sapiens

<400> SEQUENCE: 137

```
Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Gly Ile Ser Gly Ser Gly Thr Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr His Ile Ser Glu Arg Pro Arg Gly Ala Phe Asp Ile Trp Gly
            100                 105                 110

Arg Gly Thr Met Val Thr Val Ser Ser
        115                 120
```

<210> SEQ ID NO 138
<211> LENGTH: 109
<212> TYPE: PRT
<213> ORGANISM: Homo sapiens

<400> SEQUENCE: 138

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Lys Tyr His Ala
20 25 30

Thr Trp Tyr Gln Gln Lys Pro Arg Gln Ala Pro Val Leu Val Val Tyr
35 40 45

Gly Lys Asn Arg Arg Pro Ser Gly Ile Pro Asp Arg Phe Ser Gly Ser
50 55 60

Ser Ser Gly Asn Thr Ala Ser Leu Thr Ile Thr Gly Ala Gln Ala Gly
65 70 75 80

Asp Glu Ala Asp Tyr Tyr Cys Asn Ser Arg Asp Thr Ser Gly Leu His
85 90 95

Tyr Val Phe Gly Ala Gly Thr Lys Leu Thr Val Leu Gly
100 105

<210> SEQ ID NO 139
<211> LENGTH: 247
<212> TYPE: PRT
<213> ORGANISM: Homo sapiens

<400> SEQUENCE: 139

Gln Val Gln Leu Gln Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Gly Ile Ser Gly Ser Gly Thr Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr His Ile Ser Glu Arg Pro Arg Gly Ala Phe Asp Ile Trp Gly
100 105 110

Arg Gly Thr Met Val Thr Val Ser Ser Gly Gly Gly Gly Ser Gly Gly
115 120 125

Gly Gly Ser Gly Gly Gly Gly Ser Ala Leu Ser Ser Glu Leu Thr Gln
130 135 140

Asp Pro Ala Val Ser Val Ala Leu Gly Gln Thr Val Arg Ile Thr Cys
145 150 155 160

Gln Gly Asp Ser Leu Arg Lys Tyr His Ala Thr Trp Tyr Gln Gln Lys
165 170 175

Pro Arg Gln Ala Pro Val Leu Val Val Tyr Gly Lys Asn Arg Arg Pro
180 185 190

Ser Gly Ile Pro Asp Arg Phe Ser Gly Ser Ser Ser Gly Asn Thr Ala
195 200 205

Ser Leu Thr Ile Thr Gly Ala Gln Ala Gly Asp Glu Ala Asp Tyr Tyr
210 215 220

Cys Asn Ser Arg Asp Thr Ser Gly Leu His Tyr Val Phe Gly Ala Gly
225 230 235 240

Thr Lys Leu Thr Val Leu Gly
245

```
<210> SEQ ID NO 140
<211> LENGTH: 5
<212> TYPE: PRT
<213> ORGANISM: Homo sapiens

<400> SEQUENCE: 140

Ser Tyr Ala Met Ser
 1               5

<210> SEQ ID NO 141
<211> LENGTH: 17
<212> TYPE: PRT
<213> ORGANISM: Homo sapiens

<400> SEQUENCE: 141

Gly Ile Ser Gly Ser Gly Thr Ser Thr Tyr Tyr Ala Asp Ser Val Lys
 1               5                  10                  15

Gly

<210> SEQ ID NO 142
<211> LENGTH: 12
<212> TYPE: PRT
<213> ORGANISM: Homo sapiens

<400> SEQUENCE: 142

His Ile Ser Glu Arg Pro Arg Gly Ala Phe Asp Ile
 1               5                  10

<210> SEQ ID NO 143
<211> LENGTH: 11
<212> TYPE: PRT
<213> ORGANISM: Homo sapiens

<400> SEQUENCE: 143

Gln Gly Asp Ser Leu Arg Lys Tyr His Ala Thr
 1               5                  10

<210> SEQ ID NO 144
<211> LENGTH: 7
<212> TYPE: PRT
<213> ORGANISM: Homo sapiens

<400> SEQUENCE: 144

Gly Lys Asn Arg Arg Pro Ser
 1               5

<210> SEQ ID NO 145
<211> LENGTH: 11
<212> TYPE: PRT
<213> ORGANISM: Homo sapiens

<400> SEQUENCE: 145

Asn Ser Arg Asp Thr Ser Gly Leu His Tyr Val
 1               5                  10

<210> SEQ ID NO 146
<211> LENGTH: 363
<212> TYPE: DNA
<213> ORGANISM: Homo sapiens

<400> SEQUENCE: 146

caggtgcagc tgcaggagtc ggggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcaggt attagtggta gtggtactag cacatactac     180
```

gcagactccg tgaagggccg gttcaccatc tccagagaca attccaagaa cacgctgtat 240
ctgcaaatga acagcctgag agccgaagac acggccgtat attactgtgc gacacatatc 300
tcggaacgtc cacgtggtgc ttttgatatc tggggccggg ggacaatggt caccgtctcg 360
agt 363

<210> SEQ ID NO 147
<211> LENGTH: 327
<212> TYPE: DNA
<213> ORGANISM: Homo sapiens

<400> SEQUENCE: 147
tcttctgagc tgactcagga ccctgctgtg tctgtggccc tgggacagac agtcaggatc 60
acatgccaag gagacagcct cagaaagtat catgcaactt ggtaccagca gaagccaagg 120
caggcccctg tacttgtcgt ctatggtaaa aacaggcgcc cctcagggat ccccgaccga 180
ttctctggct ccagctcagg aaacacagct tccctgacca tcactggggc tcaggcggga 240
gatgaggctg actattactg taactcccgg gacaccagtg gtcttcatta tgtcttcgga 300
gctgggacca agctgaccgt cctaggt 327

<210> SEQ ID NO 148
<211> LENGTH: 741
<212> TYPE: DNA
<213> ORGANISM: Homo sapiens

<400> SEQUENCE: 148
caggtgcagc tgcaggagtc gggggaggc ttggtacagc ctgggggtc cctgagactc 60 tcctgtgcag cctctggatt cacctttagc agctatgcca tgagctgggt ccgccaggct 120
ccagggaagg ggctggagtg ggtctcaggt attagtggta gtggtactag cacatactac 180
gcagactccg tgaagggccg gttcaccatc tccagagaca attccaagaa cacgctgtat 240
ctgcaaatga acagcctgag agccgaagac acggccgtat attactgtgc gacacatatc 300
tcggaacgtc cacgtggtgc ttttgatatc tggggccggg ggacaatggt caccgtctcg 360
agtggaggcg gcggttcagg cggaggtggc tctggcggtg gcggaagtgc actttcttct 420
gagctgactc aggaccctgc tgtgtctgtg gccctgggac agacagtcag gatcacatgc 480
caaggagaca gcctcagaaa gtatcatgca acttggtacc agcagaagcc aaggcaggcc 540
cctgtacttg tcgtctatgg taaaaacagg cgcccctcag ggatccccga ccgattctct 600
ggctccagct caggaaacac agcttccctg accatcactg gggctcaggc gggagatgag 660
gctgactatt actgtaactc ccgggacacc agtggtcttc attatgtctt cggagctggg 720
accaagctga ccgtcctagg t 741

<210> SEQ ID NO 149
<211> LENGTH: 15
<212> TYPE: DNA
<213> ORGANISM: Homo sapiens

<400> SEQUENCE: 149
agctatgcca tgagc 15

<210> SEQ ID NO 150
<211> LENGTH: 51
<212> TYPE: DNA
<213> ORGANISM: Homo sapiens

<400> SEQUENCE: 150

-continued

```
ggtattagtg gtagtggtac tagcacatac tacgcagact ccgtgaaggg c                51


<210> SEQ ID NO 151
<211> LENGTH: 36
<212> TYPE: DNA
<213> ORGANISM: Homo sapiens

<400> SEQUENCE: 151

catatctcgg aacgtccacg tggtgctttt gatatc                                 36


<210> SEQ ID NO 152
<211> LENGTH: 33
<212> TYPE: DNA
<213> ORGANISM: Homo sapiens

<400> SEQUENCE: 152

caaggagaca gcctcagaaa gtatcatgca act                                    33


<210> SEQ ID NO 153
<211> LENGTH: 21
<212> TYPE: DNA
<213> ORGANISM: Homo sapiens

<400> SEQUENCE: 153

ggtaaaaaca ggcgcccctc a                                                 21


<210> SEQ ID NO 154
<211> LENGTH: 33
<212> TYPE: DNA
<213> ORGANISM: Homo sapiens

<400> SEQUENCE: 154

aactcccggg acaccagtgg tcttcattat gtc                                    33
```